US009447172B2

(12) United States Patent
Kato et al.

(10) Patent No.: US 9,447,172 B2
(45) Date of Patent: Sep. 20, 2016

(54) VACCINIA VIRUS H3L AND B5R SPECIFIC MONOCLONAL ANTIBODIES AND METHODS OF MAKING AND USING SAME

(71) Applicants: KYOWA HAKKO KIRIN CO., LTD., Tokyo (JP); LA JOLLA INSTITUTE FOR ALLERGY AND IMMUNOLOGY, La Jolla, CA (US)

(72) Inventors: Shinichiro Kato, Chiba (JP); Steve Granger, Encinitas, CA (US); Shane Crotty, San Diego, CA (US); Sandra Rickert, Encinitas, CA (US); Lilia Koriazova, San Diego, CA (US); Tomoyuki Tahara, San Diego, CA (US)

(73) Assignees: KYOWA HAKKO KIRIN CO., LTD., Tokyo (JP); LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 14 days.

(21) Appl. No.: 14/142,520

(22) Filed: Dec. 27, 2013

(65) Prior Publication Data

US 2014/0186370 A1 Jul. 3, 2014

Related U.S. Application Data

(63) Continuation of application No. 12/682,539, filed as application No. PCT/US2008/078955 on Oct. 6, 2008, now Pat. No. 8,623,370, which is a continuation-in-part of application No. PCT/US2008/078316, filed on Sep. 30, 2008.

(60) Provisional application No. 60/979,028, filed on Oct. 10, 2007, provisional application No. 61/127,729, filed on May 14, 2008.

(51) Int. Cl.
*A61K 39/395* (2006.01)
*A61K 39/42* (2006.01)
*C07K 16/08* (2006.01)
*A61K 39/00* (2006.01)

(52) U.S. Cl.
CPC ....... *C07K 16/081* (2013.01); *A61K 2039/507* (2013.01); *C07K 2317/565* (2013.01); *C07K 2317/734* (2013.01)

(58) Field of Classification Search
None
See application file for complete search history.

(56) References Cited

U.S. PATENT DOCUMENTS 7,393,533 B1 7/2008 Crotty et al.
8,623,370 B2 * 1/2014 Kato .................... C07K 16/081 424/130.1

FOREIGN PATENT DOCUMENTS

WO 03/068151 A2 8/2003
WO 03/068151 A3 8/2003
WO 2007/075915 A2 7/2007

OTHER PUBLICATIONS

Elgert K. (1998). Antibody Structure and Function (Chapter 4) in Immunology: Understanding the Immune System. Hoboken, NJ, USA John Wiley & Sons, Inc.*

(Continued)

*Primary Examiner* — Daniel E Kolker
*Assistant Examiner* — Stuart W Snyder
(74) *Attorney, Agent, or Firm* — Pillsbury Winthrop Shaw Pittman LLP

(57) ABSTRACT

The invention relates to antibodies and subsequences thereof that specifically bind to poxvirus B5R envelope protein, antibodies and subsequences thereof that specifically bind to poxvirus H3L envelope protein, and combinations thereof.

19 Claims, 19 Drawing Sheets

(56) References Cited

OTHER PUBLICATIONS

Aldaz-Carroll, L, et al., Epitope-Mapping Studies Define Two Major Neutralization Sites on the Vaccinia Virus Extracellular Enveloped Virus Glycoprotein B5R, Journal of Virology, 2005, 79:6260-6271.

Bell, E., et al., Antibodies Against the Extracellular Enveloped Virus B5R Protein are Mainly Responsible for the EEV Neutralizing Capacity of Vaccinia Immune Globulin, Virology, 2004, 325:425-431.

Davies, D. H., et al., Vaccinia Virus H3L Envelope Protein Is a Major Target of Neutralizing Antibodies in Humans and Elicits Protection Against Lethal Challenge in Mice, Journal of Virology, 2005, 79(18):11724-11733.

Law, M., et al., Antibody Neutralization of the Extracellular Enveloped Form of Vaccinia Virus, Virology, 2001, 280:132-142.

Rudikoff, et al., Single Amino Acid Substitution Altering Antigen-Binding Specificity, Proc. Natl. Acad. Sci. USA, 79:1979-1983.

* cited by examiner

VACV Infected Cells

VACV Infected Cells+C'

VACV Infected Cells+B96+C'

VACV Infected Cells+B126+C'

SEQUENCE LISTING

```
<160> NUMBER OF SEQ ID NOS: 124

<210> SEQ ID NO 1
<211> LENGTH: 420
<212> TYPE: DNA
<213> ORGANISM: Homo sapiens

<400> SEQUENCE: 1

atggagtttg ggctgagctg gctttttctt gtggctattt taaaaggtgt ccagtgtgag      60

gtgcagctgt tggaggccgg gggaggcttg gtacagcctg gggggtccct gagactctcc     120
```

-continued

```
tgtgcagcct ctggattcac ctttagcagc tctgccatga gctgggtccg ccaggctcca    180

gggaaggggc tggagtgggt ctcagttatt agtattagtg gtggtagcac atactacgca    240

gactccgtga agggccggtt caccatctcc agagacaatt ccaagaacac gctgaatctg    300

caaatgaaca gcctgagagc cgaggacacg gccgtatatt actgtgcgaa agaaactcgg    360

tactattatt cctacggtat ggacgtctgg ggccaaggga ccacggtcac cgtctcctca    420


<210> SEQ ID NO 2
<211> LENGTH: 140
<212> TYPE: PRT
<213> ORGANISM: Homo sapiens

<400> SEQUENCE: 2

Met Glu Phe Gly Leu Ser Trp Leu Phe Leu Val Ala Ile Leu Lys Gly
1               5                   10                  15

Val Gln Cys Glu Val Gln Leu Leu Glu Ala Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Ser Ala Met Ser Trp Val Arg Gln Ala Pro Gly Lys Gly Leu
    50                  55                  60

Glu Trp Val Ser Val Ile Ser Ile Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Asn Leu Gln Met Asn Ser Leu Arg Ala Glu Asp Thr Ala Val
            100                 105                 110

Tyr Tyr Cys Ala Lys Glu Thr Arg Tyr Tyr Tyr Ser Tyr Gly Met Asp
        115                 120                 125

Val Trp Gly Gln Gly Thr Thr Val Thr Val Ser Ser
    130                 135                 140


<210> SEQ ID NO 3
<211> LENGTH: 387
<212> TYPE: DNA
<213> ORGANISM: Homo sapiens

<400> SEQUENCE: 3

atggacatga gggtccccgc tcagctcctg gggcttctgc tgctctggct cccaggtgcc     60

agatgtgcca tccagttgac ccagtctcca tcctccctgt ctgcatctgt aggggacaga    120

gtcaccatca cttgccgggc aagtcagcgc attggctttg ctttagcctg gtatcagcag    180

aaaccaggga aagctcctaa actcctgatc catgatgcct ccagtttgga aactggggtc    240

ccatcaaggt tcagcggcag tggatctggg acagatttca ctctcgccat cagcagcctg    300

cagcctgaag attttgcaac ttattactgt caacagttta atacttaccc attcactttc    360

ggccctggga ccaaagtgga tatcaaa                                        387


<210> SEQ ID NO 4
<211> LENGTH: 129
<212> TYPE: PRT
<213> ORGANISM: Homo sapiens

<400> SEQUENCE: 4

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
```

-continued

```
            20                  25                  30

Leu Ser Ala Ser Val Gly Asp Arg Val Thr Ile Thr Cys Arg Ala Ser
        35                  40                  45

Gln Arg Ile Gly Phe Ala Leu Ala Trp Tyr Gln Gln Lys Pro Gly Lys
    50                  55                  60

Ala Pro Lys Leu Leu Ile His Asp Ala Ser Ser Leu Glu Thr Gly Val
65                  70                  75                  80

Pro Ser Arg Phe Ser Gly Ser Gly Ser Gly Thr Asp Phe Thr Leu Ala
                85                  90                  95

Ile Ser Ser Leu Gln Pro Glu Asp Phe Ala Thr Tyr Tyr Cys Gln Gln
            100                 105                 110

Phe Asn Thr Tyr Pro Phe Thr Phe Gly Pro Gly Thr Lys Val Asp Ile
        115                 120                 125

Lys


<210> SEQ ID NO 5
<211> LENGTH: 420
<212> TYPE: DNA
<213> ORGANISM: Homo sapiens

<400> SEQUENCE: 5

atggaactgg ggctccgctg ggttttcctt gttgctattt tagaaggtgt ccagtgtgag      60

gtgcagctgg tggagtctgg gggaggcctg gtcaagcctg gggggtccct gagactctcc     120

tgtgcagcct ctggattcac gttcagcagc tatagcatga actgggtccg ccaggctcca     180

gggaagggac tggagtgggt ctcatctatt agtagtagta gaagtttcat atactacgca     240

gactcagtga agggccgatt caccatctcc agagacatcg ccaagaactc actgtctctg     300

caaatgagca gcctgagagt cgaggacacg gctgtgtatt actgtgcgag agaaaggagg     360

tactactact cctacggtct ggacgtctgg ggccaaggga ccacggtcac cgtctcctca     420


<210> SEQ ID NO 6
<211> LENGTH: 140
<212> TYPE: PRT
<213> ORGANISM: Homo sapiens

<400> SEQUENCE: 6

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Ile Ser Ser Ser Arg Ser Phe Ile Tyr Tyr Ala
65                  70                  75                  80

Asp Ser Val Lys Gly Arg Phe Thr Ile Ser Arg Asp Ile Ala Lys Asn
                85                  90                  95

Ser Leu Ser Leu Gln Met Ser Ser Leu Arg Val Glu Asp Thr Ala Val
            100                 105                 110

Tyr Tyr Cys Ala Arg Glu Arg Arg Tyr Tyr Tyr Ser Tyr Gly Leu Asp
        115                 120                 125

Val Trp Gly Gln Gly Thr Thr Val Thr Val Ser Ser
    130                 135                 140
```

<210> SEQ ID NO 7
<211> LENGTH: 387
<212> TYPE: DNA
<213> ORGANISM: Homo sapiens

<400> SEQUENCE: 7
atggacatga gggtccccgc tcagctcctg gggcttctgc tgctctggct cccaggtgcc 60
agatgtgcca tccagttgac ccagtctcca tcctccctgt ctgcatctgt aggagacaga 120
gtcaccatca cttgccgggc aagtcagggc attagcagtg ccttagcctg gtatcagcag 180
aaaccaggga aagctcctaa gctcctgatc tatgatgcct ccagtttgga aagtggggtc 240
ccatcaaggt tcagcggcag tggatctggg acagatttca ctctcaccat cagcagcctg 300
cagcctgaag attttgcaac ttattactgt caacagttta atagttaccc gtacactttt 360
ggccagggga ccaagctgga gatcaaa 387

<210> SEQ ID NO 8
<211> LENGTH: 129
<212> TYPE: PRT
<213> ORGANISM: Homo sapiens

<400> SEQUENCE: 8

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Tyr Thr Phe Gly Gln Gly Thr Lys Leu Glu Ile
        115                 120                 125

Lys

<210> SEQ ID NO 9
<211> LENGTH: 387
<212> TYPE: DNA
<213> ORGANISM: Homo sapiens

<400> SEQUENCE: 9
atggacatga gggtccccgc tcagctcctg gggcttctgc tgctctggct cccaggtgcc 60
agatgtgcca tccagttgac ccagtctcca tcctccctgt ctgcatctgt aggggacaga 120
gtcaccatca cttgccgggc aagtcagcgc attggctttg ctttagcctg gtatcagcag 180
aaaccaggga aagctcctaa actcctgatc catgatgcct ccagtttgga aactggggtc 240
ccatcaaggt tcagcggcag tggatctggg acagatttca ctctcgccat cagcagcctg 300
cagcctgaag attttgcaac ttattactgt caacagttta atacttaccc attcactttc 360
ggccctggga ccaaagtgga tatcaaa 387

```
<210> SEQ ID NO 10
<211> LENGTH: 129
<212> TYPE: PRT
<213> ORGANISM: Homo sapiens

<400> SEQUENCE: 10

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Arg Ile Gly Phe Ala Leu Ala Trp Tyr Gln Gln Lys Pro Gly Lys
    50                  55                  60

Ala Pro Lys Leu Leu Ile His Asp Ala Ser Ser Leu Glu Thr Gly Val
65                  70                  75                  80

Pro Ser Arg Phe Ser Gly Ser Gly Ser Gly Thr Asp Phe Thr Leu Ala
                85                  90                  95

Ile Ser Ser Leu Gln Pro Glu Asp Phe Ala Thr Tyr Tyr Cys Gln Gln
            100                 105                 110

Phe Asn Thr Tyr Pro Phe Thr Phe Gly Pro Gly Thr Lys Val Asp Ile
        115                 120                 125

Lys


<210> SEQ ID NO 11
<211> LENGTH: 420
<212> TYPE: DNA
<213> ORGANISM: Homo sapiens

<400> SEQUENCE: 11

atggaactgg ggctccgctg ggttttcctt gttgctattt tagaaggtgt ccagtgtgag      60

gtgcagctgg tggagtctgg gggaggcctg gtcaagtctg gggggtccct gagactctcc     120

tgtgcagcct ctggattcac cctcagtagc tatagcatga actgggtccg ccaggctcca     180

gggaaggggc tggagtgggt ctcatccatt agtagtagta gtagttacat atactacgca     240

gactcagtga agggccgatt caccatctcc agagacatcg ccaagaactc actgtctctg     300

caaatgagca gcctgagagc cgaggacacg gctgtgtatt actgtgcgag agaaaggagg     360

tactactact cctacggtat ggacgtctgg ggccaaggga ccacggtcac cgtctcctca     420


<210> SEQ ID NO 12
<211> LENGTH: 140
<212> TYPE: PRT
<213> ORGANISM: Homo sapiens

<400> SEQUENCE: 12

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Ser Gly Gly Ser Leu Arg Leu Ser Cys Ala Ala Ser Gly Phe Thr Leu
        35                  40                  45

Ser Ser Tyr Ser Met Asn Trp Val Arg Gln Ala Pro Gly Lys Gly Leu
    50                  55                  60

Glu Trp Val Ser Ser Ile Ser Ser Ser Ser Ser Tyr Ile Tyr Tyr Ala
65                  70                  75                  80

Asp Ser Val Lys Gly Arg Phe Thr Ile Ser Arg Asp Ile Ala Lys Asn
```

```
                85                  90                  95

Ser Leu Ser Leu Gln Met Ser Ser Leu Arg Ala Glu Asp Thr Ala Val
            100                 105                 110

Tyr Tyr Cys Ala Arg Glu Arg Arg Tyr Tyr Tyr Ser Tyr Gly Met Asp
        115                 120                 125

Val Trp Gly Gln Gly Thr Thr Val Thr Val Ser Ser
    130                 135                 140


<210> SEQ ID NO 13
<211> LENGTH: 420
<212> TYPE: DNA
<213> ORGANISM: Homo sapiens

<400> SEQUENCE: 13

atggagttgg gactgagctg gattttcctt ttggctattt taaaaggtgt ccagtgtgaa      60

gtgcagctgg tggagtctgg gggaggcttg gtacagcctg gcaggtccct gagactctcc     120

tgtgcagcct ctggattcac ctttgatgat tatgccattc actgggtccg gcaagctcca     180

gggaagggcc tggagtgggt ctcaggtatt agttggaatg gtcgtagcat aggctatgcg     240

gactctgtga agggccgatt caccatctcc agagacaacg ccaagaactc cctgtatctg     300

caaatgaaca gtctgagagc tgaggacacg gccttgtatt actgtgcaaa ggatataggc     360

ttctatggtt cggggagcct tgactactgg ggccagggaa ccctggtcac cgtctcctca     420


<210> SEQ ID NO 14
<211> LENGTH: 140
<212> TYPE: PRT
<213> ORGANISM: Homo sapiens

<400> SEQUENCE: 14

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Ile His Trp Val Arg Gln Ala Pro Gly Lys Gly Leu
    50                  55                  60

Glu Trp Val Ser Gly Ile Ser Trp Asn Gly Arg Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gly Phe Tyr Gly Ser Gly Ser Leu Asp
        115                 120                 125

Tyr Trp Gly Gln Gly Thr Leu Val Thr Val Ser Ser
    130                 135                 140


<210> SEQ ID NO 15
<211> LENGTH: 384
<212> TYPE: DNA
<213> ORGANISM: Homo sapiens

<400> SEQUENCE: 15

atggaagccc cagctcagct tctcttcctc ctgctactct ggctcccaga taccaccgga      60

gaaattgtgt tgacacagtc tccagccacc ctgtctttgt ctccagggga aagagccacc     120
```

ctctcctgca gggccagtca gagtgttagc agctacttag cctggtacca acagaaacct 180
ggccaggctc ccaggctcct catctatgat gcatccaaca gggccactgg catcccagcc 240
aggttcagtg gcagtgggtc tgggacagac ttcactctca ccatcagcag cctagagcct 300
gaagattttg cagtttatta ctgtcagcag cgtagcaact ggcctgcgct cactttcggc 360
ggagggacca aggtggagat caaa 384

<210> SEQ ID NO 16
<211> LENGTH: 128
<212> TYPE: PRT
<213> ORGANISM: Homo sapiens

<400> SEQUENCE: 16

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Gln Ser
35 40 45

Val Ser Ser Tyr Leu Ala Trp Tyr Gln Gln Lys Pro Gly Gln Ala Pro
50 55 60

Arg Leu Leu Ile Tyr Asp Ala Ser Asn Arg Ala Thr Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln Gln Arg Ser
100 105 110

Asn Trp Pro Ala Leu Thr Phe Gly Gly Gly Thr Lys Val Glu Ile Lys
115 120 125

<210> SEQ ID NO 17
<211> LENGTH: 5
<212> TYPE: PRT
<213> ORGANISM: Homo sapiens

<400> SEQUENCE: 17

Ser Ser Ala Met Ser
1 5

<210> SEQ ID NO 18
<211> LENGTH: 17
<212> TYPE: PRT
<213> ORGANISM: Homo sapiens

<400> SEQUENCE: 18

Val Ile Ser Ile Ser Gly Gly Ser Thr Tyr Tyr Ala Asp Ser Val Lys
1 5 10 15

Gly

<210> SEQ ID NO 19
<211> LENGTH: 12
<212> TYPE: PRT
<213> ORGANISM: Homo sapiens

<400> SEQUENCE: 19

Glu Thr Arg Tyr Tyr Tyr Ser Tyr Gly Met Asp Val
1 5 10

<210> SEQ ID NO 20
<211> LENGTH: 5
<212> TYPE: PRT
<213> ORGANISM: Homo sapiens

<400> SEQUENCE: 20

Ser Tyr Ser Met Asn
1 5

<210> SEQ ID NO 21
<211> LENGTH: 17
<212> TYPE: PRT
<213> ORGANISM: Homo sapiens

<400> SEQUENCE: 21

Ser Ile Ser Ser Ser Arg Ser Phe Ile Tyr Tyr Ala Asp Ser Val Lys
1 5 10 15

Gly

<210> SEQ ID NO 22
<211> LENGTH: 12
<212> TYPE: PRT
<213> ORGANISM: Homo sapiens

<400> SEQUENCE: 22

Glu Arg Arg Tyr Tyr Tyr Ser Tyr Gly Leu Asp Val
1 5 10

<210> SEQ ID NO 23
<211> LENGTH: 5
<212> TYPE: PRT
<213> ORGANISM: Homo sapiens

<400> SEQUENCE: 23

Ser Tyr Ser Met Asn
1 5

<210> SEQ ID NO 24
<211> LENGTH: 17
<212> TYPE: PRT
<213> ORGANISM: Homo sapiens

<400> SEQUENCE: 24

Ser Ile Ser Ser Ser Ser Ser Tyr Ile Tyr Tyr Ala Asp Ser Val Lys
1 5 10 15

Gly

<210> SEQ ID NO 25
<211> LENGTH: 12
<212> TYPE: PRT
<213> ORGANISM: Homo sapiens

<400> SEQUENCE: 25

Glu Arg Arg Tyr Tyr Tyr Ser Tyr Gly Met Asp Val
1 5 10

<210> SEQ ID NO 26
<211> LENGTH: 5
<212> TYPE: PRT
<213> ORGANISM: Homo sapiens

<400> SEQUENCE: 26

Asp Tyr Ala Ile His
1 5

<210> SEQ ID NO 27
<211> LENGTH: 17
<212> TYPE: PRT
<213> ORGANISM: Homo sapiens

<400> SEQUENCE: 27

Gly Ile Ser Trp Asn Gly Arg Ser Ile Gly Tyr Ala Asp Ser Val Lys
1 5 10 15

Gly

<210> SEQ ID NO 28
<211> LENGTH: 12
<212> TYPE: PRT
<213> ORGANISM: Homo sapiens

<400> SEQUENCE: 28

Asp Ile Gly Phe Tyr Gly Ser Gly Ser Leu Asp Tyr
1 5 10

<210> SEQ ID NO 29
<211> LENGTH: 11
<212> TYPE: PRT
<213> ORGANISM: Homo sapiens

<400> SEQUENCE: 29

Arg Ala Ser Gln Arg Ile Gly Phe Ala Leu Ala
1 5 10

<210> SEQ ID NO 30
<211> LENGTH: 7
<212> TYPE: PRT
<213> ORGANISM: Homo sapiens

<400> SEQUENCE: 30

Asp Ala Ser Ser Leu Glu Thr
1 5

<210> SEQ ID NO 31
<211> LENGTH: 9
<212> TYPE: PRT
<213> ORGANISM: Homo sapiens

<400> SEQUENCE: 31

Gln Gln Phe Asn Thr Tyr Pro Phe Thr
1 5

<210> SEQ ID NO 32
<211> LENGTH: 11
<212> TYPE: PRT
<213> ORGANISM: Homo sapiens

<400> SEQUENCE: 32

Arg Ala Ser Gln Gly Ile Ser Ser Ala Leu Ala
1 5 10

<210> SEQ ID NO 33
<211> LENGTH: 7
<212> TYPE: PRT
<213> ORGANISM: Homo sapiens

<400> SEQUENCE: 33

Asp Ala Ser Ser Leu Glu Ser
1 5

<210> SEQ ID NO 34
<211> LENGTH: 9
<212> TYPE: PRT
<213> ORGANISM: Homo sapiens

<400> SEQUENCE: 34

Gln Gln Phe Asn Ser Tyr Pro Tyr Thr
1               5

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Ala Leu Ala
1               5                   10

<210> SEQ ID NO 36
<211> LENGTH: 7
<212> TYPE: PRT
<213> ORGANISM: Homo sapiens

<400> SEQUENCE: 36

Asp Ala Ser Ser Leu Glu Ser
1               5

<210> SEQ ID NO 37
<211> LENGTH: 9
<212> TYPE: PRT
<213> ORGANISM: Homo sapiens

<400> SEQUENCE: 37

Gln Gln Phe Asn Ser Tyr Pro Tyr Thr
1               5

<210> SEQ ID NO 38
<211> LENGTH: 11
<212> TYPE: PRT
<213> ORGANISM: Homo sapiens

<400> SEQUENCE: 38

Arg Ala Ser Gln Ser Val Ser Ser Tyr Leu Ala
1               5                   10

<210> SEQ ID NO 39
<211> LENGTH: 7
<212> TYPE: PRT
<213> ORGANISM: Homo sapiens

<400> SEQUENCE: 39

Asp Ala Ser Asn Arg Ala Thr
1               5

<210> SEQ ID NO 40
<211> LENGTH: 10
<212> TYPE: PRT
<213> ORGANISM: Homo sapiens

<400> SEQUENCE: 40

Gln Gln Arg Ser Asn Trp Pro Ala Leu Thr
1               5                   10

<210> SEQ ID NO 41
<211> LENGTH: 312
<212> TYPE: PRT
<213> ORGANISM: Poxvirus

<400> SEQUENCE: 41

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Ile Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Lys Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Lys Gly Gly Arg Ala Asp Pro Ala Phe Leu Tyr Lys Val
        275                 280                 285

Val Arg Met Asn Glu Asp Leu Gly Lys Pro Ile Pro Asn Pro Leu Leu
    290                 295                 300

Gly Leu Asp Ser Thr Arg Thr Gly
305                 310
```

<210> SEQ ID NO 42
<211> LENGTH: 317
<212> TYPE: PRT
<213> ORGANISM: Poxvirus

<400> SEQUENCE: 42

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
```

```
            20                  25                  30

Ser Thr Glu Thr Ser Phe Asn Asn Asn Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240

Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315
```

<210> SEQ ID NO 43
<211> LENGTH: 317
<212> TYPE: PRT
<213> ORGANISM: Poxvirus

<400> SEQUENCE: 43

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80
```

```
Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240

Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 44
<211> LENGTH: 317
<212> TYPE: PRT
<213> ORGANISM: Poxvirus

<400> SEQUENCE: 44

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asn Asn Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140
```

```
Glu Lys Tyr Ser Phe Gly Glu Tyr Ile Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Lys Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 45
<211> LENGTH: 317
<212> TYPE: PRT
<213> ORGANISM: Poxvirus

<400> SEQUENCE: 45

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Ile Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
```

```
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Lys Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 46
<211> LENGTH: 317
<212> TYPE: PRT
<213> ORGANISM: Poxvirus

<400> SEQUENCE: 46

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240

Asn Glu Glu Phe Asp Pro Val Asp Asp Gly Pro Asp Asp Glu Thr Asp
                245                 250                 255
```

```
Leu Ser Lys Leu Ser Lys Asp Val Val Gln Tyr Glu Gln Glu Ile Glu
            260                 265                 270

Ser Leu Glu Ala Thr Tyr His Ile Ile Met Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 47
<211> LENGTH: 317
<212> TYPE: PRT
<213> ORGANISM: Poxvirus

<400> SEQUENCE: 47

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Ser Gly Tyr Tyr Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ala Thr
                85                  90                  95

Ile Thr Leu Ile Cys Lys Asp Glu Thr Lys Tyr Phe Arg Cys Glu Glu
            100                 105                 110

Lys Asn Glu Asn Thr Ser Trp Asn Asp Thr Val Thr Cys Pro Asn Ala
        115                 120                 125

Glu Cys Gln Ser Leu Gln Leu Glu His Gly Ser Cys Gln Pro Val Lys
    130                 135                 140

Glu Lys Tyr Ser Phe Gly Glu His Ile Thr Ile Asn Cys Asp Val Gly
145                 150                 155                 160

Tyr Glu Val Ile Gly Ala Ser Tyr Ile Ser Cys Thr Ala Asn Ser Arg
                165                 170                 175

Asn Ile Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Ser Ser Ser Thr
    210                 215                 220

Cys Ile Asp Gly Lys Trp Asn Pro Val Leu Pro Ile Cys Val Arg Ser
225                 230                 235                 240

Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Val Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asn Gln Tyr Lys Phe His Lys Leu Leu Pro
305                 310                 315
```

<210> SEQ ID NO 48
<211> LENGTH: 317
<212> TYPE: PRT
<213> ORGANISM: Poxvirus

<400> SEQUENCE: 48

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Ser Gly Tyr Tyr Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asn Lys Pro Leu Tyr Glu Val Asn Ala Ile
                85                  90                  95

Ile Thr Leu Ile Cys Lys Asp Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Gly Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240

Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asp Gln Tyr Lys Phe His Lys Leu Leu Leu
305                 310                 315
```

<210> SEQ ID NO 49
<211> LENGTH: 317
<212> TYPE: PRT
<213> ORGANISM: Poxvirus

<400> SEQUENCE: 49

```
Met Lys Thr Ile Ser Val Val Thr Leu Leu Cys Val Leu Pro Ala Val
1               5                   10                  15
```

Val Tyr Ser Thr Cys Thr Val Pro Thr Met Asn Asn Ala Lys Leu Thr
20 25 30

Ser Thr Glu Thr Ser Phe Asn Asp Lys Gln Lys Val Thr Phe Thr Cys
35 40 45

Asp Ser Gly Tyr Tyr Ser Leu Asp Pro Asn Ala Val Cys Glu Thr Asp
50 55 60

Lys Trp Lys Tyr Glu Asn Pro Cys Lys Lys Met Cys Thr Val Ser Asp
65 70 75 80

Tyr Val Ser Glu Leu Tyr Asn Lys Pro Leu Tyr Glu Val Asn Ala Ile
85 90 95

Ile Thr Leu Ile Cys Lys Asp Glu Thr Lys Tyr Phe Arg Cys Glu Glu
100 105 110

Lys Asn Gly Asn Thr Ser Trp Asn Asp Thr Val Thr Cys Pro Asn Ala
115 120 125

Glu Cys Gln Ser Leu Gln Leu Asp His Gly Ser Cys Gln Pro Val Lys
130 135 140

Glu Lys Tyr Ser Phe Gly Glu His Ile Thr Ile Asn Cys Asp Val Gly
145 150 155 160

Tyr Glu Val Ile Gly Ala Ser Tyr Ile Thr Cys Thr Ala Asn Ser Trp
165 170 175

Asn Val Ile Pro Ser Cys Gln Gln Lys Cys Asp Ile Pro Ser Leu Ser
180 185 190

Asn Gly Leu Ile Ser Gly Ser Thr Phe Ser Ile Gly Gly Val Ile His
195 200 205

Leu Ser Cys Lys Ser Gly Phe Ile Leu Thr Gly Ser Pro Ser Ser Thr
210 215 220

Cys Ile Asp Gly Lys Trp Asn Pro Val Leu Pro Ile Cys Ile Arg Ser
225 230 235 240

Asn Glu Glu Phe Asp Pro Val Glu Asp Gly Pro Asp Asp Glu Thr Asp
245 250 255

Leu Ser Lys Leu Ser Lys Asp Val Val Gln Tyr Glu Gln Glu Ile Glu
260 265 270

Ser Leu Glu Ala Thr Tyr His Ile Ile Ile Val Ala Leu Thr Ile Met
275 280 285

Gly Val Ile Phe Leu Ile Ser Val Ile Val Leu Val Cys Ser Cys Asn
290 295 300

Lys Asn Asn Asp Gln Tyr Lys Phe His Lys Leu Leu Leu
305 310 315

<210> SEQ ID NO 50
<211> LENGTH: 316
<212> TYPE: PRT
<213> ORGANISM: Poxvirus

<400> SEQUENCE: 50

Met Lys Thr Ile Ser Val Val Thr Leu Leu Cys Val Leu Pro Ala Val
1 5 10 15

Val Tyr Ser Thr Cys Thr Val Pro Thr Met Asn Asn Ala Lys Leu Thr
20 25 30

Ser Thr Glu Thr Ser Phe Asn Asp Lys Gln Lys Val Thr Phe Thr Cys
35 40 45

Asp Ser Gly Tyr Tyr Ser Leu Asp Pro Asn Ala Val Cys Glu Thr Asp
50 55 60

Lys Trp Lys Tyr Glu Asn Pro Cys Lys Lys Met Cys Thr Val Ser Asp

```
65                  70                  75                  80

Tyr Val Ser Glu Leu Tyr Asn Lys Pro Leu Tyr Glu Val Asn Ala Ile
                85                  90                  95

Ile Thr Leu Ile Cys Lys Asp Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Glu Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240

Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asp Gln Tyr Lys Phe His Lys Leu Leu
305                 310                 315


<210> SEQ ID NO 51
<211> LENGTH: 317
<212> TYPE: PRT
<213> ORGANISM: Poxvirus

<400> SEQUENCE: 51

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Ser Gly Tyr His Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125
```

```
Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Val Ser Tyr Ile Ser Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Met Ala Leu Thr Ile Met
        275                 280                 285

Gly Val Ile Phe Leu Ile Ser Ile Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 52
<211> LENGTH: 317
<212> TYPE: PRT
<213> ORGANISM: Poxvirus

<400> SEQUENCE: 52

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Ile Pro Ser Leu Ser
            180                 185                 190
```

```
Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Glu Phe Asp Leu Val Asp Asp Gly Pro Asp Asp Glu Thr Asp
                245                 250                 255

Leu Ser Lys Ile Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Ile Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 53
<211> LENGTH: 324
<212> TYPE: PRT
<213> ORGANISM: Poxvirus

<400> SEQUENCE: 53

Met Ala Ala Val Lys Thr Pro Val Ile Val Val Pro Val Ile Asp Arg
1               5                   10                  15

Pro Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asn
        35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Thr Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
```

```
                245                 250                 255

Trp Ser Arg Ile Gly Thr Ala Ala Ala Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile


<210> SEQ ID NO 54
<211> LENGTH: 324
<212> TYPE: PRT
<213> ORGANISM: Poxvirus

<400> SEQUENCE: 54

Met Ala Ala Ala Lys Thr Pro Val Ile Val Val Pro Val Ile Asp Arg
1               5                   10                  15

Leu Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asn
        35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Thr Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
```

290 295 300

Phe Asn Val Lys Ser Lys Leu Leu Trp Phe Leu Thr Gly Thr Phe Val
305 310 315 320

Thr Ala Phe Ile

<210> SEQ ID NO 55
<211> LENGTH: 324
<212> TYPE: PRT
<213> ORGANISM: Poxvirus

<400> SEQUENCE: 55

Met Ala Ala Val Lys Thr Pro Val Ile Val Val Pro Val Ile Asp Arg
1 5 10 15

Pro Pro Ser Glu Thr Phe Pro Asn Val His Glu His Ile Asn Asp Gln
20 25 30

Lys Phe Asp Asp Val Lys Asp Asn Glu Val Met Pro Glu Lys Arg Asn
35 40 45

Val Val Val Val Lys Asp Asp Pro Asp His Tyr Lys Asp Tyr Ala Phe
50 55 60

Ile Gln Trp Thr Gly Gly Asn Ile Arg Asn Asp Asp Lys Tyr Thr His
65 70 75 80

Phe Phe Ser Gly Phe Cys Asn Thr Met Cys Thr Glu Glu Thr Lys Arg
85 90 95

Asn Ile Ala Arg His Leu Ala Leu Trp Asp Ser Asn Phe Phe Thr Glu
100 105 110

Leu Glu Asn Lys Lys Val Glu Tyr Val Val Ile Val Glu Asn Asp Asn
115 120 125

Val Ile Glu Asp Ile Thr Phe Leu Arg Pro Val Leu Lys Ala Met His
130 135 140

Asp Lys Lys Ile Asp Ile Leu Gln Met Arg Glu Ile Ile Thr Gly Asn
145 150 155 160

Lys Val Lys Thr Glu Leu Val Met Asp Lys Asn His Ala Ile Phe Thr
165 170 175

Tyr Thr Gly Gly Tyr Asp Val Ser Leu Ser Ala Tyr Ile Ile Arg Val
180 185 190

Thr Thr Ala Leu Asn Ile Val Asp Glu Ile Ile Lys Ser Gly Gly Leu
195 200 205

Ser Ser Gly Phe Tyr Phe Glu Ile Ala Arg Ile Glu Asn Glu Met Lys
210 215 220

Ile Asn Arg Gln Ile Leu Asp Asn Ala Ala Lys Tyr Val Glu His Asp
225 230 235 240

Pro Arg Leu Val Ala Glu Tyr Arg Phe Glu Asn Met Lys Pro Asn Phe
245 250 255

Trp Ser Arg Ile Gly Thr Ala Ala Ala Lys Arg Tyr Pro Gly Val Met
260 265 270

Tyr Ala Phe Thr Thr Pro Leu Ile Ser Phe Phe Gly Leu Phe Asp Ile
275 280 285

Asn Val Ile Gly Leu Ile Val Ile Leu Phe Ile Met Phe Met Leu Ile
290 295 300

Phe Asn Val Lys Ser Lys Leu Leu Trp Phe Leu Thr Gly Thr Phe Val
305 310 315 320

Thr Ala Phe Ile

<210> SEQ ID NO 56

-continued

<211> LENGTH: 324
<212> TYPE: PRT
<213> ORGANISM: Poxvirus

<400> SEQUENCE: 56

```
Met Ala Ala Val Lys Thr Pro Val Ile Val Val Pro Val Ile Asp Arg
1               5                   10                  15

Pro Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asn
        35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu Tyr Arg Phe Glu Asn Met Lys Pro Asn Phe
                245                 250                 255

Trp Ser Arg Ile Gly Thr Ala Ala Ala Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile
```

<210> SEQ ID NO 57
<211> LENGTH: 324
<212> TYPE: PRT
<213> ORGANISM: Poxvirus

<400> SEQUENCE: 57

```
Met Ala Ala Ala Lys Thr Pro Val Ile Val Val Pro Val Ile Asp Arg
1               5                   10                  15
```

```
Leu Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asn
        35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Glu Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Thr Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile
```

<210> SEQ ID NO 58
<211> LENGTH: 324
<212> TYPE: PRT
<213> ORGANISM: Poxvirus

<400> SEQUENCE: 58

```
Met Ala Ala Ala Lys Thr Pro Val Ile Val Val Pro Val Ile Asp Arg
1               5                   10                  15

Pro Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asp
        35                  40                  45

Val Val Val Val Lys Asp Asp Pro Asp His Tyr Lys Asp Tyr Ala Phe
    50                  55                  60
```

-continued

```
Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Lys Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asp His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Ala Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile


<210> SEQ ID NO 59
<211> LENGTH: 325
<212> TYPE: PRT
<213> ORGANISM: Poxvirus

<400> SEQUENCE: 59

Met Ala Thr Val Asn Lys Thr Pro Val Ile Val Val Pro Val Ile Asp
1               5                   10                  15

Arg Pro Pro Ser Glu Thr Phe Pro Asn Leu His Glu His Ile Asn Asp
            20                  25                  30

Gln Lys Phe Asp Asp Val Lys Asp Asn Glu Val Met Pro Glu Lys Arg
        35                  40                  45

Asn Val Val Ile Val Lys Asp Asp Pro Asp His Tyr Lys Asp Tyr Ala
    50                  55                  60

Phe Ile His Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110
```

Glu Leu Glu Asn Lys Lys Val Glu Tyr Val Val Ile Val Glu Asn Asp
115 120 125

Asn Val Ile Glu Asp Ile Thr Phe Leu Arg Pro Val Leu Lys Ala Met
130 135 140

His Asp Lys Lys Ile Asp Ile Leu Gln Met Arg Glu Ile Ile Thr Gly
145 150 155 160

Asn Lys Val Lys Thr Glu Leu Val Met Asp Lys Asn His Val Ile Phe
165 170 175

Thr Tyr Thr Gly Gly Tyr Asp Val Ser Leu Ser Ala Tyr Ile Ile Arg
180 185 190

Val Thr Thr Ala Leu Asn Ile Val Asp Glu Ile Ile Lys Ser Gly Gly
195 200 205

Leu Ser Ser Gly Phe Tyr Phe Glu Ile Ala Arg Ile Glu Asn Glu Met
210 215 220

Lys Ile Asn Arg Gln Ile Met Asp Asn Ser Ala Lys Tyr Val Glu His
225 230 235 240

Asp Pro Arg Leu Val Ala Glu His Arg Phe Glu Asn Met Lys Pro Asn
245 250 255

Phe Trp Ser Arg Ile Gly Thr Ala Ala Val Lys Arg Tyr Pro Gly Val
260 265 270

Met Tyr Ala Phe Thr Thr Pro Leu Ile Ser Phe Phe Gly Leu Phe Asp
275 280 285

Ile Asn Val Ile Gly Leu Ile Val Ile Leu Phe Ile Met Phe Met Leu
290 295 300

Ile Phe Asn Val Lys Ser Lys Leu Leu Trp Phe Leu Thr Gly Thr Phe
305 310 315 320

Val Thr Ala Phe Ile
325

<210> SEQ ID NO 60
<211> LENGTH: 325
<212> TYPE: PRT
<213> ORGANISM: Poxvirus

<400> SEQUENCE: 60

Met Ala Thr Val Asn Lys Thr Pro Val Ile Val Val Pro Val Ile Asp
1 5 10 15

Arg Pro Pro Ser Glu Thr Phe Pro Asn Leu His Glu His Ile Asn Asp
20 25 30

Gln Lys Phe Asp Asp Val Lys Asp Asn Glu Val Met Pro Glu Lys Arg
35 40 45

Asn Val Val Ile Val Lys Asp Asp Pro Asp His Tyr Lys Asp Tyr Ala
50 55 60

Phe Ile His Trp Thr Gly Gly Asn Ile Arg Asn Asp Asp Lys Tyr Thr
65 70 75 80

His Phe Phe Ser Gly Phe Cys Asn Thr Met Cys Thr Glu Glu Thr Lys
85 90 95

Arg Asn Ile Ala Arg His Leu Ala Leu Trp Asp Ser Lys Phe Phe Thr
100 105 110

Glu Leu Glu Asn Lys Lys Val Glu Tyr Val Val Ile Val Glu Asn Asp
115 120 125

Asn Val Ile Glu Asp Ile Thr Phe Leu Arg Pro Val Leu Lys Ala Met
130 135 140

His Asp Lys Lys Ile Asp Ile Leu Gln Met Arg Glu Ile Ile Thr Gly
145 150 155 160

Asn Lys Val Lys Thr Glu Leu Val Met Asp Lys Asn His Val Ile Phe
165 170 175

Thr Tyr Thr Gly Gly Tyr Asp Val Ser Leu Ser Ala Tyr Ile Ile Arg
180 185 190

Val Thr Thr Ala Leu Asn Ile Val Asp Glu Ile Ile Lys Ser Gly Gly
195 200 205

Leu Ser Ser Gly Phe Tyr Phe Glu Ile Ala Arg Ile Glu Asn Glu Ile
210 215 220

Lys Ile Asn Arg Gln Ile Met Asp Asn Ser Ala Lys Tyr Val Glu His
225 230 235 240

Asp Pro Arg Leu Val Ala Glu His Arg Phe Glu Asn Met Lys Pro Asn
245 250 255

Phe Trp Ser Arg Ile Gly Thr Ala Ala Val Lys Arg Tyr Pro Gly Val
260 265 270

Met Tyr Ala Phe Thr Thr Pro Leu Ile Ser Phe Phe Gly Leu Phe Asp
275 280 285

Ile Asn Val Ile Gly Leu Ile Val Ile Leu Phe Ile Met Phe Met Leu
290 295 300

Ile Phe Asn Val Lys Ser Lys Leu Leu Trp Phe Leu Thr Gly Thr Phe
305 310 315 320

Val Thr Ala Phe Ile
325

<210> SEQ ID NO 61
<211> LENGTH: 325
<212> TYPE: PRT
<213> ORGANISM: Poxvirus

<400> SEQUENCE: 61

Met Ala Ala Val Asn Lys Thr Pro Val Ile Val Val Pro Val Ile Asp
1 5 10 15

Arg Pro Pro Ser Glu Thr Phe Pro Asn Leu His Glu His Ile Asn Asp
20 25 30

Gln Lys Phe Asp Asp Val Lys Asp Asn Glu Val Met Pro Glu Lys Arg
35 40 45

Asn Val Val Ile Val Lys Asp Asp Pro Asp His Tyr Lys Asp Tyr Ala
50 55 60

Phe Ile His Trp Thr Gly Gly Asn Ile Arg Asn Asp Asp Lys Tyr Thr
65 70 75 80

His Phe Phe Ser Gly Phe Cys Asn Thr Met Cys Thr Glu Glu Thr Lys
85 90 95

Arg Asn Ile Ala Arg His Leu Ala Leu Trp Asp Ser Lys Phe Phe Thr
100 105 110

Glu Leu Glu Asn Lys Lys Val Glu Tyr Val Val Ile Val Glu Asn Asp
115 120 125

Asn Val Ile Glu Asp Ile Thr Phe Leu Arg Pro Val Leu Lys Ala Met
130 135 140

His Asp Lys Lys Ile Asp Ile Leu Gln Met Arg Glu Ile Ile Thr Gly
145 150 155 160

Asn Lys Val Lys Thr Glu Leu Val Met Asp Lys Asn His Val Ile Phe
165 170 175

Thr Tyr Thr Gly Gly Tyr Asp Val Ser Leu Ser Ala Tyr Ile Ile Arg
180 185 190

Val Thr Thr Ala Leu Asn Ile Val Asp Glu Ile Ile Lys Ser Gly Gly

```
        195                 200                 205

Leu Ser Ser Gly Phe Tyr Phe Glu Ile Ala Arg Ile Glu Asn Glu Met
    210                 215                 220

Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
                245                 250                 255

Phe Trp Ser Arg Ile Gly Thr Ala Ala Val Lys Arg Tyr Pro Gly Val
            260                 265                 270

Met Tyr Ala Phe Thr Thr Pro Leu Ile Ser Phe Phe Gly Leu Phe Asp
        275                 280                 285

Ile Asn Val Ile Gly Leu Ile Val Ile Leu Phe Ile Met Phe Met Leu
    290                 295                 300

Ile Phe Asn Val Lys Ser Lys Leu Leu Trp Phe Leu Thr Gly Thr Phe
305                 310                 315                 320

Val Thr Ala Phe Ile
                325


<210> SEQ ID NO 62
<211> LENGTH: 325
<212> TYPE: PRT
<213> ORGANISM: Poxvirus

<400> SEQUENCE: 62

Met Ala Ala Val Asn Arg Thr Pro Val Ile Val Val Pro Val Ile Asp
1               5                   10                  15

Arg His Pro Ser Glu Thr Phe Pro Asn Val His Glu His Ile Asn Asp
            20                  25                  30

Gln Lys Phe Asp Asp Val Lys Asp Asn Glu Val Met Pro Glu Lys Arg
        35                  40                  45

Asp Val Val Ile Val Lys Asp Asp Pro Asp His Tyr Lys Asp Tyr Ala
    50                  55                  60

Phe Ile Gln Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110

Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn Tyr Ala Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Met
    210                 215                 220

Lys Ile Asn Arg Gln Ile Met Asp Asn Ser Ala Lys Tyr Val Glu His
225                 230                 235                 240
```

-continued

Asp Pro Arg Leu Val Ala Glu His Arg Phe Glu Asn Met Lys Pro Asn
                245                 250                 255

Phe Trp Ser Arg Ile Gly Thr Ala Ala Ala Lys Arg Tyr Pro Gly Val
            260                 265                 270

Met Tyr Ala Phe Thr Thr Pro Leu Ile Ser Phe Phe Gly Leu Phe Asp
        275                 280                 285

Ile Asn Val Ile Gly Leu Ile Val Ile Leu Phe Ile Met Phe Met Leu
    290                 295                 300

Ile Phe Asn Val Lys Ser Lys Leu Leu Trp Phe Leu Thr Gly Thr Phe
305                 310                 315                 320

Val Thr Ala Phe Ile
                325

<210> SEQ ID NO 63
<211> LENGTH: 324
<212> TYPE: PRT
<213> ORGANISM: Poxvirus

<400> SEQUENCE: 63

Met Ala Ala Ala Lys Thr Pro Val Ile Val Val Pro Val Ile Asp Arg
1               5                   10                  15

Pro Pro Ser Glu Thr Phe Pro Asn Val His Glu His Ile Asn Asp Gln
            20                  25                  30

Lys Phe Asp Asp Val Lys Asp Asn Glu Val Met Gln Glu Lys Arg Asp
        35                  40                  45

Val Val Ile Val Asn Asp Asp Pro Asp His Tyr Lys Asp Tyr Val Phe
    50                  55                  60

Ile Gln Trp Thr Gly Gly Asn Ile Arg Asp Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Lys Phe Phe Ile Glu
            100                 105                 110

Leu Glu Asn Lys Asn Val Glu Tyr Val Val Ile Ile Glu Asn Asp Asn
        115                 120                 125

Val Ile Glu Asp Ile Thr Phe Leu Arg Pro Val Leu Lys Ala Ile His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Ile Asp Lys Asp His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Met Asp Asn Ser Ala Lys Tyr Val Glu His Asp
225                 230                 235                 240

Pro Arg Leu Val Ala Glu His Arg Phe Glu Thr Met Lys Pro Asn Phe
                245                 250                 255

Trp Ser Arg Ile Gly Thr Val Ala Ala Lys Arg Tyr Pro Gly Val Met
            260                 265                 270

Tyr Thr Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
290 295 300

Phe Asn Val Lys Ser Lys Leu Leu Trp Phe Leu Thr Gly Thr Phe Val
305 310 315 320

Thr Ala Phe Ile

<210> SEQ ID NO 64
<211> LENGTH: 324
<212> TYPE: PRT
<213> ORGANISM: Poxvirus

<400> SEQUENCE: 64

Met Ala Ala Ala Lys Thr Pro Val Ile Val Val Pro Val Ile Asp Arg
1 5 10 15

Pro Pro Ser Glu Thr Phe Pro Asn Val His Glu His Ile Asn Asp Gln
20 25 30

Lys Phe Asp Asp Val Lys Asp Asn Glu Val Met Pro Glu Lys Arg Asp
35 40 45

Val Val Val Val Lys Asp Asp Pro Asp His Tyr Lys Asp Tyr Ala Phe
50 55 60

Ile Gln Trp Thr Gly Gly Asn Ile Arg Asn Asp Asp Lys Tyr Thr His
65 70 75 80

Phe Phe Ser Gly Phe Cys Asn Thr Met Cys Thr Glu Glu Thr Lys Arg
85 90 95

Asn Ile Ala Arg His Leu Ala Leu Trp Asp Ser Lys Phe Phe Thr Glu
100 105 110

Leu Glu Asn Lys Lys Val Glu Tyr Val Val Ile Val Glu Asn Asp Asn
115 120 125

Val Ile Glu Asp Ile Thr Phe Leu Arg Pro Val Leu Lys Ala Met His
130 135 140

Asp Lys Lys Ile Asp Ile Leu Gln Met Arg Glu Ile Ile Thr Gly Asn
145 150 155 160

Lys Val Lys Thr Glu Leu Val Met Asp Lys Asp His Ala Ile Phe Thr
165 170 175

Tyr Thr Gly Gly Tyr Asp Val Ser Leu Ser Ala Tyr Ile Ile Arg Val
180 185 190

Thr Thr Ala Leu Asn Ile Val Asp Glu Ile Ile Lys Ser Gly Gly Leu
195 200 205

Ser Ser Gly Phe Tyr Phe Glu Ile Ala Arg Ile Glu Asn Glu Met Lys
210 215 220

Ile Asn Arg Gln Ile Leu Asp Asn Ala Ala Lys Tyr Val Glu His Asp
225 230 235 240

Pro Arg Leu Val Ala Glu His Arg Phe Glu Asn Met Lys Pro Asn Phe
245 250 255

Trp Ser Arg Ile Gly Thr Ala Ala Ala Lys Arg Tyr Pro Gly Val Met
260 265 270

Tyr Ala Phe Thr Thr Pro Leu Ile Ser Phe Phe Gly Leu Phe Asp Ile
275 280 285

Asn Val Ile Gly Leu Ile Val Ile Leu Phe Ile Met Phe Met Leu Ile
290 295 300

Phe Asn Val Lys Ser Lys Leu Leu Trp Phe Leu Thr Gly Thr Phe Val
305 310 315 320

Thr Ala Phe Ile

<210> SEQ ID NO 65
<211> LENGTH: 298
<212> TYPE: PRT
<213> ORGANISM: Poxvirus

<400> SEQUENCE: 65

```
Met Ala Glu Ser Glu Ser Thr Ile Pro Leu Tyr Val Leu Pro Val Val
1               5                   10                  15

Gly Arg Gly Ala Ala Glu Val Val Pro Gly Asn Lys Ser Thr Gly Thr
            20                  25                  30

Val Arg Val Ser Gln Trp Thr Pro Gly Gly Ala Lys Ser Glu Gln Ala
        35                  40                  45

Gly Gln Tyr Tyr Ser Ala Leu Cys Arg Val Leu Cys Ser Ala Glu Ala
    50                  55                  60

Lys Gln Thr Ile Leu Asn His Leu Ser Leu Trp Lys Glu Leu Gly Ser
65                  70                  75                  80

Glu Ser Ala Pro Lys Ala Ala Gly Ala Glu Ser Glu Tyr Ala Ile Val
                85                  90                  95

Val Glu Asp Asp Asn Thr Val Gln Pro Leu Leu Leu Gln Ser Ala Ala
            100                 105                 110

Ala Leu Val Gly Gly Met Arg Ala Gln Gln Val His Val Leu Gln Leu
        115                 120                 125

Arg Glu Pro Leu His Ala Gly Val Arg Ala Gln Thr Pro Leu Ser Gly
    130                 135                 140

Asn Pro Ser Ala Tyr Val Tyr Pro Ala Arg Leu His Ala Ser Leu Gly
145                 150                 155                 160

Ala Tyr Ile Ile His Lys Pro Ser Ala Gly Arg Leu His Ala Glu Phe
                165                 170                 175

Leu Arg Ser Arg Val Thr Ala Gly Leu Pro Leu Glu Leu Pro Arg Val
            180                 185                 190

Glu Arg Ala Gln Gly Leu Thr Arg Met Val Leu Ala Gly Ser Ser Glu
        195                 200                 205

Tyr Val Thr His Glu Tyr Arg Leu Arg Asn Glu Leu Arg Gly Arg Glu
    210                 215                 220

Tyr Gly Ala Ser Leu Arg Ala Arg Ala Gly Ala Trp Leu Ala Arg Asn
225                 230                 235                 240

Tyr Pro Gln Ala Tyr Ala Ala Ala Thr Thr Pro Val Phe Ser Leu Phe
                245                 250                 255

Gly Arg Val Asp Val Asn Val Phe Gly Val Leu Ser Val Leu Phe Val
            260                 265                 270

Leu Val Leu Val Val Phe Asp Val Gln Ser Arg Leu Ala Trp Leu Leu
        275                 280                 285

Val Gly Ala Leu Ala Ser Gly Leu Leu Gln
    290                 295
```

<210> SEQ ID NO 66
<211> LENGTH: 50
<212> TYPE: PRT
<213> ORGANISM: Poxvirus

<400> SEQUENCE: 66

```
Asp Gln Lys Phe Asp Asp Val Lys Asp Asn Glu Val Met Pro Glu Lys
1               5                   10                  15

Arg Asn Val Val Val Val Lys Asp Asp Pro Asp His Tyr Lys Asp Tyr
            20                  25                  30
```

Ala Phe Ile Gln Trp Thr Gly Gly Asn Ile Arg Asn Asp Asp Lys Tyr
35 40 45

Thr His
50

<210> SEQ ID NO 67
<211> LENGTH: 47
<212> TYPE: PRT
<213> ORGANISM: Poxvirus

<400> SEQUENCE: 67

Thr Glu Glu Thr Lys Arg Asn Ile Ala Arg His Leu Ala Leu Trp Asp
1 5 10 15

Ser Asn Phe Phe Thr Glu Leu Glu Asn Lys Lys Val Glu Tyr Val Val
20 25 30

Ile Val Glu Asn Asp Asn Val Ile Glu Asp Ile Thr Phe Leu Arg
35 40 45

<210> SEQ ID NO 68
<211> LENGTH: 40
<212> TYPE: PRT
<213> ORGANISM: Poxvirus

<400> SEQUENCE: 68

Lys Ala Met His Asp Lys Lys Ile Asp Ile Leu Gln Met Arg Glu Ile
1 5 10 15

Ile Thr Gly Asn Lys Val Lys Thr Glu Leu Val Met Asp Lys Asn His
20 25 30

Thr Ile Phe Thr Tyr Thr Gly Gly
35 40

<210> SEQ ID NO 69
<211> LENGTH: 957
<212> TYPE: DNA
<213> ORGANISM: Artificial Sequence
<220> FEATURE:
<223> OTHER INFORMATION: Description of Artifical Sequence: Poxvirus chimera

<400> SEQUENCE: 69
atgaaaacga tttccgttgt tacgttgtta tgcgtactac ctgctgttgt ttattcaaca 60
tgtactgtac ccactatgaa taacgctaaa ttaacgtcta ccgaaacatc gtttaatgat 120
aaacagaaag ttacatttac atgtgatcag ggatatcatt cttcggatcc aaatgctgtc 180
tgtgaaacag ataaatggaa atacgaaaat ccatgcaaga aaatgtgcac agtttctgat 240
tatgtctctg aattatatga taagccatta tacgaagtga attccaccat gacactaagt 300
tgcaacggcg aaacaaaata ttttcgttgc gaagaaaaaa atggaaatac ttcttggaat 360
gatactgtta cgtgtcctaa tgcggaatgt caacctcttc aattagaaca cggatcgtgt 420
caaccagtta aagaaaaata ctcatttggg gaatatataa ctatcaactg tgatgttgga 480
tatgaggtta ttggtgcttc gtacataagt tgtacagcta attcttggaa tgttattcca 540
tcatgtcaac aaaaatgtga tatgccgtct ctatctaacg gattaatttc cggatctaca 600
ttttctatcg gtggcgttat acatcttagt tgtaaaagtg gttttacact aacggggtct 660
ccatcatcca catgtatcga cggtaaatgg aatcccatac tcccaacatg tgtacgatct 720
aacgaaaaat ttgatccagt ggatgatggt cccgacgatg agacagattt gagcaaactc 780
tcgaaagacg ttgtacaata tgaacaagaa atagaatcgt tagaaaaggg tgggcgcgcc 840

-continued

```
gacccagctt tcttgtacaa agtggtgaga atgaatgaag atctggggaa gcctatccct    900

aaccctctcc tcggtctcga ttctacgcgt accggtcatc atcaccatca ccattga       957


<210> SEQ ID NO 70
<211> LENGTH: 318
<212> TYPE: PRT
<213> ORGANISM: Artificial Sequence
<220> FEATURE:
<223> OTHER INFORMATION: Description of Artifical Sequence: Poxvirus
      chimera

<400> SEQUENCE: 70

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asp Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Ile Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Glu Lys Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Lys Gly Gly Arg Ala Asp Pro Ala Phe Leu Tyr Lys Val
        275                 280                 285

Val Arg Met Asn Glu Asp Leu Gly Lys Pro Ile Pro Asn Pro Leu Leu
    290                 295                 300

Gly Leu Asp Ser Thr Arg Thr Gly His His His His His His
305                 310                 315


<210> SEQ ID NO 71
<211> LENGTH: 1005
<212> TYPE: DNA
```

<213> ORGANISM: Artificial Sequence
<220> FEATURE:
<223> OTHER INFORMATION: Description of Artifical Sequence: Poxvirus chimera

<400> SEQUENCE: 71

```
atggctagcg cggcggcgaa aactcctgtt attgttgtgc cagttattga tagacttcca     60

tcagaaacat ttcctaatgt tcatgagcat attaatgatc agaagttcga tgatgtaaag    120

gacaacgaag ttatgccaga aaaaagaaat gttgtggtag tcaaggatga tccagatcat    180

tacaaggatt atgcgtttat acagtggact ggaggaaaca ttagaaatga tgacaagtat    240

actcacttct tttcagggtt ttgtaacact atgtgtacag aggaaacgaa aagaaatatc    300

gctagacatt tagccctatg ggattctaat ttttttaccg agttagaaaa taaaaaggta    360

gaatatgtag ttattgtaga aaacgataac gttattgagg atattacgtt tcttcgtccc    420

gtcttgaagg caatgcatga caaaaaaata gatatcctac agatgagaga aattattaca    480

ggcaataaag ttaaaaccga gcttgtaatg gacaaaaatc atgccatatt cacatataca    540

ggagggtatg atgttagctt atcagcctat attattagag ttactacgga gctgaacatc    600

gtagatgaaa ttataaagtc tggaggtcta tcatcgggat tttattttga aatagccaga    660

attgaaaacg aaatgaagat caataggcag atactggata atgccgccaa atatgtagaa    720

cacgatcccc gacttgttgc agaacaccgt ttcgaaaaca tgaaaccgaa tttttggtct    780

agaataggaa cggcagctac taaacgttat ccaggagtta tgtacgcgtt tactactcca    840

ctgatttcat tttttggatt gtttgatatt aatgttatag gtttgattgt aattttgttt    900

attatgttta tgctcatctt taacgttaaa tctaaactgt tatggttcct tacaggaaca    960

ttcgttaccg catttatcct cgagcaccac caccaccacc actga                   1005
```

<210> SEQ ID NO 72
<211> LENGTH: 333
<212> TYPE: PRT
<213> ORGANISM: Artificial Sequence
<220> FEATURE:
<223> OTHER INFORMATION: Description of Artifical Sequence: Poxvirus chimera

<400> SEQUENCE: 72

```
Met Ala Ser Ala Ala Ala Lys Thr Pro Val Ile Val Val Pro Val Ile
1               5                   10                  15

Asp Arg Leu Pro Ser Glu Thr Phe Pro Asn Val His Glu His Ile Asn
            20                  25                  30

Asp Gln Lys Phe Asp Asp Val Lys Asp Asn Glu Val Met Pro Glu Lys
        35                  40                  45

Arg Asn Val Val Val Val Lys Asp Asp Asp His Tyr Lys Asp Tyr Ala
    50                  55                  60

Phe Ile Gln Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Asn Phe Phe Thr
            100                 105                 110

Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140
```

```
His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn His Ala Ile Phe
                165                 170                 175

Thr Tyr Thr Gly Gly Tyr Asp Val Ser Leu Ser Ala Tyr Ile Ile Arg
            180                 185                 190

Val Thr Thr Glu Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Met
    210                 215                 220

Lys Ile Asn Arg Gln Ile Leu Asp Asn Ala Ala Lys Tyr Val Glu His
225                 230                 235                 240

Asp Pro Arg Leu Val Ala Glu His Arg Phe Glu Asn Met Lys Pro Asn
                245                 250                 255

Phe Trp Ser Arg Ile Gly Thr Ala Ala Thr Lys Arg Tyr Pro Gly Val
            260                 265                 270

Met Tyr Ala Phe Thr Thr Pro Leu Ile Ser Phe Phe Gly Leu Phe Asp
        275                 280                 285

Ile Asn Val Ile Gly Leu Ile Val Ile Leu Phe Ile Met Phe Met Leu
    290                 295                 300

Ile Phe Asn Val Lys Ser Lys Leu Leu Trp Phe Leu Thr Gly Thr Phe
305                 310                 315                 320

Val Thr Ala Phe Ile Leu Glu His His His His His His
                325                 330
```

<210> SEQ ID NO 73
<211> LENGTH: 26
<212> TYPE: DNA
<213> ORGANISM: Artificial Sequence
<220> FEATURE:
<223> OTHER INFORMATION: Description of Artifical Sequence: Synthetic primer

<400> SEQUENCE: 73
caccatgaaa acgatttccg ttgtta 26

<210> SEQ ID NO 74
<211> LENGTH: 33
<212> TYPE: DNA
<213> ORGANISM: Artificial Sequence
<220> FEATURE:
<223> OTHER INFORMATION: Description of Artifical Sequence: Synthetic primer

<400> SEQUENCE: 74
ttctaacgat tctatttctt gttcatattg tac 33

<210> SEQ ID NO 75
<211> LENGTH: 30
<212> TYPE: DNA
<213> ORGANISM: Artificial Sequence
<220> FEATURE:
<223> OTHER INFORMATION: Description of Artifical Sequence: Synthetic primer

<400> SEQUENCE: 75
agagagagac atatggcggc ggcgaaaact 30

<210> SEQ ID NO 76
<211> LENGTH: 36
<212> TYPE: DNA

<213> ORGANISM: Artificial Sequence
<220> FEATURE:
<223> OTHER INFORMATION: Description of Artifical Sequence: Synthetic
primer

<400> SEQUENCE: 76
ctctctctct ggatccttag ataaatgcgg taacga 36

<210> SEQ ID NO 77
<211> LENGTH: 30
<212> TYPE: DNA
<213> ORGANISM: Artificial Sequence
<220> FEATURE:
<223> OTHER INFORMATION: Description of Artifical Sequence: Synthetic
primer

<400> SEQUENCE: 77
agagagagag ctagcgcggc ggcgaaaact 30

<210> SEQ ID NO 78
<211> LENGTH: 30
<212> TYPE: DNA
<213> ORGANISM: Artificial Sequence
<220> FEATURE:
<223> OTHER INFORMATION: Description of Artifical Sequence: Synthetic
primer

<400> SEQUENCE: 78
aggcacacaa cagaggcagt tccagatttc 30

<210> SEQ ID NO 79
<211> LENGTH: 25
<212> TYPE: DNA
<213> ORGANISM: Artificial Sequence
<220> FEATURE:
<223> OTHER INFORMATION: Description of Artifical Sequence: Synthetic
primer

<400> SEQUENCE: 79
gctggagggc acggtcacca cgctg 25

<210> SEQ ID NO 80
<211> LENGTH: 26
<212> TYPE: DNA
<213> ORGANISM: Artificial Sequence
<220> FEATURE:
<223> OTHER INFORMATION: Description of Artifical Sequence: Synthetic
primer

<400> SEQUENCE: 80
gttgaagctc tttgtgacgg gcgagc 26

<210> SEQ ID NO 81
<211> LENGTH: 18
<212> TYPE: DNA
<213> ORGANISM: Artificial Sequence
<220> FEATURE:
<223> OTHER INFORMATION: Description of Artifical Sequence: Synthetic
primer

<400> SEQUENCE: 81
gtaaaacgac ggccagtg 18

<210> SEQ ID NO 82
<211> LENGTH: 17
<212> TYPE: DNA
<213> ORGANISM: Artificial Sequence
<220> FEATURE:
<223> OTHER INFORMATION: Description of Artifical Sequence: Synthetic
primer

<400> SEQUENCE: 82
caggaaacag ctatgac 17

<210> SEQ ID NO 83
<211> LENGTH: 30
<212> TYPE: DNA
<213> ORGANISM: Artificial Sequence
<220> FEATURE:
<223> OTHER INFORMATION: Description of Artifical Sequence: Synthetic
primer

<400> SEQUENCE: 83
aggcacacaa cagaggcagt tccagatttc 30

<210> SEQ ID NO 84
<211> LENGTH: 41
<212> TYPE: DNA
<213> ORGANISM: Artificial Sequence
<220> FEATURE:
<223> OTHER INFORMATION: Description of Artifical Sequence: Synthetic
primer

<400> SEQUENCE: 84
agagagagag gtcgaccacc atggagtttg ggctgagctg g 41

<210> SEQ ID NO 85
<211> LENGTH: 37
<212> TYPE: DNA
<213> ORGANISM: Artificial Sequence
<220> FEATURE:
<223> OTHER INFORMATION: Description of Artifical Sequence: Synthetic
primer

<400> SEQUENCE: 85
agagagagag gctagctgag gagacggtga ccgtggt 37

<210> SEQ ID NO 86
<211> LENGTH: 43
<212> TYPE: DNA
<213> ORGANISM: Artificial Sequence
<220> FEATURE:
<223> OTHER INFORMATION: Description of Artifical Sequence: Synthetic
primer

<400> SEQUENCE: 86
agagagagag agatctcaca gcatggacat gagggtcccc gct 43

<210> SEQ ID NO 87
<211> LENGTH: 40
<212> TYPE: DNA
<213> ORGANISM: Artificial Sequence
<220> FEATURE:
<223> OTHER INFORMATION: Description of Artifical Sequence: Synthetic
primer

<400> SEQUENCE: 87
agagagagag cgtacgtttg atatccactt tggtcccagg 40

<210> SEQ ID NO 88
<211> LENGTH: 38
<212> TYPE: DNA
<213> ORGANISM: Artificial Sequence
<220> FEATURE:

<223> OTHER INFORMATION: Description of Artifical Sequence: Synthetic
      primer

<400> SEQUENCE: 88
agagagagag gtcgaccacc atggaactgg ggctccgc 38

<210> SEQ ID NO 89
<211> LENGTH: 37
<212> TYPE: DNA
<213> ORGANISM: Artificial Sequence
<220> FEATURE:
<223> OTHER INFORMATION: Description of Artifical Sequence: Synthetic
      primer

<400> SEQUENCE: 89
agagagagag gctagctgag gagacggtga ccgtggt 37

<210> SEQ ID NO 90
<211> LENGTH: 44
<212> TYPE: DNA
<213> ORGANISM: Artificial Sequence
<220> FEATURE:
<223> OTHER INFORMATION: Description of Artifical Sequence: Synthetic
      primer

<400> SEQUENCE: 90
agagagagag agatctcaca gcatggacat gagggtcccc gctc 44

<210> SEQ ID NO 91
<211> LENGTH: 40
<212> TYPE: DNA
<213> ORGANISM: Artificial Sequence
<220> FEATURE:
<223> OTHER INFORMATION: Description of Artifical Sequence: Synthetic
      primer

<400> SEQUENCE: 91
agagagagag cgtacgtttg atctccagct tggtcccctg 40

<210> SEQ ID NO 92
<211> LENGTH: 38
<212> TYPE: DNA
<213> ORGANISM: Artificial Sequence
<220> FEATURE:
<223> OTHER INFORMATION: Description of Artifical Sequence: Synthetic
      primer

<400> SEQUENCE: 92
agagagagag gtcgaccacc atggagttgg gactgagc 38

<210> SEQ ID NO 93
<211> LENGTH: 34
<212> TYPE: DNA
<213> ORGANISM: Artificial Sequence
<220> FEATURE:
<223> OTHER INFORMATION: Description of Artifical Sequence: Synthetic
      primer

<400> SEQUENCE: 93
agagagagag gctagctgag gagacggtga ccag 34

<210> SEQ ID NO 94
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 94
agagagagag agatctggaa ccatggaagc cccagct 37

<210> SEQ ID NO 95
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 95
agagagagag cgtacgtttg atctccacct tggt 34

<210> SEQ ID NO 96
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 96
agagagagag agatctcaca gcatggacat gagggtc 37

<210> SEQ ID NO 97
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 97
agagagagag cgtacgtttg atatccactt tggt 34

<210> SEQ ID NO 98
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 98
agagagagag agatctcaca gcatggacat gagggtc 37

<210> SEQ ID NO 99
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 99
agagagagag cgtacgtttg atttccacct tggt 34

<210> SEQ ID NO 100
<211> LENGTH: 35
<212> TYPE: DNA
<213> ORGANISM: Artificial Sequence
<220> FEATURE:
<223> OTHER INFORMATION: Description of Artifical Sequence: Synthetic primer

<400> SEQUENCE: 100
agagagagag gtcgaccacc atggagttgg gactg 35

<210> SEQ ID NO 101
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 101
agagagagag gctagctgag gagacggtga ccag 34

<210> SEQ ID NO 102
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 102
agagagagag agatctcaca gcatggacat gagggtc 37

<210> SEQ ID NO 103
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 103
agagagagag cgtacgtttg atatccactt tggt 34

<210> SEQ ID NO 104
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 104
agagagagag agatctggaa ccatggaagc cccagct 37

<210> SEQ ID NO 105
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 105
agagagagag cgtacgtttg atctccacct tggt 34

<210> SEQ ID NO 106
<211> LENGTH: 37
<212> TYPE: DNA
<213> ORGANISM: Artificial Sequence
<220> FEATURE:
<223> OTHER INFORMATION: Description of Artifical Sequence: Synthetic primer

<400> SEQUENCE: 106
agagagagag agatctcaca gcatggacat gagggtc 37

<210> SEQ ID NO 107
<211> LENGTH: 34
<212> TYPE: DNA
<213> ORGANISM: Artificial Sequence
<220> FEATURE:
<223> OTHER INFORMATION: Description of Artifical Sequence: Synthetic primer

<400> SEQUENCE: 107
agagagagag cgtacgtttg atttccacct tggt 34

<210> SEQ ID NO 108
<211> LENGTH: 5
<212> TYPE: PRT
<213> ORGANISM: Homo sapiens

<400> SEQUENCE: 108

Leu Glu Trp Ile Gly
1               5

<210> SEQ ID NO 109
<211> LENGTH: 4
<212> TYPE: PRT
<213> ORGANISM: Homo sapiens
<220> FEATURE:
<221> NAME/KEY: SITE
<222> LOCATION: (3)..(3)
<223> OTHER INFORMATION: Xaa is any amino acid

<400> SEQUENCE: 109

Trp Gly Xaa Gly
1

<210> SEQ ID NO 110
<211> LENGTH: 41
<212> TYPE: DNA
<213> ORGANISM: Artificial Sequence
<220> FEATURE:
<223> OTHER INFORMATION: Description of Artifical Sequence: Oligonucleotide primer

<400> SEQUENCE: 110
acgtatcgaa ttcacatgta ctgtacccac tatgaataac g 41

<210> SEQ ID NO 111
<211> LENGTH: 49
<212> TYPE: DNA
<213> ORGANISM: Artificial Sequence
<220> FEATURE:
<223> OTHER INFORMATION: Description of Artifical Sequence: Oligonucleotide primer

<400> SEQUENCE: 111
ttacgataag ctttcattct aacgattcta tttcttgttc atattgtac 49

<210> SEQ ID NO 112
<211> LENGTH: 36
<212> TYPE: DNA
<213> ORGANISM: Artificial Sequence
<220> FEATURE:
<223> OTHER INFORMATION: Description of Artifical Sequence: Oligonucleotide primer

<400> SEQUENCE: 112
ctagtacaag ctttcaagat tgacattccg cattag 36

<210> SEQ ID NO 113
<211> LENGTH: 36
<212> TYPE: DNA
<213> ORGANISM: Artificial Sequence
<220> FEATURE:
<223> OTHER INFORMATION: Description of Artifical Sequence:
Oligonucleotide primer

<400> SEQUENCE: 113
atagctaagc tttcattgtt gacatgatgg aataac 36

<210> SEQ ID NO 114
<211> LENGTH: 41
<212> TYPE: DNA
<213> ORGANISM: Artificial Sequence
<220> FEATURE:
<223> OTHER INFORMATION: Description of Artifical Sequence:
Oligonucleotide primer

<400> SEQUENCE: 114
acgtactgaa ttcccatgta aaaaaatgtg tacagtttct g 41

<210> SEQ ID NO 115
<211> LENGTH: 39
<212> TYPE: DNA
<213> ORGANISM: Artificial Sequence
<220> FEATURE:
<223> OTHER INFORMATION: Description of Artifical Sequence:
Oligonucleotide primer

<400> SEQUENCE: 115
atcgtacaga attccttcaa ttagatcacg gatcttgtc 39

<210> SEQ ID NO 116
<211> LENGTH: 49
<212> TYPE: DNA
<213> ORGANISM: Artificial Sequence
<220> FEATURE:
<223> OTHER INFORMATION: Description of Artifical Sequence:
Oligonucleotide primer

<400> SEQUENCE: 116
ttacgataag ctttcaaatt agtgttatga tggcatttac ttcgtatag 49

<210> SEQ ID NO 117
<211> LENGTH: 825
<212> TYPE: DNA
<213> ORGANISM: Poxvirus

<400> SEQUENCE: 117
atgaaaacga tttccgttgt tacgttgtta tgcgtactac ctgcggttgt ttattcaaca 60
tgtactgtac ccactatgaa taacgctaaa ttaacgtcta ccgaaacatc gtttaatgat 120
aaacaaaaag ttacatttac atgtgattcg ggatattatt ctttggatcc aaatgctgtc 180
tgtgaaacag ataaatggaa atacgaaaat ccatgtaaaa aaatgtgtac agtttctgat 240
tatgtctctg aactatataa taaaccgcta tacgaagtaa atgccatcat aacactaatt 300
tgtaaagacg aaacaaaata ttttcgttgt gaagaaaaaa atggaaatac ttcttggaat 360
gatactgtta cgtgtcctaa tgcggaatgt caatctcttc aattagatca cggatcttgt 420
caaccagtta aagaaaaata ctcatttggg gaacatataa ctatcaactg tgatgttgga 480

-continued

```
tatgaggtta ttggtgcttc gtacataact tgtacagcta attcttggaa tgttattcca    540

tcatgtcaac aaaaatgtga tataccgtct ctatctaatg gattaatttc cggatctaca    600

ttttctatcg gtggcgttat acatcttagt tgtaaaagtg gttttatact aacgggatct    660

ccatcatcca catgtatcga cggtaaatgg aatcccgtac tcccaatatg tatacgatct    720

aacgaagaat ttgatccagt ggaggatggt cccgatgatg agacagattt aagcaaactc    780

tcaaaagacg ttgtacaata tgaacaagaa atagaatcgt tagaa                    825
```

<210> SEQ ID NO 118
<211> LENGTH: 275
<212> TYPE: PRT
<213> ORGANISM: Poxvirus

<400> SEQUENCE: 118

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Ser Gly Tyr Tyr Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asn Lys Pro Leu Tyr Glu Val Asn Ala Ile
                85                  90                  95

Ile Thr Leu Ile Cys Lys Asp Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Glu Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240

Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu
        275
```

<210> SEQ ID NO 119
<211> LENGTH: 816
<212> TYPE: DNA
<213> ORGANISM: Poxvirus

<400> SEQUENCE: 119
catatggcgg cggtgaaaac tcctgttatt gttgtgccag ttattgatag acctccatca 60
gaaacatttc ctaatgttca tgagcatatt aatgatcaga agttcgatga tgtaaaggac 120
aacgaagtta tgccagaaaa aagaaatgtt gtggtagtca aggatgatcc agatcattac 180
aaggattatg cgtttataca gtggactgga ggaaacatta gaaatgatga caagtatact 240
cacttctttt cagggttttg taacactatg tgtacagagg aaacgaaaag aaatatcgct 300
agacatttag ccctatggga ttctaatttt tttaccgagt tagaaaataa aaaggtagaa 360
tatgtagtta ttgtagaaaa cgataacgtt attgaggata ttacgtttct tcgtcccgtc 420
ttgaaggcaa tgcatgacaa aaaaatagat atcctacaga tgagagaaat tattacaggc 480
aataaagtta aaaccgagct tgtaatggac aaaaatcatg ccatattcac atatacagga 540
gggtatgatg ttagcttatc agcctatatt attagagtta ctacggcgct gaacatcgta 600
gatgaaatta taaagtctgg aggtctatca tcgggatttt attttgaaat agccagaatc 660
gaaaacgaaa tgaagatcaa taggcagata ctggataatg ccgccaaata tgtagaacac 720
gatcctcgac ttgttgcaga ataccgtttc gaaaacatga aaccgaattt ttggtctaga 780
ataggaacgg cagctgctaa acgttatcca ctcgag 816

<210> SEQ ID NO 120
<211> LENGTH: 819
<212> TYPE: DNA
<213> ORGANISM: Poxvirus

<400> SEQUENCE: 120
catatggcga ctgtgaataa aactcctgtt attgttgtgc cagttattga tagacctcca 60
tcagaaacat ttcctaatct tcatgagcat attaatgatc agaagttcga tgatgtgaag 120
gacaacgaag ttatgccaga aaaaagaaat gttgtgatag tcaaggatga tccagatcat 180
tacaaggatt atgcgtttat acactggact ggaggaaaca ttagaaatga tgacaagtat 240
actcacttct tttcagggtt ttgtaacacc atgtgtacag aggaaacgaa aagaaatatc 300
gctagacatt tagccctatg ggattctaaa tttttttaccg agttagaaaa taaaaaggta 360
gaatatgtag ttattgtaga aaatgataac gttattgagg atattacgtt tcttcgtcca 420
gtcttaaagg caatgcatga caagaaaata gatatcctac agatgagaga aattattaca 480
ggcaataaag ttaaaaccga gctagtaatg gacaaaaatc atgtcatatt cacatataca 540
ggagggtatg atgttagctt gtcagcctat attattagag ttactacggc gctgaacatt 600
gtagatgaaa ttataaagtc tggaggtcta tcatcgggat tttattttga aatagccaga 660
atcgaaaacg aaatgaagat taacaggcaa ataatggata actctgccaa atacgtagaa 720
cacgatcctc gtcttgttgc agaacaccgc tttgaaaaca tgaaaccaaa tttttggtct 780
agaataggaa cggcagctgt taaacgttat ccactcgag 819

<210> SEQ ID NO 121
<211> LENGTH: 277
<212> TYPE: PRT
<213> ORGANISM: Poxvirus

<400> SEQUENCE: 121

Met Ala Ala Val Lys Thr Pro Val Ile Val Val Pro Val Ile Asp Arg
1 5 10 15

Pro Pro Ser Glu Thr Phe Pro Asn Val His Glu His Ile Asn Asp Gln

```
        20                  25                  30

Lys Phe Asp Asp Val Lys Asp Asn Glu Val Met Pro Glu Lys Arg Asn
        35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu Tyr Arg Phe Glu Asn Met Lys Pro Asn Phe
                245                 250                 255

Trp Ser Arg Ile Gly Thr Ala Ala Ala Lys Arg Tyr Pro Leu Glu His
            260                 265                 270

His His His His His
        275


<210> SEQ ID NO 122
<211> LENGTH: 278
<212> TYPE: PRT
<213> ORGANISM: Poxvirus

<400> SEQUENCE: 122

Met Ala Thr Val Asn Lys Thr Pro Val Ile Val Val Pro Val Ile Asp
1               5                   10                  15

Arg Pro Pro Ser Glu Thr Phe Pro Asn Leu His Glu His Ile Asn Asp
            20                  25                  30

Gln Lys Phe Asp Asp Val Lys Asp Asn Glu Val Met Pro Glu Lys Arg
        35                  40                  45

Asn Val Val Ile Val Lys Asp Asp Pro Asp His Tyr Lys Asp Tyr Ala
    50                  55                  60

Phe Ile His Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110
```

-continued

```
Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn His Val Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Met
    210                 215                 220

Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
                245                 250                 255

Phe Trp Ser Arg Ile Gly Thr Ala Ala Val Lys Arg Tyr Pro Leu Glu
            260                 265                 270

His His His His His His
        275


<210> SEQ ID NO 123
<211> LENGTH: 4
<212> TYPE: PRT
<213> ORGANISM: Homo sapiens
<220> FEATURE:
<221> NAME/KEY: SITE
<222> LOCATION: (3)..(3)
<223> OTHER INFORMATION: Xaa is any amino acid

<400> SEQUENCE: 123

Phe Gly Xaa Gly
1


<210> SEQ ID NO 124
<211> LENGTH: 4
<212> TYPE: PRT
<213> ORGANISM: Homo sapiens
<220> FEATURE:
<221> NAME/KEY: SITE
<222> LOCATION: (2)..(4)
<223> OTHER INFORMATION: Xaa is any amino acid

<400> SEQUENCE: 124

Cys Xaa Xaa Xaa
1
```

VACCINIA VIRUS H3L AND B5R SPECIFIC MONOCLONAL ANTIBODIES AND METHODS OF MAKING AND USING SAME

RELATED APPLICATIONS

This application is a continuation application of U.S. application Ser. No. 12/682,539, filed Apr. 9, 2010, which is the National Phase of International Application No. PCT/US2008/78955, filed Oct. 6, 2008 which designated the U.S. and that International application was published under PCT Article 21(2) in English, which is a continuation-in-part of International Application No. PCT/US2008/78316, filed Sep. 30, 2008, which claims priority to U.S. Provisional Application No. 61/127,729, filed May 14, 2008, and U.S. Provisional Application No. 60/979,028, filed Oct. 10, 2007, all of which applications are expressly incorporated herein by reference in their entirety.

TECHNICAL FIELD

The invention relates to antibodies and subsequences thereof that specifically bind to poxvirus B5R envelope protein, antibodies and subsequences thereof that specifically bind to poxvirus H3L envelope protein, and combinations thereof. The invention also relates to methods of providing a subject with protection against poxvirus infection or pathogenesis including infectious and pathogenic poxviruses (e.g., variola major and variola minor smallpox, monkeypox, cowpox, vaccinia, molluscum contagiosum and camelpox) using antibodies or subsequences thereof that specifically bind to poxvirus B5R envelope protein, antibodies or subsequences thereof that specifically bind to poxvirus H3L envelope protein, and combinations of antibodies or subsequences thereof that specifically bind to poxvirus B5R envelope protein with antibodies or subsequences thereof that specifically bind to poxvirus H3L envelope protein. Furthermore, the invention relates to methods of protecting or decreasing susceptibility of a subject to a poxvirus infection or pathogenesis including infectious and pathogenic poxviruses (e.g., variola major and variola minor smallpox, monkeypox, cowpox, molluscum contagiosum and camelpox) and small pox vaccine viruses using antibodies or subsequences thereof that specifically bind to poxvirus B5R envelope protein, antibodies or subsequences thereof that specifically bind to poxvirus H3L envelope protein, and combinations of antibodies or subsequences thereof that specifically bind to poxvirus B5R envelope protein with antibodies or subsequences thereof that specifically bind to poxvirus H3L envelope protein.

INTRODUCTION

Smallpox is a highly lethal viral infection of humans (30% mortality) (Fenner et al., World Health Organization, Geneva; Henderson et al., *JAMA* 281:2127 (1999)), which can spread rapidly through a population. Smallpox is a top bioterrorism concern, and is frequently generally considered the #1 bioterrorism danger (Hendersonet al., *JAMA* 281:2127 (1999); LeDuc and Jahrling, *Emerg. Infect. Dis.* 7:155 (2001); Meltzer et al., *Emerg. Infect. Dis.* 7:959 (2001); O'Toole et al., *Clin. Infect. Dis.* 34:972 (2002)). The smallpox vaccine consists of live vaccinia virus and is the gold standard of vaccines since it has led to the complete eradication of wild smallpox from the human population. Renewed fears that smallpox might be deliberately released in an act of bioterrorism have led to a resurgence in the study of treatment of smallpox (variola virus) infection, rare but severe side effects of the smallpox vaccine (vaccinia virus, VACV), and treatment of other poxviruses such as monkeypox. Individuals under the age of 35 (approximately 50% of the population) have not been vaccinated against smallpox, leaving them highly susceptible in the event of an outbreak. Furthermore, there is an active smallpox vaccination campaign in the USA military, and VIG (Vaccinia Immune Globulin), is used to treat the rare side effects of vaccination. Finally, in 2003, a monkeypox outbreak occurred for the first time in the USA (Huhn et al., *Clin. Infect. Dis.* 41:1742 (2005)).

Currently, VIG (Vaccinia Immune Globulin) is the only licensed therapeutic to treat the side effects of smallpox vaccination (DryVax immunization), and it is the treatment available in case of an actual smallpox or monkeypox outbreak/bioterrorism event (Hopkins and Lane, *Clin. Infect. Dis.* 39:819 (2004); Wittek, R., *Int. J. Infect. Dis.* 10:193 (2006)). Unfortunately, VIG is a poorly characterized, highly variable, human product that is only available in very limited quantities and is of limited potency (Hopkins and Lane, *Clin. Infect. Dis.* 39:819 (2004); Wittek, R., *Int. J. Infect. Dis.* 10:193 (2006)). Each of these issues is a major problem for biodefense preparedness against a smallpox bioterrorism event. Problems with VIG—particularly the small number of VIG doses available and their limited potency—have led to great interest in the development of a better anti-smallpox immunotherapy.

Poxviruses (vaccinia, variola/smallpox, monkeypox) have two virions forms, Intracellular Enveloped Virions (IMV) and Extracellular Enveloped Virions (EEV), each with distinct biology and numerous different surface proteins (Condit et al., *Adv. Virus Res.* 66:31 (2006); Smith et al., *J. Gen. Virol.* 83:2915 (2002)). As such, an understanding of the virion structures is required to develop knowledge regarding the targets of protective antibodies.

The most abundant viral particle (up to 99% of total) is the intracellular mature virion (IMV), which accumulates in infected cells and is released as cells die (Moss, B., *Poxyiridae: The Viruses and their Replication. In Fundamental Virology*, D. M. Knipe, and P. Howley, eds. (2001)). IMVs are environmentally stable infectious virus particles and likely represent the principle virion type involved in transmission between hosts. An alternate morphogenesis pathway is taken by a proportion of IMVs inside infected cells. These immature virions become wrapped in a double membrane from the trans-Golgi and are then translocated to the cell surface where the outermost membrane fuses with the plasma membrane (Roos et al., *EMBO J.* 15:2343(1996)). These virions may be released from the cell surface as extracellular enveloped virus (EEV) (Smith et al., *J. Gen. Virol.* 83:2915 (2002)). EEV are more fragile and less abundant than the IMV, and are considered to be primarily involved in dissemination within the same host rather than transmission between hosts (Lustig et al., *J. Virol.* 79:13454 (2005); Payne, L. G, *J. Gen. Virol.* 50:89 (1980); Smith et al., *J. Gen. Virol.* 83:2915 (2002))

In humans, high neutralizing antibody titers have been associated with protective immunity against smallpox infection (Mack, J. E., *Pediatr. Nurs.* 14:220 (1988); Sarkar et al., *Bull World Health Organ* 52:307 (1975)). Long-term antibody titers and T cell memory to the smallpox vaccine do not correlate in humans (Crotty et al., *J. Immunol.* 171:4969 (2003); Hammarlund et al., *Nat. Med.* 11:1005 (2005)) excluding the possibility that antibody titers were simply a biomarker for memory T cells. Vaccinia Immune Globulin (VIG) is an effective treatment against smallpox, as it was able to reduce the number of smallpox cases ~80% among exposed individuals in four case controlled studies (Hobday, T. L., *Lancet* 1:907 (1962); Kempe, C. H., *Pediatrics* 25:176 (1960); Kempe et al., *Pediatrics* 18:177 (1956); Marennikova, S. S, *Bull World Health Organ* 27:325 (1962)).

Vaccinia immune globulin (VIG) is licensed to treat complications following smallpox vaccination and would likely be used in the event of a smallpox or monkeypox outbreak. VIG is produced by purifying and pooling IgG from smallpox vaccine recipients. VIG is tested and treated for blood borne pathogens, and tested for efficacy by in vitro neutralization of VACV and in vivo treatment of SCID mice infected with VACV (CangeneCorporation (2005), Vaccinia Immune Globulin Intravenous (Human) (VIGIV) package insert. F. CBER, ed.; DynportVaccineCompany (2005), Vaccinia Immune Globulin Intravenous (Human) (VIGIV) package insert. F. CBER, ed; Goldsmith et al., *Vox Sang* 86:125 (2004); Wittek, R., *Int. J. Infect. Dis.* 10:193 (2006). Recruitment of sufficient donors for production of VIG is a substantial problem, resulting in a small supply of VIG available. Furthermore, the potency of VIG is limited, due to its dilute and polyclonal nature. In addition, there are always safety concerns regarding human blood products. Altogether, these problems with VIG—particularly the small number of VIG doses available and their limited potency—have led to great interest in the development of a better anti-smallpox immunotherapy. These are serious problems with VIG can be solved by production of a high quality mAb product.

SUMMARY

HumanAntibodies that bind to poxvirus proteins, such as B5R and H3L, or anti-B5R and anti-H3L monoclonal antibodies and subsequences thereof, are described. Antibodies provided. Exemplary human antibodies were produced by immunizing trans-chromosomic mice (KM Mice™) with soluble recombinant vaccinia virus B5R or H3L protein. Isolated B5R specific antibodies recognize different epitopes on B5R, for example at least two "epitopes" on B5R, as determined by antibody cross-blocking studies. Isolated H3L specific antibodies recognize one or more epitopes on H3L as determined by antibody cross-blocking studies. Antibodies that specifically bind B5R or H3L protein, and combinations of such antibodies, inhibit virus infection in vitro and/or protect mice (BALB/c and SCID) from vaccinia virus ($VACV_{WR}$ and $VACV_{NYCBOH}$) challenge in in vivo animal models. These results confirm the functional characteristics of human anti-vaccinia virus B5R or H3L monoclonal antibodies and their usefulness alone and in combination as a VIG (vaccinia immune globulin) replacement to treat (e.g., provide a subject with protection against or decrease susceptibility of a subject) poxvirus (e.g., smallpox) infection or as a treatment of adverse side effects or complications associated with or caused by vaccinia virus or poxvirus vaccination, immunization or infection.

The invention therefore provides antibodies, including human, humanized and chimeric B5R or H3L binding antibodies, and compositions including antibodies, such as human, humanized and chimeric B5R or H3L binding antibodies such as pharmaceutical compositions, and kits containing antibody. The invention also provides methods for prophylactic and therapeutic treatment of poxvirus infection and pathogenesis; methods for providing a subject with protection against a poxvirus infection or pathogenesis; and methods for protecting or decreasing susceptibility of a subject to a poxvirus infection and pathogenesis. In various aspects, the poxvirus is a variola major or variola minor smallpox virus. In more particular aspects, the poxvirus is monkeypox, cowpox, vaccinia, molluscum contagiosum or camelpox.

Compositions include fully human, humanized and chimeric (e.g., human/mouse chimera) monoclonal antibodies that recognize and bind to B5R or H3L, or homologs thereof, such as vaccinia B5R, B6 or H3L proteins, or B5R, B6 or H3L protein homolog of a related poxvirus, e.g., such as variola or other poxvirus (e.g., monkeypox). Methods include passive immunization with human, humanized and chimeric (e.g., human/mouse chimera) polyclonal and monoclonal antibodies that bind to B5R or H3L, before or after contact with, exposure to or infection with a poxvirus, or pathogenesis caused by or associated with poxvirus contact, exposure or infection. Methods include treatment methods prior to or before contact with, exposure to or infection with a poxvirus (prophylaxis) as well as treatment methods following contact with, exposure to or infection with a poxvirus (therapeutic) including development of one or more symptoms associated with or caused by poxvirus infection or pathogenesis. Non-limiting examples of symptoms of poxvirus infection or pathogenesis include high fever, fatigue, headache, backache, malaise, rash (maculopapular, vesicular or pustular) or lesions, delirium, vomiting, diarrhea and excess bleeding. Methods of the invention therefore include reducing, decreasing, inhibiting, ameliorating, delaying or preventing onset, progression, severity, duration, frequency, susceptibility or probability of one or more symptoms associated with poxvirus contact, exposure, infection or pathogenesis.

Antibodies that bind to B5R, or H3L, or B5R, or H3L protein homologs are useful for treating a subject having or at risk of having a poxvirus, before infection (prophylaxis) or following infection (therapeutic). The invention therefore provides methods of using antibodies that bind to B5R or H3L in treatment (e.g., therapeutic or prophylactic) of poxvirus infection or pathogenesis.

The invention further provides methods for providing a subject with protection against, or protecting a subject from, poxvirus infection or pathogenesis. In one embodiment, a method includes administering an amount of an antibody that binds to B5R or H3L sufficient to provide the subject with protection against, or protect the subject from, poxvirus infection or pathogenesis.

The invention also provides methods for protecting or decreasing susceptibility of a subject to a poxvirus infection or pathogenesis. In one embodiment, a method includes administering a composition comprising an amount of an antibody that binds to B5R or H3L sufficient to protect or decrease susceptibility of the subject to poxvirus infection or pathogenesis.

The invention additionally provides methods for decreasing or preventing an adverse side effect or complication associated with or caused by vaccination or immunization with a vaccinia virus. In one embodiment, a method includes administering a composition comprising a sufficient amount of an antibody that binds B5R or H3L to decrease or prevent an adverse side effect or complication associated with or caused by vaccination or immunization with a vaccinia virus. In another embodiment, a method includes administering a composition comprising a sufficient amount of an antibody that binds B5R or H3L to an immune-suppressed or HIV-positive subject to decrease or prevent an adverse side effect or complication associated with or caused by vaccination or immunization with a vaccinia virus. In various aspects, adverse side effects or complications decreased or prevented include postvaccinial encephalitis, progressive vaccinia, eczema vaccinatum, generalized vaccinia, accidental infection of close contacts, rashes and periocular infection. In further aspects, the subject is a candidate for or has been vaccinated with a vaccinia virus (e.g., modified vaccinia Ankara (MVA), vaccinia virus Lister strain, vaccinia virus LC16m8 strain, vaccinia virus NYCBOH strain, vaccinia virus Wyeth strain, vaccinia ACAM2000, or vaccinia virus prepared from calf lymph, Dryvax®) or immunized against a poxvirus. In additional various aspects, the subject is administered the antibody that binds B5R or H3L prior to, concurrently with, following or within 1-2, 2-4, 4-12, 12-24, 24-48, 48-72 hours or, 4, 5, 6, 7, or more days of vaccination with vaccinia virus or immunization against a poxvirus.

Antibodies of the invention can bind to B5R or H3L, optionally present on one or more poxvirus (e.g., infectious or pathogenic poxvirus or live or attenuated vaccinia virus or a related poxvirus such as monkeypox) strains or isolates or species. Thus, the antibodies have one or more effects on virus infectivity, replication, proliferation, titer, or onset, progression, severity, frequency, duration or probability of one or more symptoms, adverse side effects or complications associated with or caused by virus infection or pathogenesis, or vaccination with a vaccinia virus, vaccinia virus protein, or immunization against a poxvirus.

Methods of the invention include methods in which partial or complete protection against poxvirus infection or pathogenesis, or a symptom of poxvirus infection or pathogenesis is provided. In one embodiment, a human, humanized or chimeric B5R or H3L binding antibody inhibits poxvirus infection of a cell in vitro or in vivo, or inhibits poxvirus binding to a cell in vitro or in vivo. In another embodiment, a human, humanized or chimeric B5R or H3L antibody reduces or decreases virus titer, infectivity, replication, proliferation, or an amount of a viral protein of one or more vaccinia virus or poxvirus strains, isolates or species. In yet another embodiment, a human, humanized or chimeric B5R or H3L binding antibody inhibits, delays, or prevents increases in virus titer, infectivity, replication, proliferation, or an amount of a viral protein of one or more vaccinia virus or poxvirus strains, isolates or species. In still another embodiment, a human, humanized or chimeric B5R or H3L binding antibody provides a subject with protection against a poxvirus infection or pathogenesis or protects or decreases susceptibility of a subject to infection or pathogenesis, by one more poxvirus strains, isolates or species. In a further embodiment, a human, humanized or chimeric B5R or H3L binding antibody decreases onset, progression, severity, frequency, duration or probability of one or more symptoms or complications associated with infection or pathogenesis by one or more poxvirus strains or isolates or subtypes. Exemplary symptoms include, for example, high fever, fatigue, headache, backache, malaise, rash (maculopapular, vesicular or pustular) or lesions, delirium, vomiting, diarrhea, and excess bleeding.

B5R or H3L binding antibody can be administered or delivered in accordance with the invention by any suitable in vitro, ex vivo or in vivo method. In various embodiments, a composition is administered prior to, concurrently with, or following contact with or exposure to a poxvirus, poxvirus infection or pathogenesis, or vaccination with a vaccinia virus or immunization against a poxvirus. In various aspects, human, humanized or chimeric B5R or H3L binding antibody is administered or in vivo delivered systemically (e.g., intravenous injection, subcutaneous injection, intravenous infusion, intramuscular injection), regionally, or locally to a subject.

Antibodies of the invention include polyclonal and monoclonal antibodies and mixtures thereof, which can be any of IgG, IgA, IgM, IgE, IgD, and any isotype thereof, for example, $IgG_1$, $IgG_2$, $IgG_3$ or $IgG_4$. Antibodies include intact human, humanized and chimeric immunoglobulin molecules with two full-length heavy chains and two full-length light chains (e.g., mature portion of heavy and light chain variable region sequences) as well as subsequences/fragments of heavy or light chain which retain at least a part of a function of a reference or parental intact antibody that specifically binds B5R or H3L protein or B5R or H3L homolog. Antibody subsequences can have the same or substantially the same binding specificity, binding affinity or anti-poxvirus activity as a reference or parental intact anti-B5R or H3L binding antibody.

Exemplary subsequences include Fab, Fab', $F(ab')_2$, Fv, Fd, single-chain Fvs (scFv), disulfide-linked Fvs (sdFv) and $V_L$ or $V_H$, or other binding fragment of an intact immunoglobulin. Antibodies of the invention, useful in accordance with the invention methods, therefore include heavy-chain variable region sequence and light-chain variable region sequence of antibody that specifically bind B5R or H3L.

In further embodiments, an antibody binds to an antigenic region, determinant or epitope of B5R or H3L. Exemplary antigenic regions and epitopes of B5R or H3L homologs include, for example, a sequence region of B5R or H3L as set forth herein or known to one skilled in the art, or a subsequence or a portion thereof.

Antibodies of the invention further include one or more heterologous domains that impart a distinct function or activity on an antibody that binds B5R or H3L. Antibodies include an amino acid heterologous domain when one or more amino acids are distinct from the antibody (i.e., they are not a part of the native antibody). In one embodiment, a heterologous domain comprises a binding protein (e.g., receptor or ligand binding), an enzyme activity, a drug, an antiviral, a toxin, an immune-modulator, a detectable moiety or a tag.

Combination compositions including B5R and H3L binding antibodies, as well as methods of using such combinations, and methods in which such combinations are administered or combined with other compositions prior to, concurrently with or following administration of B5R or H3L antibody. In various embodiments, a composition includes antibody that binds B5R or H3L and an agent that decreases, reduces, inhibits, delays or prevents poxvirus infection or pathogenesis, replication, proliferation, or decreases, reduces, inhibits, delays or prevent the onset, progression, severity, frequency, duration or probability of one or more symptoms or complications associated with poxvirus (e.g., infectious or pathogenic poxvirus or vaccinia virus) infection or pathogenesis, or an adverse symptom or complication associated with vaccination or immunization with a vaccinia virus, vaccine virus protein, or a poxvirus or a poxvirus protein. Examples include a plurality (e.g., a pool) of monoclonal or polyclonal antibodies that each bind B5R and H3L, having the same or a different binding specificity or binding affinity, for B5R and H3L. An additional antibody that binds to a poxvirus protein, different from B5R or H3L binding antibody, can be administered separately from B5R or H3L binding antibody, or as a combination composition. In specific aspects, the additional antibody that binds to a poxvirus protein binds to IMV, cell-associated enveloped virion (CEV) or extracellular enveloped virion (EEV) forms of smallpox. In more specific aspects, the additional antibody binds to poxvirus protein B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog. A plurality of antibodies can be individually administered or administered as a combination composition.

An additional composition may comprise VIG. Thus, compositions and methods of the invention include a combination composition of a B5R or H3L binding antibody and VIG, a combination composition of a B5R and H3L binding antibody and VIG, a combination method including administering separately or as a combination VIG with B5R or H3L binding antibody, and a combination composition of a B5R and H3L binding antibody and VIG.

Additional examples of a combination composition and combination method include administering separately or as a combination composition a protein with B5R or H3L binding antibody. In one specific aspect, a composition of B5R or H3L binding antibody includes an additional protein (e.g., an infectious or pathogenic poxvirus or vaccinia virus or vaccinia virus protein). In another specific aspect, a method includes administering an additional poxvirus or vaccinia virus protein prior to, concurrently with or following administration of B5R or H3L binding antibody. An additional poxvirus protein may be present on IMV, CEV or EEV forms of smallpox. In specific aspects, an additional poxvirus protein is one or more of B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog.

Pharmaceutical compositions including antibodies of the invention and a pharmaceutically acceptable carrier or excipient are provided. Antibodies can be included in a pharmaceutically acceptable carrier or excipient prior to administration to a subject. Pharmaceutical compositions can be administered to a subject by systemic, regional or local delivery. In one embodiment, a method or carrier is suitable for administration systemically, regionally, or locally to a subject.

Kits that include one or more antibodies of the invention are also provided. In one embodiment, a kit includes instructions for treating (prophylaxis or therapeutic) one or more symptoms or complications associated with poxvirus infection of a subject by one or more poxvirus strains or isolates or species (e.g., virus infectivity, replication, proliferation, titer, onset, progression, severity, frequency, duration or probability of one or more symptoms as set forth herein or known in the art, etc.)

DETAILED DESCRIPTION

Figure 1:
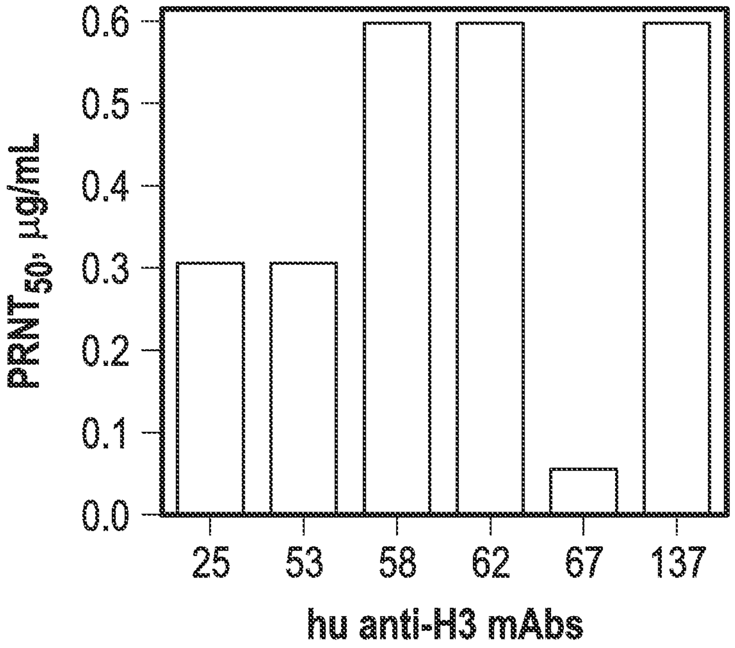
FIG. 1 shows data of human anti-H3 mAb clones titrated in an in vitro VACV IMV neutralization assay to determine $PRNT_{50}$. $PRNT_{50}$ values for the best 6 monoclonal antibodies are shown (μg/ml, y-axis). Control serum $PRNT_{50}$ was greater than 1000 μg/ml.

The invention is based at least in part on antibodies and subsequences thereof that specifically bind to poxvirus B5R envelope protein or B5R protein homologs. The invention is also based at least in part on antibodies and subsequences thereof that specifically bind to poxvirus H3L protein or H3L protein homologs. The invention is further based at least in part on combinations of such antibodies and subsequences.

Invention antibodies, among other things, can provide passive protection against an infectious vaccinia virus, and in multiple mouse models protected the animals from a lethal dose challenge of vaccinia virus. Antibodies of the invention are therefore useful for prophylactic (prior to poxvirus infection) and therapeutic (following poxvirus infection) treatment. In addition, antibodies of the invention are useful for prophylactic (prior to poxvirus infection) and therapeutic (following poxvirus infection) treatment in which subjects are at risk of an adverse side effect or complication associated with or caused by vaccination with a vaccinia virus (e.g., such as the live-virus preparation of vaccinia virus prepared from calf lymph, known as Dryvax®) or immunization against a poxvirus, for example, due to immune suppression. In addition, as inventionantibodies include humanantibodies, which are less likely to induce hypersensitivity from repeated administration and are more likely to remain in a human subjects' body for a longer period of time, antibodies of the invention can be administered to a human subject in advance of contact with or exposure to poxvirus (e.g., infectious or a pathogenic poxvirus such as smallpox), or a live or attenuated vaccinia virus, such as the live-virus preparation of vaccinia virus prepared from calf lymph (Dryvax®).

In accordance with the invention, there are provided antibodies and subsequences thereof that specifically bind to poxvirus B5R envelope protein. In one embodiment, an antibody or subsequence thereof that specifically binds to poxvirus B5R envelope protein includes a sequence at least 60% or more (e.g., 65%, 70%, 75%, 80%, 85%, 90%, 95%, etc.) identical to any heavy chain variable region sequence set forth as SEQ ID NOs:2, 6, or 12, and a sequence at least 60% or more (e.g., 65%, 70%, 75%, 80%, 85%, 90%, 95%, etc.) identical to any light chain variable region sequence set forth as SEQ ID NOs:4, 8 or 10. In another embodiment, an antibody or subsequence thereof that specifically binds to poxvirus B5R envelope protein, includes any heavy chain variable region sequence set forth as SEQ ID NOs:2, 6 or 12, and any light chain variable region sequence set forth as SEQ ID NOs:4, 8 or 10, wherein the antibody or subsequence has one or more amino acid additions, deletions or substitutions of SEQ ID NOs:2, 6 or 12, or SEQ ID NOs:4, 8 or 10. In particular aspects, a sequence is at least 80-85%, 85-90%, 90-95%, 95-100% identical to any heavy chain variable region sequence set forth as SEQ ID NOs:2, 6 or 12, or light chain variable region sequence set forth as SEQ ID NOs:4, 8 or 10. In further aspects, an antibody that specifically bind to poxvirus B5R envelope protein includes or consists of any one of a heavy chain variable region sequence set forth as SEQ ID NOs:2, 6 or 12, or a light chain variable region sequence set forth as SEQ ID NOs:4, 8 or 10.

In accordance with the invention, there are also provided antibodies and subsequences thereof that specifically bind to poxvirus H3L envelope protein. In one embodiment, an antibody or subsequence thereof that specifically binds to poxvirus H3L envelope protein includes a sequence at least 60% or more (e.g., 65%, 70%, 75%, 80%, 85%, 90%, 95%, etc.) identical to any heavy chain variable region sequence set forth as SEQ ID NO:14, and a sequence at least 60% or more (e.g., 65%, 70%, 75%, 80%, 85%, 90%, 95%, etc.) identical to any light chain variable region sequence set forth as SEQ ID NO:16. In another embodiment, an antibody or subsequence thereof that specifically binds topoxvirus H3L envelope protein includes any heavy chain variable region sequence set forth as SEQ ID NOs 14 and any light chain variable region sequence set forth as SEQ ID NO:16, wherein the antibody or subsequence has one or more amino acid additions, deletions or substitutions of SEQ ID NO:14, or SEQ ID NO:16. In particular aspects, a sequence is at least 80-85%, 85-90%, 90-95%, 95-100% identical to any heavy chain variable region sequence set forth as SEQ ID NO:14, or any light chain variable region sequence set forth as SEQ ID NO:16. In further aspects, an antibody that specifically bind to poxvirus H3L envelope protein includes or consists of any one of a heavy chain variable region sequence set forth as SEQ ID NO:14, or a light chain variable region sequence set forth as SEQ ID NO:16.

The term "antibody" refers to a protein that binds to other molecules (antigens) via heavy and light chain variable domains, $V_H$ and $V_L$, respectively. "Antibody" refers to any polyclonal or monoclonal immunoglobulin molecule, or mixtures thereof, such as IgM, IgG, IgA, IgE, IgD. Invention antibodies belong to any antibody class or subclass. Exemplary subclasses for IgG are IgG1, $IgG_2$, $IgG_3$ and $IgG_4$.

As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

The terms "B5R antibody" or "anti-B5R antibody," and grammatical variations thereof, mean a polyclonal or monoclonal antibody that binds to vaccinia virus extracellular enveloped virion (EEV) B5R protein (also referred to as "B5"), or a B5R protein homolog from a related poxvirus, such as monkeypox B5R or variola B6. Antibodies include specific or selective binding to B5R protein or a B5R protein homolog, which is selective for an epitope or antigenic determinant present in B5R protein or B5R protein homolog. That is, binding to proteins other than B5R or B5R protein homolog is such that the binding does not significantly interfere with detection of B5R or B5R protein homolog, unless such other proteins have significant similarity or the same epitope as epitope in B5R protein or B5R protein homolog that is recognized by a B5R homolog antibody. For example, anti-B5R antibodies 131C12, 131C14 and 131C18 also bind to poxvirus envelope protein B6, due to a conserved epitope shared by B5R and B6 proteins. Selective binding can be distinguished from non-selective binding using specificity, affinity, and competitive and non-competitive binding assays, described herein or known in the art.

The terms "H3L antibody" or "anti-H3L antibody," and grammatical variations thereof, mean a polyclonal or monoclonal antibody that binds to vaccinia virus intracellular mature virion (IMV) H3L protein (also referred to as "H3"), or an H3L protein homolog. Antibodies include specific or selective binding to H3L protein or an H3L protein homolog, which is selective for an epitope or antigenic determinant present in H3L protein or H3L protein homolog. That is, binding to proteins other than H3L or H3L protein homolog is such that the binding does not significantly interfere with detection of H3L or H3L protein homolog, unless such other proteins have a similar or same epitope as epitope in H3L protein or H3L protein homolog that is recognized by an H3L/H3L homolog antibody. Selective binding can be distinguished from non-selective binding using specificity, affinity and other binding assays, and competitive and non-competitive binding assays, described herein or known in the art.

The term "isolated," when used as a modifier of an invention composition (e.g., antibodies, subsequences, modified forms, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as multimers/oligomers, modifications (e.g., phosphorylation, glycosylation, lipidation) or derivatized forms, or forms expressed in host cells produced by the hand of man.

An "isolated" composition (e.g., an antibody) can also be "substantially pure" or "purified" when free of most or all of the materials with which it typically associates with in nature. Thus, an isolated antibody that also is substantially pure or purified does not include polypeptides or polynucleotides present among millions of other sequences, such as antibodies of an antibody library or nucleic acids in a genomic or cDNA library, for example. A "substantially pure" or "purified" composition can be combined with one or more other molecules. Thus, "substantially pure" or "purified" does not exclude combinations of compositions, such as combinations of B5R and H3L antibodies, and other poxvirus antibodies or therapies.

Antibodies can be modified. Examples of modifications include one or more amino acid substitutions (e.g., 1-3, 3-5, 5-10 or more residues), additions or deletions (e.g., subsequences or fragments) of the antibody. In particular embodiments, a modified antibody retains at least part of a function or an activity of unmodified antibody, e.g., binding affinity (e.g., $K_d$) or binding specificity to B5R or H3L, binding to a vaccinia virus or pox virus in vitro or an infected cell (e.g., in culture), in vitro virus neutralization, complement-dependent virus neutralization, comettail inhibition, protection from or decreasing susceptibility to poxvirus infection or pathogensis, or decreasing or preventing an adverse side effect or complication associated with or caused by vaccination or immunization with a vaccinia virus or against poxvirus, etc.

A particular example of a modification is where an antibody is altered to have a different isotype or subclass by, for example, substitution of the heavy chain constant region. An alteration of Ig subclass can result in a change or an improvement in a function or activity (e.g., an anti-poxvirus activity, complement fixation, etc.). Thus, modifications include deleting small and large regions of amino acid sequences from an antibody and substituting the deleted region with another amino acid sequence, whether the sequence is greater or shorter in length than the deleted region.

Antibodies and subsequences of the invention include those having at least partial sequence identity to any heavy or light chain variable region sequence set forth as SEQ ID NOs:2, 6 or 12 or SEQ ID NOs:4, 8 or 10, or SEQ ID NO:14, or SEQ ID NO:16. The percent identity of such antibodies and subsequences can be as little as 60%, or can be more (e.g., 65%, 70%, 75%, 80%, 85%, 90%, 95%, etc.). The percent identity can extend over the entire sequence length of a heavy or light chain variable region sequence set forth as SEQ ID NOs:2, 6 or 12 or SEQ ID NOs:4, 8 or 10, or SEQ ID NO:14, or SEQ ID NO:16, or a contiguous region or area within any of SEQ ID NOs:2, 6 or 12 or SEQ ID NOs:4, 8 or 10, or SEQ ID NO:14, or SEQ ID NO:16. In particular aspects, the length of the sequence sharing the percent identity is 5 or more contiguous amino acids, e.g., 5, 6, 7, 8, 9, 10, 11, 12, 13, 14, 15, 16, 17, 18, 19, 20, etc. contiguous amino acids. In additional particular aspects, the length of the sequence sharing the percent identity is 20 or more contiguous amino acids, e.g., 20, 21, 22, 23, 24, 25, 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The term "identity" and grammatical variations thereof, mean that two or more referenced entities are the same. Thus, where two antibody sequences are identical, they have the same amino acid sequence. The identity can be over a defined area (region or domain) of the sequence. "Areas, regions or domains" of homology or identity mean that a portion of two or more referenced entities share homology or are the same. Thus, where two antibody sequences are identical over one or more sequence regions they share identity in these regions.

The extent of identity between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

In accordance with the invention, there are provided antibodies and subsequences in which there are one or more amino acid substitutions of any heavy or light chain variable region sequence set forth as SEQ ID NOs: 2, 6 or 12 or SEQ ID NOs: 4, 8 or 10, or SEQ ID NO: 14, or SEQ ID NO: 16. In particular embodiments, a heavy or light chain CDR (CDR1, CDR2 or CDR3) or FR will have 1-8, 1-5, 1-3 or fewer (e.g., 1 or 2) amino acid substitutions. In an additional embodiment, a substitution within a variable region sequence is not within a CDR. In another embodiment, a substitution within a variable region sequence is not within an FR. Exemplary heavy chain and light chain CDR sequences are as set forth in Table 2 and as follows: SSAMS (SEQ ID NO: 17); VISISGGSTYYADSVKG (SEQ ID NO: 18); ETRYYYSYGMDV (SEQ ID NO: 19); SYSMN (SEQ ID NO: 20); SISSSRSFIYYADSVKG (SEQ ID NO: 21); ERRYYYSYGLDV (SEQ ID NO: 22); SYSMN (SEQ ID NO: 23); SISSSSSYIYYADSVKG (SEQ ID NO: 24); ERRYYYSYGMDV (SEQ ID NO: 25); DYAIH (SEQ ID NO: 26); GISWNGRSIGYADSVKG (SEQ ID NO: 27); DIGFYGSGSLDY (SEQ ID NO: 28); RASQRIGFALA (SEQ ID NO: 29); DASSLET (SEQ ID NO: 30); QQFNTYPFT (SEQ ID NO: 31); RASQGISSALA (SEQ ID NO: 32); DASSLES (SEQ ID NO: 33); QQFNSYPYT (SEQ ID NO: 34); RASQGISSALA (SEQ ID NO: 35); DASSLES (SEQ ID NO: 36); QQFNSYPYT (SEQ ID NO: 37); RASQSVSSYLA (SEQ ID NO: 38); DASNRAT (SEQ ID NO: 39); and QQRSNWPALT (SEQ ID NO: 40).

The structural determinants that contribute to antigen (e.g., B5R and H3L) binding, such as complementarity determining regions (CDR) and framework regions (FR) within hypervariable regions are known in the art. The location of additional regions, such as D- and J-regions are also known. Antibodies and subsequences thereof in which one or more CDR and FR sequences will typically have sufficient sequence identity to a heavy or light chain sequence exemplified herein so as to retain at least partial function or activity of an antibody that includes a heavy and a light chain sequence exemplified herein, e.g., binding affinity (e.g., $K_d$) or binding specificity to B5R or H3L, binding to a vaccinia virus or pox virus or an infected cell in vitro (e.g., in culture), in vitro virus neutralization, complement-dependent virus neutralization, comet-tail inhibition, protection from or decreasing susceptibility to poxvirus infection or pathogensis, or decreasing or preventing an adverse side effect or complication associated with or caused by vaccination or immunization with a vaccinia virus or against poxvirus.

Amino acid substitutions can be conservative or non-conservative and may be in the constant or variable (e.g., hypervariable, such as CDR or FR) region of the antibody. One or a few amino acid substitutions (e.g., 2, 3, 4 or 5) in constant or variable regions are likely to be tolerated. Non-conservative substitution of multiple amino acids in hypervariable regions is likely to affect binding activity, specificity or antibody function or activity.

A "conservative substitution" means the replacement of one amino acid by a biologically, chemically or structurally similar residue. Biologically similar means that the substitution is compatible with biological activity, e.g., specifically binds to B5R or H3L. Structurally similar means that the amino acids have side chains with similar length, such as alanine, glycine and serine, or similar size. Chemical similarity means that the residues have the same charge or are both hydrophilic or hydrophobic. Particular non-limiting examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Regional mutability analysis can be used to predict the effect of particular substitutions in complementarity determining regions (CDR) and framework regions (FR) (Shapiro et al., *J. Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon QSAR can in turn be used to predict the effect of substitutions (mutations). For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J Biol Chem.* 277:29897 (2002)). The skilled artisan can therefore use such analysis to predict amino acid substitutions of antibodies and subsequences that are likely to result in an antibody or subsequence that retains at least partial activity or function of non-substituted antibody or subsequence.

The effect of a given substitution can be assayed in order to identify antibodies retaining at least a part of the binding activity, specificity or antibody function or activity of unsubstituted antibody. For example, an amino acid substitution in a hypervariable region may be assayed for B5R or H3L binding activity or binding specificity, binding to a vaccinia virus or pox virus or an infected cell in vitro (e.g., in culture), in vitro virus neutralization, complement-dependent virus neutralization, comet-tail inhibition, protection from or decreasing susceptibility to poxvirus infection or pathogensis, or decreasing or preventing an adverse side effect or complication associated with or caused by vaccination or immunization with a vaccinia virus or against poxvirus. Antibodies having amino acid substitutions are included so long as at least a part of a function or activity such as binding affinity, binding specificity, binding to a vaccinia virus or pox virus or an infected cell in vitro (e.g., in culture), in vitro virus neutralization, complement-dependent virus neutralization, comet-tail inhibition, protection from or decreasing susceptibility to poxvirus infection or pathogensis, decreasing or preventing an adverse side effect or complication associated with or caused by vaccination or immunization with a vaccinia virus or against poxvirus, etc. is at least partially retained.

Modifications include changes to an activity or function of a reference composition (e.g., affinity or specific binding to B5R or H3L, an anti-poxvirus activity, such as complement fixation, as determined by a complement-dependent virus neutralization assay). Modified antibodies having altered characteristics, such as increased binding affinity, can be produced using methods known in the art. For example, affinity maturation techniques can be used to improve antibody binding affinity (US 2004/0162413 A1; U.S. Pat. Nos. 6,656,467, 6,531,580, 6,590,079 and 5,955,358; Fiedler et al., *Protein Eng.* 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

Antibodies include subsequences (e.g., fragments) and modified forms (e.g., sequence variants) as set forth herein. An "antibody" subsequence refers to a functional fragment or subsequence of immunoglobulin molecule. In particular embodiments, B5R and H3L antibody subsequences include an Fab, Fab', $F(ab')_2$, Fd, Fv, single-chain Fvs (scFv), disulfide-linked Fvs (sdFv) and $V_L$ or $V_H$ domain fragments. In particular aspects, an Fab, Fab' and $F(ab')_2$, Fd, Fv, single-chain Fvs (scFv), disulfide-linked Fvs (sdFv) and $V_L$ or $V_H$ domain subsequence has at least a part of a sequence set forth in any of SEQ ID NOs:2, 6 or 12 or SEQ ID NOs: 4, 8 or 10, or SEQ ID NOs:14 or 22, or SEQ ID NOs:16, 18, 20, 24, 26, or 28. In additional aspects, an Fab, Fab' and $F(ab')_2$, Fd, Fv, single-chain Fvs (scFv), disulfide-linked Fvs (sdFv) and $V_L$ or $V_H$ domain subsequence has substantially the same or has the same B5R or H3L binding affinity or B5R or H3L binding specificity, or one or more functions or activities of B5R or H3L antibody, such as an anti-poxvirus activity in vitro or in vivo (e.g., virus neutralization, complement-dependent virus neutralization, comet-tail inhibition, efficacy in providing a subject with some protection against posvirus infection or pathogenesis, protecting or decreasing susceptibility of a subject from poxvirus infection or pathogenesis of a cell in vitro, or decreasing or preventing an adverse side effect or complication associated with or caused by vaccination or immunization with or against vaccinia virus). The terms "functional subsequence" and "functional fragment" when referring to an antibody of the invention refers to a portion of an antibody that retains at least a part of one or more functions or activities as an intact reference antibody.

B5R and H3L binding antibody subsequences, including single-chain antibodies, can include all or a portion of heavy or light chain variable region(s) (e.g., CDR1, CDR2 or CDR3) alone or in combination with all or a portion of one or more of the following: hinge region, CH1, CH2, and CH3 domains. Also included are antigen-binding subsequences of any combination of heavy or light chain variable region(s) (e.g., CDR1, CDR2 or CDR3) with a hinge region, CH1, CH2, and CH3 domains.

B5R and H3L antibody subsequences (e.g., Fab, Fab', F(ab')2, Fd, scFv, sdFv and $V_L$ or $V_H$) can be prepared by proteolytic hydrolysis of the antibody, for example, by pepsin or papain digestion of whole antibodies. Antibody fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the H3L/

H3L homolog antibody gene into a host cell such as Cos cells or *E. coli*. The recombinant host cells synthesize intact or single antibody chain, such as scFv (see, e.g., Whitlow et al., In: *Methods: A Companion to Methods in Enzymology* 2:97 (1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Additional modifications of antibodies included in the invention are antibody additions (derivatives)/insertions. For example, an addition can be the covalent or non-covalent attachment of any type of molecule to the antibody. Specific examples of antibody additions and derivatives include glycosylation, acetylation, phosphorylation, amidation, formylation, ubiquitinatation, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified antibody having an amino acid addition is one in which a second heterologous sequence, i.e., heterologous functional domain is attached (covalent or non-covalent binding) that confers a distinct or complementary function upon the antibody. Such sequences can be referred to as chimeric sequences. For example, an Fc region can be a chimera that includes portions of human IgG1 and IgG3 Fc regions, which provides the antibody with increased complement fixation as compared to an antibody with an IgG1 or IgG3 Fc. In another example, an amino acid tag such as T7 or polyhistidine can be attached to antibody in order to facilitate purification or detection of antigen or poxvirus(es). Yet another example is an antiviral attached to an antibody in order to target cells infected with poxvirus for killing, proliferation inhibition, replication inhibition, etc. Thus, in other embodiments the invention provides antibodies and a heterologous domain, wherein the domain confers a distinct function, i.e. a heterologous functional domain, on the antibody.

Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), radioisotope.

Linkers, such as amino acid or peptidimimetic sequences may be inserted between the antibody sequence and the heterologous functional domain so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additional examples of heterologous functional domains are detectable labels. Thus, in another embodiment, the invention provides B5R and H3L antibodies that are detectably labeled.

Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified. Ligands may bind other molecules such as biotin, which may bind avidin or streptavidin, and IgG, which can bind protein A.

Modifications further include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc.

It is understood that an invention antibody or subsequence may have multiple (e.g., two or more) variations, modifications or labels. For example, a monoclonal antibody may be coupled to biotin to detect its presence with avidin as well as labeled with $I^{125}$ so that it provides a detectable signal. Other permutations and possibilities will be readily apparent to those of ordinary skill in the art, and are considered to be within the scope of the invention.

The term "human," when used in reference to an antibody, means that the amino acid sequence of the antibody is fully human. A "human B5R antibody" or "human anti-B5R antibody" therefore refers to an antibody having human immunoglobulin amino acid sequences, i.e., human heavy and light chain variable and constant regions that specifically bind to B5R protein or B5R protein homolog. A "human H3L antibody" or "human anti-H3L antibody" therefore refers to an antibody having human immunoglobulin amino acid sequences, i.e., human heavy and light chain variable and constant regions that specifically bind to H3L protein or H3L protein homolog. That is, all of the antibody amino acids are human or can or do exist in a human antibody. Thus, for example, an antibody that is non-human may be made fully human by substituting the non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest,* $4^{th}$ Ed. US Department of Health and Human Services. Public Health Service (1987); and Chothia and Lesk *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)). Human antibodies of the invention therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, non-human primate, etc.) of one or more determining regions (CDRs) that specifically bind to the desired antigen (e.g., H3L) in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)). Antibodies referred to as "primatized" in the art are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

As used herein, the term "chimeric" and grammatical variations thereof, when used in reference to an antibody, means that the amino acid sequence of the antibody contains one or more portions that are derived from, obtained or isolated from, or based upon two or more different species.

That is, for example, a portion of the antibody may be human (e.g., a constant region) and another portion of the antibody may be non-human (e.g., a murine heavy or light chain variable region). Thus, a chimeric antibody is a molecule in which different portions of the antibody are of different species origins. Unlike a humanized antibody, a chimeric antibody can have the different species sequences in any region of the antibody.

As used herein, the terms "B5R," "B5", "B5R protein," "B5 protein," "B5R sequence," "B5 sequence," "B5R domain" and "B5 domain" refer to all or a portion of an B5R protein sequence (e.g., a subsequence such as an antigenic region or epitope) isolated from, based upon or present in any naturally occurring or artificially produced (e.g., genetically engineered) poxvirus strain or isolate or subtype or a species of poxvirus. Thus, the term B5R and the like include B5R sequence of vaccinia virus, or B5R homolog of variola major and variola minor small pox virus, or monkeypox, as well as naturally occurring variants produced by mutation during the virus life-cycle, produced in response to a selective pressure (e.g., drug therapy, expansion of host cell tropism or infectivity, etc.), as well as recombinantly or synthetically produced B5R sequences. A B5R homolog is a sequence having a significant sequence similarity or identitiyidentity to one or more exemplary vaccinia virus B5R protein sequencesequences set forth as SEQ ID NOs:41-52. Typical sequence identities of B5R homologs in other poxviruses are 90% or more. Sequence identities of B5R homologs may be less, however. B5R homologs may be referred to by a different name, due to the position of the coding sequence in the virus genome, which determines the name. SequencesRepresentative non-limiting sequences and the names of B5R homologs are known in the art. B5R and B5R homologs to which antibodies bind include sequences within amino acid sequences set forth as SEQ ID NOs:41-52:

```
                                                       (SEQ ID NO: 41)
MKTISVVTLL CVLPAVVYST CTVPTMNNAK LTSTETSFNN NQKVTFTCDQ GYHSSDPNAV

CETDKWKYEN PCKKMCTVSD YISELYNKPL YEVNSTMTLS CNGETKYFRC EEKNGNTSWN

DTVTCPNAEC QPLQLEHGSC QPVKEKYSFG EYITINCDVG YEVIGASYIS CTANSWNVIP

SCQQKCDIPS LSNGLISGST FSIGGVIHLS CKSGFILTGS PSSTCIDGKW NPILPTCVRS

NEKFDPVDDG PDDETDLSKL SKDVVQYEQE IESLEATYHI IIVALTIMGV IFLISVIVLV

CSCDKNNDQY KFHKLLPVV

Copenhagen strain B5R
                                                       (SEQ ID NO: 42)
MKTISVVTLL CVLPAVVYST CTVPTMNNAK LTSTETSFNN NQKVTFTCDQ GYHSSDPNAV

CETDKWKYEN PCKKMCTVSD YISELYNKPL YEVNSTMTLS CNGETKYFRC EEKNGNTSWN

DTVTCPNAEC QPLQLEHGSC QPVKEKYSFG EYMTINCDVG YEVIGASYIS CTANSWNVIP

SCQQKCDIPS LSNGLISGST FSIGGVIHLS CKSGFILTGS PSSTCIDGKW NPVLPICVRT

NEEFDPVDDG PDDETDLSKL SKDVVQYEQE IESLEATYHI IIVALTIMGV IFLISVIVLV

CSCDKNNDQY KFHKLLP

VV Western Reserve strain B5R
                                                       (SEQ ID NO: 43)
MKTISVVTLL CVLPAVVYST CTVPTMNNAK LTSTETSFND KQKVTFTCDQ GYHSSDPNAV

CETDKWKYEN PCKKMCTVSD YISELYNKPL YEVNSTMTLS CNGETKYFRC EEKNGNTSWN

DTVTCPNAEC QPLQLEHGSC QPVKEKYSFG EYMTINCDVG YEVIGASYIS CTANSWNVIP
```

-continued

SCQQKCDMPS LSNGLISGST FSIGGVIHLS CKSGFTLTGS PSSTCIDGKW NPVLPICVRT

NEEFDPVDDG PDDETDLSKL SKDVVQYEQE IESLEATYHI IIVALTIMGV IFLISVIVLV

CSCDKNNDQY KFHKLLP

VV MVA strain B5R (SEQ ID NO: 44)

MKTISVVTLL CVLPAVVYST CTVPTMNNAK LTSTETSFNN NQKVTFTCDQ GYHSSDPNAV

CETDKWKYEN PCKKMCTVSD YISELYNKPL YEVNSTMTLS CNGETKYFRC EEKNGNTSWN

DTVTCPNAEC QPLQLEHGSC QPVKEKYSFG EYITINCDVG YEVIGASYIS CTANSWNVIP

SCQQKCDIPS LSNGLISGST FSIGGVIHLS CKSGFILTGS PSSTCIDGKW NPILPTCVRS

NEKFDPVDDG PDDETDLSKL SKDVVQYEQE IESLEATYHI IIVALTIMGV IFLISVIVLV

CSCDKNNDQY KFHKLLP

VV Acambis strain B5R (SEQ ID NO: 45)

MKTISVVTLL CVLPAVVYST CTVPTMNNAK LTSTETSFND KQKVTFTCDQ GYHSLDPNAV

CETDKWKYEN PCKKMCTVSD YVSELYDKPL YEVNSTMTLS CNGETKYFRC EEKNGNTSWN

DTVTCPNAEC QPLQLEHGSC QPVKEKYSFG EYITINCDVG YEVIGASYIS CTANSWNVIP

SCQQKCDMPS LSNGLISGST FSIGGVIHLS CKSGFTLTGS PSSTCIDGKW NPILPTCVRS

NEKFDPVDDG PDDETDLSKL SKDVVQYEQE IESLEATYHI IIVALTIMGV IFLISVIVLV

CSCDKNNDQY KFHKLLP

VV B5R Tian Tan strain B5R (SEQ ID NO: 46)

MKTISVVTLL CVLPAVVYST CTVPTMNNAK LTSTETSFND KQKVTFTCDQ GYHSSDPNAV

CETDKWKYEN PCKKMCTVSD YISELYNKPL YEVNSTMTLS CNGETKYFRC EEKNGNTSWN

DTVTCPNAEC QPLQLEHGSC QPVKEKYSFG EYMTINCDVG YEVIGASYIS CTANSWNVIP

SCQQKCDMPS LSNGLISGST FSIGGVIHLS CKSGFILTGS PSSTCIDGKW NPVLPICVRT

NEEFDPVDDG PDDETDLSKL SKDVVQYEQE IESLEATYHI IMVALTIMGV IFLISVIVLV

CSCDKNNDQY KFHKLLP

Camel pox homolog of VV B5R (SEQ ID NO: 47)

MKTISVVTLL CVLPAVVYST CTVPTMNNAK LTSTETSFND KQKVTFTCDS GYYSLDPNAV

CETDKWKYEN PCKKMCTVSD YVSELYDKPL YEVNATITLI CKDETKYFRC EEKNENTSWN

DTVTCPNAEC QSLQLEHGSC QPVKEKYSFG EHITINCDVG YEVIGASYIS CTANSRNIIP

SCQQKCDIPS LSNGLISGST FSIGGVIHLS CKSGFILTGS SSSTCIDGKW NPVLPICVRS

NEEFDPVEDG PDDETDLSKL SKDVVQYEQE IESLEVTYHI IIVALTIMGV IFLISVIVLV

CSCNKNNNQY KFHKLLP

Variola major virus (Bangladesh) glycoprotein homolog of VV B5R (SEQ ID NO: 48)

MKTISVVTLL CVLPAVVYST CTVPTMNNAK LTSTETSFND KQKVTFTCDS GYYSLDPNAV

CETDKWKYEN PCKKMCTVSD YVSELYNKPL YEVNAIITLI CKDETKYFRC EEKNGNTSWN

DTVTCPNAEC QSLQLDHGSC QPVKGKYSFG EHITINCDVG YEVIGASYIT CTANSWNVIP

SCQQKCDIPS LSNGLISGST FSIGGVIHLS CKSGFILTGS PSSTCIDGKW NPVLPICIRS

NEEFDPVEDG PDDETDLSKL SKDVVQYEQE IESLEATYHI IIVALTIMGV IFLISVIVLV

CSCNKNNDQY KFHKLLL

Variola major virus (India) gp175 homolog of VV B5R (SEQ ID NO: 49)

MKTISVVTLL CVLPAVVYST CTVPTMNNAK LTSTETSFND KQKVTFTCDS GYYSLDPNAV

CETDKWKYEN PCKKMCTVSD YVSELYNKPL YEVNAIITLI CKDETKYFRC EEKNGNTSWN

-continued

```
DTVTCPNAEC QSLQLDHGSC QPVKEKYSFG EHITINCDVG YEVIGASYIT CTANSWNVIP

SCQQKCDIPS LSNGLISGST FSIGGVIHLS CKSGFILTGS PSSTCIDGKW NPVLPICIRS

NEEFDPVEDG PDDETDLSKL SKDVVQYEQE IESLEATYHI IIVALTIMGV IFLISVIVLV

CSCNKNNDQY KFHKLLL
```

Variola minor virus (Garcia) H7R homolog of VV B5R (SEQ ID NO: 50)

```
MKTISVVTLL CVLPAVVYST CTVPTMNNAK LTSTETSFND KQKVTFTCDS GYYSLDPNAV

CETDKWKYEN PCKKMCTVSD YVSELYNKPL YEVNAIITLI CKDETKYFRC EEKNGNTSWN

DTVTCPNAEC QSLQLDHGSC QPVKEKYSFG EHITINCDVG YEVIGASYIT CTANSWNVIP

SCQQKCDIPS LSNGLISGST FSIGGVIHLS CKSGFILTGS PSSTCIDGKW NPVLPICIRS

NEEFDPVEDG PDDETDLSKL SKDVVQYEQE IESLEATYHI IIVALTIMGV IFLISVIVLV

CSCNKNNDQY KFHKLL
```

Monkeypox virus B6R homolog of VV B5R (SEQ ID NO: 51)

```
MKTISVVTLL CVLPAVVYST CTVPTMNNAK LTSTETSFND KQKVTFTCDS GYHSLDPNAV

CETDKWKYEN PCKKMCTVSD YVSELYDKPL YEVNSTMTLS CNGETKYFRC EEKNGNTSWN

DTVTCPNAEC QPLQLEHGSC QPVKEKYSFG EYMTINCDVG YEVIGVSYIS CTANSWNVIP

SCQQKCDIPS LSNGLISGST FSIGGVIHLS CKSGFTLTGS PSSTCIDGKW NPILPTCVRS

NEEFDPVDDG PDDETDLSKL SKDVVQYEQE IESLEATYHI IIMALTIMGV IFLISIIVLV

CSCDKNNDQY KFHKLLP
```

Cowpox B4R homolog of VV B5R (SEQ ID NO: 52)

```
MKTISVVTLL CVLPAVVYST CTVPTMNNAK LTSTETSFND KQKVTFTCDQ GYHSLDPNAV

CETDKWKYEN PCKKMCTVSD YVSELYDKPL YEVNSTMTLS CNGETKYFRC EEKNGNTSWN

DTVTCPNAEC QPLQLEHGSC QPVKEKYSFG EYMTINCDVG YEVIGASYIS CTANSWNVIP

SCQQKCDIPS LSNGLISGST FSIGGVIHLS CKSGFTLTGS PSSTCIDGKW NPILPTCVRS

NEEFDLVDDG PDDETDLSKI SKDVVQYEQE IESLEATYHI IIVALTIMGV IFLISIIVLV

CSCDKNNDQY KFHKLLP
```

As used herein, the terms “H3L,” “H3”, “H3L protein,” “H3 protein,” “H3L envelope protein,” “H3 envelope protein,” “H3L sequence,” “H3 sequence,” “H3L domain” and “H3 domain” refer to all or a portion of an H3L envelope protein sequence (e.g., a subsequence such as an antigenic region or epitope) isolated from, based upon or present in any naturally occurring or artificially produced (e.g., genetically engineered) poxvirus strain or isolate or subtype or a species of poxvirus. Thus, the term H3L and the like include H3L sequence of vaccinia virus, or H3L homolog I3L of variola major and variola minor small pox virus, as well as naturally occurring variants produced by mutation during the virus life-cycle, produced in response to a selective pressure (e.g., drug therapy, expansion of host cell tropism or infectivity, etc.), as well as recombinantly or synthetically produced H3L sequences. An H3L homolog is a sequence having a significant sequence similarity or identity to exemplary vaccinia virus H3L protein sequence set forth as SEQ ID NOs:53-65. Typical sequence identities of H3L homologs in other poxviruses are 90% or more. Sequence identities of H3L homologs may be less, however. For example, molluscum contagiosum gene MC084L is a VV H3L homolog that has 29% identity, and is 53% similar to H3L set forth as SEQ ID NO:31. H3L homologs also typically have a similar length to exemplary H3L protein sequence set forth as SEQ ID NO:31, usually a length of about 320-330 amino acids. H3L homologs may be referred to by a different name, due to the position of the coding sequence in the virus genome, which determines the name. Exemplary names for H3L homologs are H3L, I3L, J3L and MC084L. Other sequences and the names of H3L homologs are also known in the art. Representative non-limiting H3L and H3L homologs to which antibodies bind include sequences within amino acid sequences set forth as SEQ ID NOs:53-65:

VVcopenhagen strain H3L (SEQ ID NO: 53)

```
MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY
```

-continued

VVIVENDNVI EDITFLRPVL KAMHDKKIDI LQMREIITGN KVKTELVMDK NHTIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI

VV western reserve strain H3L (SEQ ID NO: 54)

MAAAKTPVIV VPVIDRLPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAATKRYPG VMYAFTTPLI SFFGLFDINV IGLIVILFIM

FMLIFNVKSK LLWFLTGTFV TAFI

VV MVA strain H3L (SEQ ID NO: 55)

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEYRFE NMKPNFWSRI GTAAAKRYPG VMYAFTTPLI SFFGLFDINV IGLIVILFIM

FMLIFNVKSK LLWFLTGTFV TAFI

VV Acambis MVA strain H3L (SEQ ID NO: 56)

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEYRFE NMKPNFWSRI GTAAAKRYPG VMYAFTTPLI SFFGLFDINV IGLIVILFIM

FMLIFNVKSK LLWFLTGTFV TAFI

VV Tian Tian strain H3L (SEQ ID NO: 57)

MAAAKTPVIV VPVIDRLPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTELNIVD EIIKSGGLSS GFYFEIARIE NEMKINRQIL DNAAKYVEHD

PRLVAEHRFE NMKPNFWSRI GTAATKRYPG VMYAFTTPLI SFFGLFDINV IGLIVILFIM

FMLIFNVKSK LLWFLTGTFV TAFI

*Camelpox* J3L homolog of VV H3L (SEQ ID NO: 58)

MAAAKTPVIV VPVIDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KAMHDKKIDI LQMREIITGN KVKTELVMDK DHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI

-continued

Variola major virus (Bangladesh) I3L homolog of VV H3L
(SEQ ID NO: 59)

MATVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

Variola major virus (India) I3L homolog of VV H3L
(SEQ ID NO: 60)

MATVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEIKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

Variola minor virus (Garcia) J3L homolog of VV H3L
(SEQ ID NO: 61)

MAAVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

*Camelpox virus* strain M96 homolog of VV H3L
(SEQ ID NO: 62)

MAAVNRTPVI VVPVIDRHPS ETFPNVHEHI NDQKFDDVKD NEVMPEKRDV VIVKDDPDHY

KDYAFIQWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNYAIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAAKRYP GVMYAFTTPL ISFFGLFDIN VIGLIVILFI

MFMLIFNVKS KLLWFLTGTF VTAFI

*Monkeypox virus* (Zaire-96-I-16) H3L homolog of VV H3L
(SEQ ID NO: 63)

MAAAKTPVIV VPVIDRPPSE TFPNVHEHIN DQKFDDVKDN EVMQEKRDVV IVNDDPDHYK

DYVFIQWTGG NIRDDDKYTH FFSGFCNTMC TEETKRNIAR HLALWDSKFF IELENKNVEY

VVIIENDNVI EDITFLRPVL KAIHDKKIDI LQMREIITGN KVKTELVIDK DHAIFTYTGG

YDVSLSAYII RVTTALNIVD EIIKSGGLSS GFYFEIARIE NEMKINRQIM DNSAKYVEHD

PRLVAEHRFE TMKPNFWSRI GTVAAKRYPG VMYTFTTPLI SFFGLFDINV IGLIVILFIM

FMLIFNVKSK LLWFLTGTFV TAFI

*Monkeypox virus* (GRI-90) J3L protein homolog of VV H3L
(SEQ ID NO: 64)

MAAAKTPVIV VPVIDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KAMHDKKIDI LQMREIITGN KVKTELVMDK DHAIFTYTGG

-continued

```
YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI
```

molluscum contagiosum gene MC084L, a VV H3L homolog (SEQ ID NO: 65)

```
MAESESTIPL YVLPVVGRGA AEVVPGNKST GTVRVSQWTP GGAKSEQAGQ YYSALCRVLC

SAEAKQTILN HLSLWKELGS ESAPKAAGAE SEYAIVVEDD NTVQPLLLQS AAALVGGMRA

QQVHVLQLRE PLHAGVRAQT PLSGNPSAYV YPARLHASLG AYIIHKPSAG RLHAEFLRSR

VTAGLPLELP RVERAQGLTR MVLAGSSEYV THEYRLRNEL RGREYGASLR ARAGAWLARN

YPQAYAAATT PVFSLFGRVD VNVFGVLSVL FVLVLVVFDV QSRLAWLLVG ALASGLLQ
```

Predicted epitopes for H3L comprise three sequences, denoted PE1, PE2 and PE3, (SEQ ID NOs:66-68, respectively; U.S. Pat. No. 7,393,533) are underlined and in bold text, within an amino acid sequence (SEQ ID NO:53):

MAAVKTPVIV VPVIDRPPSE TFPNVHEHIN DQKFDDVKDN

EVMPEKRNVV VVKDDPDHYK DYAFIQWTGG NIRNDDKYTH

FFSGFCNTMC TEETKRNIAR HLALWDSNFF TELENKKVEY

VVIVENDNVI EDITFLRPVL KAMHDKKIDI LQMREIITGN

KVKTELVMDK NHTIFTYTGG YDVSLSAYII RVTTALNIVD

EIIKSGGLSS GFYFEIARIE NEMKINRQIL DNAAKYVEHD

PRLVAEHRFE NMKPNFWSRI GTAAAKRYPG VMYAFTTPLI

SFFGLFDINV IGLIVILFIM FMLIFNVKSK LLWFLTGTFV TAFI

Invention antibodies include antibodies having kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

The term "bind," or "binding," when used in reference to an antibody, means that the antibody specifically binds to all or a part of an antigen (e.g., B5R, H3L, or B5R or H3L homolog). Thus, an antibody specifically binds to all or a part of sequence or an antigenic epitope present on B5R, H3L, or B5R or H3L homolog, but may also bind to other proteins should those proteins have the same or a similar epitope as B5R, H3L, or B5R or H3L homolog antigenic epitope. Antibodies that bind to the same sequence or epitope or a part of the epitope as an antibody that binds to B5R, H3L, or B5R or H3L homolog, can have more or less relative binding affinity or specificity for B5R, H3L, or B5R or H3L homolog, and are expressly included. For example, in particular embodiments, antibodies are provided that bind to both B5R and B6 proteins, due to a shared epitope on the B5R and B6 proteins.

A part of an antigenic epitope means a subsequence or a portion of the epitope. For example, if an epitope includes 8 contiguous amino acids, a subsequence and, therefore, a part of an epitope may be 7 or fewer amino acids within this 8 amino acid sequence epitope. In addition, if an epitope includes non-contiguous amino acid sequences, such as a 5 amino acid sequence and an 8 amino acid sequence which are not contiguous with each other, but form an epitope due to protein folding, a subsequence and, therefore, a part of an epitope may be either the 5 amino acid sequence or the 8 amino acid sequence alone.

Epitopes typically are short amino acid sequences, e.g. about five to 15 amino acids in length. Systematic techniques for identifying epitopes are also known in the art and are described, for example, in U.S. Pat. No. 4,708,871. Briefly, a set of overlapping oligopeptides derived from an antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-H3L monoclonal antibody. Alternatively, phage display peptide library kits (New England BioLabs) are commercially available for epitope mapping. Using these methods, binding affinity for every possible subset of consecutive amino acids may be determined in order to identify the epitope that a particular antibody binds. Epitopes may also be identified by inference when epitope length peptide sequences are used to immunize animals from which antibodies that bind to the peptide sequence are obtained. Continuous epitopes can also be predicted using computer programs, such as BEPITOPE, known in the art (Odorico et al., *J. Mol. Recognit.* 16:20 (2003)).

Antibodies of the invention include B5R and H3L antibodies and subsequences thereof with more or less affinity for B5R or H3L than a reference antibody. For example, an antibody or subsequence thereof can have more or less affinity for B5R envelope protein and include a sequence at least 60% or more (e.g., 65%, 70%, 75%, 80%, 85%, 90%, 95%, etc.) identical to any heavy chain variable region sequence set forth as SEQ ID NOs:2, 6 or 12, and a sequence at least 60% or more (e.g., 65%, 70%, 75%, 80%, 85%, 90%, 95%, etc.) identical to any light chain variable region sequence set forth as SEQ ID NOs:4, 8 or 10. An antibody or subsequence thereof can have more or less affinity for H3L envelope protein and include a sequence at least 60% or more (e.g., 65%, 70%, 75%, 80%, 85%, 90%, 95%, etc.) identical to any heavy chain variable region sequence set forth as SEQ ID NO:14, and a sequence at least 60% or more (e.g., 65%, 70%, 75%, 80%, 85%, 90%, 95%, etc.) identical to any light chain variable region sequence set forth as SEQ ID NO:16.

Antibodies may have the same or substantially the same binding specificity as the exemplified antibodies and subsequences thereof. Thus, a given antibody (e.g., B5R or H3L) may inhibit or compete for binding of another antibody to B5R or H3L, for example, inhibiting binding by at least 30%, at least 35%, at least 40%, at least 45%, at least 50%, at least 55%, at least 60%, at least 65%, at least 70%, at least 75%, at least 80%, at least 85%, at least 90%, or at least 95%, or more of C12, C14, C18, B96, B116, B126 or D67 antibodies. A given B5R or H3L antibody may not detectably compete with or inhibit binding of another antibody to B5R or H3L where the antibodies bind to regions of B5R or H3L that do not interfere with each other. Accordingly, antibodies and subsequences thereof that have substantially the binding specificity as antibodies and subsequences thereof that include a sequence at least 60% or more (e.g., 65%, 70%, 75%, 80%, 85%, 90%, 95%, etc.) identical to any heavy chain variable region sequence set forth as SEQ ID NOs:2, 6 or 12, and a sequence at least 60% or more (e.g., 65%, 70%, 75%, 80%, 85%, 90%, 95%, etc.) identical to any light chain variable region sequence set forth as SEQ ID NOs:4, 8 or 10 are included, as are antibodies and subsequences thereof that have substantially the binding specificity as antibodies and subsequences thereof that include a sequence at least 60% or more (e.g., 65%, 70%, 75%, 80%, 85%, 90%, 95%, etc.) identical to any heavy chain variable region sequence set forth as SEQ ID NO:14, and a sequence at least 60% or more (e.g., 65%, 70%, 75%, 80%, 85%, 90%, 95%, etc.) identical to any light chain variable region sequence set forth as SEQ ID NO:16 are included.

To obtain antibodies that have the same or similar binding specificity as another antibody, antibodies that compete for the binding of the antibody to a target antigen (e.g., B5R or H3L) are screened using a conventional competition binding assay. Screened antibodies can be characterized by any method known in the art, and affinity or specificity, determined by competitive binding, for example, blocking or binding inhibition assays. Antibodies that have the same or similar binding specificity are those that compete for binding to the target antigen (e.g., B5R, B6 or H3L). Because the binding affinity of antibodies may differ, the antibodies will vary in their ability to compete for binding to antigen and may provide greater or less effectiveness for treatment as compared to other antibodies or VIG.

Invention antibodies therefore include human, humanized and chimeric antibodies having the same or different binding affinity for B5R or H3L or homolog thereof and having the same or a different binding specificity for B5R or H3L or homolog thereof. For example, a B5R or homolog antibody of the invention may have an affinity greater or less than 2-5, 5-10, 10-100, 100-1000 or 1000-10,000 fold affinity or any numerical value or range or value within such ranges, as another B5R antibody, for example, of C12, C14, C18, B96, or B116 antibody. Likewise, an H3L or homolog antibody of the invention may have an affinity greater or less than 2-5, 5-10, 10-100, 100-1000 or 1000-10,000 fold affinity or any numerical value or range or value within such ranges, as another H3L antibody, for example, D67 antibody. Antibodies of the invention therefore include human, humanized and chimeric antibodies having the same or different binding affinity or the same or different binding specificity, or function or activity (e.g., anti-poxvirus activity), as human polyclonal H3L, B5R or H3L or B5R protein homolog binding antibodies, as set forth herein.

Exemplary antibody binding affinities for a target antigen (e.g., B5R or H3L) have a dissociation constant ($K_d$) less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M. Typically, binding affinities ($K_d$) for B5R or H3L will be less than $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M.

At least a part of binding affinity for a target antigen (e.g., B5R or H3L) can be when the antibody has less affinity for target antigen (e.g., B5R or H3L) than a reference antibody, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or less (e.g., $K_d$) affinity, or any numerical value or range of values within such ranges, for example, of C12, C14, C18, B96, B116, B126, or D67 antibody. At least a part of binding affinity for target antigen (e.g., B5R or H3L) can be when the antibody has more affinity for the target antigen (e.g., B5R or H3L) than a reference antibody, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or more (e.g., $K_d$) affinity, or any numerical value or range of values within such ranges, for example, of C12, C14, C18, B96, B116, B126, or D67 antibody.

Binding affinity can be determined by association ($K_a$) and dissociation ($K_d$) rate. Equilibrium affinity constant, K, is the ratio of $K_a/K_d$. An antibody having the same binding affinity as another antibody, means that the dissociation constant ($K_d$) of each antibody is within about 1 to 10 fold (1-10 fold greater affinity or 1-10 fold less affinity, or any numerical value or range or value within such ranges, than the reference antibody). An antibody having "substantially the same" binding affinity as another antibody, means that the dissociation constant ($K_d$) of each antibody is within about 10 to 1000 fold (10-1000 fold greater affinity or 1-1000 fold less affinity), for example, of C12, C14, C18, B96, B116, B126, or D67 antibody.

Association ($K_a$) and dissociation ($K_d$) rates can be measured using surface plasmon resonance (SPR) (Rich and Myszka, *Curr. Opin. Biotechnol.* 11:54 (2000); Englebienne, *Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)).

Antibodies include those that have at least a part of an "activity" or "function" as the reference antibody, for example, binding affinity (e.g., $K_d$), binding specificity, or protection from or decreasing susceptibility to, or decreasing or preventing an adverse side effect or complication associated with or caused by poxvirus infection or pathogenesis or vaccination or immunization with a vaccinia virus or against poxvirus. Thus, an antibody having an activity of a B5R or H3L binding antibody has at least a part of one or more activities of the B5R or H3L binding antibodies, such as anti-poxvirus activity in vivo or in vitro, complement fixation, destruction of VACV infected cells by complement, etc.

The term "at least a part" means that the antibody may have less activity but the antibody retains at least a measurable or detectable amount of the activity of the reference antibody, e.g., at least partial binding affinity for B5R or H3L, at least partial protection from or decreasing susceptibility to, or decreasing or preventing an adverse side effect or complication associated with or caused by poxvirus infection or pathogenesis or vaccination or immunization with a vaccinia virus, vaccinia virus protein, against poxvirus, etc. B5R or H3L antibodies having at least a part of one or more activities or functions of the B5R or H3L binding antibodies and subsequences thereof exemplified herein may also have a greater activity than a reference antibody, such as one or more of the B5R or H3L binding antibodies and subsequences thereof exemplified herein. Invention antibodies include antibodies having either or both of antibody-dependent cell-mediated cytotoxicity (ADCC) and complement-mediated cytotoxicity (CDC) activities.

Antibodies having an activity or function of B5R or H3L binding antibodies can be identified through various methods disclosed herein or known in the art. For example, binding assays against B5R or H3Lon plates or (ELISA), on cells (cell based ELISA), and specific inhibition of antibody binding to B5R or H3L can be used as a measure of binding specificity as well as affinity. Additional assays include in vitro binding of vaccinia or poxvirus infected cells, neutralization assays with poxvirus (e.g., vaccinia virus), complement-dependent virus neutralization assay, comet-tail inhibition, as well as in vivo animal protection and other assays as set forth in Examples 4 to 7 and 10 in order to ascertain and compare antibodies for the ability to provide animals with protection against or protect or decrease susceptibility of vaccinia virus infection or pathogenesis, etc.

Methods of producing B5R and H3L binding antibodies are disclosed herein or known in the art. B5R and H3L binding polyclonal antibodies can be obtained by affinity purification of B5R or H3L antibodies from vaccinia immune globulin (VIG) from vaccinia virus or from B5R, H3L or B5R or H3L homolog immunized animals. Human VIG can be used as a source for human polyclonal B5R and H3L antibodies.

B5R and H3L binding monoclonal antibodies can be generated using techniques including conventional hybridoma technology, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). B5R and H3L binding monoclonal antibodies can also be obtained by direct cloning of immunoglobulin sequences from animals, including primate or human subjects that have been exposed to a poxvirus, or vaccinated or immunized with live or attenuated vaccinia virus or poxvirus protein.

Specific hybridomas that produce antibodies of the invention have been deposited with ATCC. In particular, hybridoma cell line 131C14AA (also referred to as C14), which produces an anti-B5R antibody, was deposited on Sep. 25, 2007, and has a deposit designation of PTA-8654 (ATCC University Blvd., Manassas, Va. 20110-2209); hybridoma cell line 131C18 (also referred to as C18), which produces an anti-B5R antibody, was deposited on Aug. 22, 2007, and has a deposit designation of PTA-8562 (ATCC 10801 University Blvd., Manassas, Va. 20110-2209); hybridoma cell line 131C12AA (also referred to as C12), which produces an anti-B5R antibody, was deposited on Sep. 25, 2007, and has a deposit designation of PTA-8653 (ATCC 10801 University Blvd., Manassas, Va. 20110-2209); and hybridoma cell line 130D67 (also referred to as D67), which produces an anti-H3L antibody, was deposited on Aug. 22, 2007, and has a deposit designation of PTA-8564 (ATCC 10801 University Blvd., Manassas, Va. 20110-2209).

Animals may be immunized with B5R, H3L or B5R or H3L homologs, including mice, rabbits, rats, sheep, cows or steer, sheep, goats, pigs, horse, guinea pigs, and primates including humans, in order to obtain antibodies that bind to B5R, H3L or B5R or H3L homolog. Such animals include genetically modified non-human animals having human IgG gene loci (e.g., lambda or kappa light chain), which are capable of expressing human antibodies. Conventional hybridoma technology using splenocytes isolated from immunized animals that respond to the antigen and fused with myeloma cells can be used to obtain human monoclonal antibodies. A specific non-limiting example is the human transchromosomic KM Mice™ (Tomizuka et al., *Proc. Natl. Acad. Sci. USA* 97:722 (2000); and Ishida et al., *Cloning Stem Cells* 4:91 (2004)) which can produce human immunoglobulin genes (WO02/43478) or HAC mice (WO02/092812). Transgenic animals with one or more human immunoglobulin genes (kappa or lambda) that do not express endogenous immunoglobulins are described, for example in, U.S. Pat. No. 5,939,598. Such animals can therefore be used to produce human antibodies in accordance with the invention compositions and methods. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13:65 (1995)).

Antigen (e.g., B5R or H3L) suitable for generating antibodies can be produced by any of a variety of standard protein purification or recombinant expression techniques known in the art. For example, B5R or H3L or subsequences thereof can be produced by standard peptide synthesis techniques, such as solid-phase synthesis. A portion of the protein may contain an amino acid sequence such as a T7 tag or polyhistidine sequence to facilitate purification of expressed or synthesized B5R or H3L sequence. B5R or H3L encoding nucleic acid may be expressed in a cell and protein produced by the cells purified or isolated. B5R or H3L may be expressed as a part of a larger protein by recombinant methods.

Forms of antigen (e.g., B5R and H3L) suitable for generating an immune response include peptide subsequences of full length antigen (e.g., B5R and H3L), which typically comprise four to five or more amino acids. Additional forms of antigen (e.g., B5R and H3L) include preparations or extracts (such as live or attenuated vaccinia virus, e.g., modified vaccinia Ankara (MVA), vaccinia virus Lister strain, vaccinia virus LC16m8 strain, vaccinia virus NYCBOH strain, vaccinia virus Wyeth strain or vaccinia virus prepared from calf lymph, Dryvax®), partially purified antigen (e.g., B5R and H3L) as well as host cells or viruses that express antigen (e.g., B5R and H3L) and preparations or mixtures of such antigen (e.g., B5R and H3L) expressing cells or viruses.

To increase the immune response, antigen (e.g., B5R and H3L) can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen (e.g., B5R and H3L) preparation, and may be at regular or irregular intervals.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805

(1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

The invention also provides nucleic acids encoding B5R or H3L binding antibodies. In one embodiment, a nucleic acid encodes a sequence at least 60% or more (e.g., 65%, 70%, 75%, 80%, 85%, 90%, 95%, etc.) identical to any heavy chain variable region sequence set forth as SEQ ID NOs:2, 6 or 12 or a sequence set forth as SEQ ID NOs:4, 8 or 10. In another embodiment, a nucleic acid encodes a sequence at least 60% or more (e.g., 65%, 70%, 75%, 80%, 85%, 90%, 95%, etc.) identical to any heavy chain variable region sequence set forth as SEQ ID NOs:2, 6 or 12 or a sequence set forth as SEQ ID NOs:4, 8 or 10. In an additional embodiment, a nucleic acid encodes a sequence having one or more amino acid additions, deletions or substitutions of SEQ ID NOs:2, 6 or 12, or SEQ ID NOs:4, 8 or 10. In a further embodiment, a nucleic acid encodes a sequence at least 60% or more (e.g., 65%, 70%, 75%, 80%, 85%, 90%, 95%, etc.) identical to a sequence having one or more amino acid additions, deletions or substitutions of SEQ ID NO:14, or SEQ ID NO:16. In yet another embodiment, a nucleic acid encodes a sequence having one or more amino acid additions, deletions or substitutions of SEQ ID NO:14, or SEQ ID NO:16. In particular aspects, a nucleic acid encodes SEQ ID NOs:2, 6 or 12; or SEQ ID NOs:4, 8 or 10; SEQ ID NO:14; or SEQ ID NO:16, and subsequences thereof.

The terms "nucleic acid" and "polynucleotide" and the like refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths. Shorter polynucleotides are commonly referred to as "oligonucleotides" or "probes" of single- or double-stranded DNA. However, there is no upper limit to the length of such oligonucleotides.

Nucleic acids include sequences that are complementary and sequences that specifically hybridize to SEQ ID NOs:1, 3, 5, 7, 9, or 11; or SEQ ID NOs:13 or 15, or a complementary or antisense sequence thereof.

The term "complementary" or "antisense" refers to a polynucleotide or peptide nucleic acid capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target a protein transcript that participates in metabolism, catabolism, removal or degradation of glycogen from a cell (e.g., mRNA). Antisense molecules are typically 95-100% complementary to the sense strand but can be "partially" complementary, in which only some of the nucleotides bind to the sense molecule (less than 100% complementary, e.g., 95%, 90%, 80%, 70% and sometimes less), or any numerical value or range within or encompassing such percent values.

The term "hybridize" and grammatical variations thereof refer to the binding between nucleic acid sequences. Hybridizing sequences will generally have more than about 50% complementary to a nucleic acid that encodes an amino acid sequence of a reference (e.g., B5R or H3L heavy or light chain variable region) sequence. The hybridization region between hybridizing sequences typically is at least about 12-15 nucleotides, 15-20 nucleotides, 20-30 nucleotides, 30-50 nucleotides, 50-100 nucleotides, 100 to 200 nucleotides or more, or any numerical value or range within or encompassing such lengths.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode SEQ ID NOs:2, 6 or 12; or SEQ ID NOs:4, 8 or 10; SEQ ID NO:14; or SEQ ID NO:16, and subsequences thereof.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid may be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding B5R or H3L binding antibody or antigen (e.g., B5R or H3L) in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of B5R and H3L binding antibodies as well as antigen (e.g., B5R or H3L).

Nucleic acids encoding variable regions of B5R or H3L antibody heavy and light chains, or encoding full length B5R or H3L antibody heavy and light chains can be produced synthetically or using recombinant methods, or isolated from a cell such as a hybridoma. Isolated nucleic acids may be inserted into a suitable expression vector, and introduced into suitable host cells (e.g., CHO, plant and other cells) which can be cultured for the production of recombinant B5R or H3L antibodies.

In accordance with the invention, there are provided host cells that express or are transformed with a nucleic acid that encodes a B5R or H3L antibody of the invention. Host cells include but are not limited to prokaryotic and eukaryotic cells such as bacteria, fungi (yeast), plant, insect, and animal (e.g., mammalian, including primate and human) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression.

The cells may be a primary cell isolate, cell culture (e.g., passaged, established or immortalized cell line), or part of a plurality of cells, or a tissue or organ ex vivo or in a subject (in vivo). In particular embodiments, a cell is a hyperproliferative cell, a cell comprising a cellular hyperproliferative disorder, an immortalized cell, neoplastic cell, tumor cell or cancer cell.

The term "transformed" or "transfected" when use in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the cell and progeny thereof. The cell(s) can be propagated and the introduced protein expressed, or nucleic acid transcribed. A progeny of a transfected or transformed cell may not be identical to the parent cell, since there may be mutations that occur during replication.

Introduction of protein and nucleic acid into target cells (e.g., host cells) can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles."

Accordingly, viral and non-viral vector means of delivery into cells, tissue or organs, in vitro, in vivo and ex vivo are included.

In accordance with the invention, there are provided methods for providing a subject with protection against poxvirus infection or pathogenesis. In one embodiment, a method includes administering an amount of an antibody that binds to B5R or H3L envelope protein sufficient to provide the subject with protection against poxvirus infection or pathogenesis.

Also provided are methods for protecting or decreasing susceptibility of a subject to a poxvirus infection or pathogenesis. In one embodiment, a method includes administering an amount of an antibody that binds to B5R or H3L envelope protein sufficient to protect or decrease susceptibility of the subject to poxvirus infection or pathogenesis.

Additionally provided are methods for decreasing or preventing an adverse side effect or complication associated with or caused by vaccination or immunization with a vaccinia virus, a vaccinia virus protein, a poxvirus or a poxvirus protein. In one embodiment, a method includes administering a composition comprising an amount of an antibody that binds B5R or H3L envelope protein to a subject sufficient to decrease or prevent an adverse side effect or complication associated with or caused by vaccination or immunization with a vaccinia virus (live or attenuated) a vaccinia virus protein or a poxvirus or poxvirus protein. In various aspects, adverse side effects or complications decreased or prevented include adverse side effect or complication comprises: fever, rash, pustules or pocks, generalized vaccinia, progressive vaccinia, postvaccinial encephalitis, vaccinia keratitis, eczema vaccinatum, peri-ocular infection or accidental infection of close contacts. In additional aspects, the subject is a candidate for or has been vaccinated with vaccinia virus, live or attenuated, a vaccinia virus protein, or a poxvirus or poxvirus protein. In other aspects, a subject is administered an antibody that binds B5R or H3L envelope protein or B5R or H3L envelope protein prior to, concurrently with, following or within 1-2, 2-4, 4-12 or 12-24 hours of vaccination or immunization with vaccinia virus, a vaccinia virus protein, or a poxvirus or poxvirus protein.

Further provided are methods for decreasing or preventing an adverse side effect or complication in an immune-suppressed subject (e.g., a subject with or at risk of immunodeficiency, such as an HIV-positive subject) associated with or caused by vaccination with a vaccinia virus, live or attenuated, or a vaccinia virus protein, or a poxvirus or poxvirus protein. In one embodiment, a method includes administering a composition comprising an amount of an antibody that binds B5R or H3L envelope protein to the subject sufficient to decrease or prevent an adverse side effect or complication associated with or caused by vaccination with a Vaccinia virus.

Methods of the invention may be practiced prior to, concurrently with, or following poxvirus infection, contact with or exposure to a poxvirus, or vaccination or immunization with a vaccinia virus, a vaccinia virus protein or a poxvirus or poxvirus protein. Methods of the invention may be practiced prior to, concurrently with, or following a poxvirus infection, contact with or exposure to a poxvirus, or vaccination with vaccinia virus, a vaccinia virus protein or immunization against a poxvirus or with a poxvirus protein.

Invention antibodies and methods include antibodies, subsequences thereof and methods that provide a subject with partial or complete protection against poxvirus infection or pathogenesis, or a reduction, inhibition, delay, decrease or prevention of a symptom of poxvirus exposure, infection or pathogenesis. Invention antibodies and methods include antibodies, subsequences thereof and methods that protect or decrease susceptibility of a subject, at least partially or completely, to a poxvirus infection or pathogenesis, or reduction, inhibition, delay, decrease or prevention of a symptom of poxvirus infection or pathogenesis. Exemplary symptoms include, for example, high fever, fatigue, headache, backache, malaise, rash (maculopapular, vesicular or pustular) or lesions, viremia, delirium, vomiting, diarrhea, and excess bleeding. Antibody activity and methods of the invention can include any reduction, inhibition, delay, decrease or prevention in the onset, progression, severity, duration, frequency or probability of one or more symptoms associated with or caused by a poxvirus infection or pathogenesis, as set forth herein or known in the art, or a subjective or objective detectable or measurable improvement or benefit to the subject.

Invention antibodies and methods are applicable to vaccinia viruses and poxviruses generally, more specifically, members of the viral family Poxyiridae. Poxviruses can be infectious or pathogenic, or non-infectious or non-pathogenic. Specific non-limiting examples of pathogenic poxviruses include variola major and variola minor smallpox viruses. Additional specific non-limiting examples of pathogenic poxviruses include monkeypox, cowpox, Molluscum Contagiosum and camelpox. Vaccinia viruses are poxviruses that may be infectious or pathogenic, live or attenuated. Vaccinia viruses may be non-pathogenic, but may be infectious. Non-limiting examples of vaccinia virus express an H3L envelope protein. Typically, non-infectious live or attenuated vaccinia viruses are used to immunize human subjects against variola major and variola minor smallpox virus and related species of poxviruses. Examples of such vaccinia viruses include modified vaccinia Ankara (MVA), vaccinia virus Lister strain, vaccinia virus LC16m8 strain, vaccinia virus NYCBOH strain, vaccinia virus Wyeth strain or vaccinia virus Dryvax®. For example, $VACV_{WR}$ and $VACV_{IHD-J}$ are pathogenic in mice. Other non-limiting examples of Poxyiridae express homologs to H3L protein, which are proteins having significant sequence identity or similarity to H3L protein set forth as SEQ ID NO:31. H3L homologs can or are very likely to bind to an antibody that binds to H3L protein due to significant sequence identity or similarity.

Methods for treating poxvirus infection or pathogenesis of a subject, include administering to the subject an amount of an antibody that specifically binds B5R or H3L protein sufficient to treat poxvirus infection or pathogenesis. In various embodiments, a method provides a subject with protection against poxvirus infection or pathogenesis, protects or decreases susceptibility of a subject to poxvirus infection or pathogenesis, and decreases or prevents an adverse side effect or complication associated with or caused by vaccination or immunization with a vaccinia virus or vaccinia virus protein, or a poxvirus or poxvirus protein. In the methods of the invention, antibody can be administered alone or in combination with other therapeutics (e.g., other antibodies, such as a B5R and H3L binding antibody combination, or VIG) prior to, concurrently with, or following, exposure to or contact with poxvirus, or poxvirus infection or pathogenesis. The antibody can be administered alone or in combination with other therapeutics (e.g., other antibodies, such as a B5R and H3L binding antibody combination, VIG or a poxvirus protein) prior to, concurrently with, or following, vaccination or immunization with a vaccinia virus, a vaccinia virus protein, or a poxvirus or poxvirus protein. Thus, prophylactic as well as therapeutic methods are provided.

Methods of the invention include methods in which treatment results in any beneficial effect, which is also considered therapeutic. Particular non-limiting examples of beneficial effects which are also considered therapeutic include reducing, decreasing, inhibiting, delaying or preventing poxvirus infection or pathogenesis, or poxvirus titer, proliferation or replication. Additional non-limiting particular examples of beneficial effects include reducing, decreasing, inhibiting, delaying, ameliorating or preventing onset, progression, severity, duration, frequency, probability or susceptibility of a subject to poxvirus infection or pathogenesis, one or more adverse symptoms or complications associated with poxvirus infection or pathogenesis, accelerating or facilitating or hastening recovery of a subject from poxvirus infection or pathogenesis or one or more symptoms thereof, or decreasing, preventing, reducing, inhibiting, or delaying an adverse side effect or complication associated with or caused by vaccination or immunization with a vaccinia virus, a vaccinia virus protein, a poxvirus, etc.

Methods of the invention therefore include providing a beneficial or therapeutic effect to a subject, for example, reducing, decreasing, inhibiting, delaying, ameliorating or preventing onset, progression, severity, duration, frequency or probability of one or more symptoms or complications associated with poxvirus infection or pathogenesis; reducing, decreasing, inhibiting, delaying or preventing increases in poxvirus titer, replication, proliferation, or an amount of a viral protein of one or more poxvirus strains or isolates or subtypes. Stabilizing the infection, pathogenesis, condition or symptom, or preventing or inhibiting or delaying a worsening or progression of the infection, pathogenesis, condition or a symptom or complication associated with poxvirus infection or pathogenesis, are also included in various embodiments of the methods of the invention.

Symptoms or complications associated with poxvirus infection and pathogenesis whose onset, progression, severity, frequency, duration or probability can be reduced, decreased inhibited, delayed ameliorated or prevented include, for example, high fever, fatigue, headache, backache, malaise, rash (maculopapular, vesicular or pustular) or lesions, delirium, vomiting, diarrhea, and excess bleeding. Other symptoms of poxvirus infection or pathogenesis, including variola major and variola minor smallpox virus, monkeypox, cowpox, molluscum contagiosum and camelpox, are known in the art and treatment thereof in accordance with the invention is provided.

In one embodiment, a method includes administering to the subject an amount of an antibody that specifically binds to B5R or H3L envelope protein sufficient to inhibit virus infection or pathogenesis. In additional embodiments, methods of the invention provide a subject with protection against poxvirus infection or pathogenesis, protect, reduce, decrease, inhibit or prevent susceptibility of a subject to poxvirus infection or pathogenesis or one or more symptoms thereof, by one or more poxvirus strains or isolates or subtypes or a species of poxvirus. In particular aspects, antibody is administered prior to (prophylaxis), concurrently with or following poxvirus exposure or infection of the subject (therapeutic). Methods of the invention, in particular aspects, provide a beneficial or therapeutic effect which includes, for example, reducing or decreasing or delaying onset, progression, severity, frequency, duration or probability of one or more symptoms or complications of poxvirus infection or pathogenesis, virus titer, proliferation, replication or an amount of a viral protein of one or more poxvirus strains or isolates or subtypes or species, or susceptibility of a subject to infection or pathogenesis by one or more poxvirus strains or isolates or subtypes or species.

The methods of the invention, including treating poxvirus infection or pathogenesis or a symptom or complication associated with or caused by poxvirus infection or pathogenesis, or decreasing or preventing an adverse side effect or complication associated with or caused by immunization or vaccination with a vaccinia virus, vaccinia virus protein, or a poxvirus or poxvirus protein can therefore result in an improvement in the subjects' condition. An improvement can be any objective or subjective reduction, decrease, inhibition, delay, ameliorating or prevention of onset, progression, severity, duration, frequency or probability of one or more symptoms or complications associated with poxvirus infection or pathogenesis, or virus titer, replication, proliferation, or an amount of a viral protein, or an adverse side effect or complication associated with or caused by immunization or vaccination. An improvement can also be reducing or inhibiting or preventing increases in virus titer, replication, proliferation, or an amount of a viral protein of one or more poxvirus strains or isolates or subtypes or species. An improvement can also mean stabilizing the symptom or complication associated with poxvirus infection or pathogenesis, or inhibiting, decreasing, delaying or preventing a worsening or progression of the symptom or complication associated with poxvirus infection or pathogenesis, or progression of the underlying poxvirus infection.

An improvement can therefore be, for example, in any of high fever, fatigue, headache, backache, malaise, rash (maculopapular, vesicular or pustular) or lesions, delirium, vomiting, diarrhea, or excess bleeding, to any degree or for any duration of time.

An improvement can but need not be complete ablation of any particular symptom or all symptoms, adverse side effects or complications associated with or caused by poxvirus exposure, contact, infection or pathogenesis or vaccinia virus, vaccinia virus protein or poxvirus or poxvirus protein immunization or vaccination. Rather, treatment may be any objective or subjective measurable or detectable improvement. For example, an improvement may reduce, delay or stabilize high fever, but may not reduce or stabilize fatigue, headache, backache, malaise, rash (maculopapular, vesicular or pustular) or lesions, delirium, vomiting, diarrhea, or excess bleeding. Thus, a satisfactory clinical endpoint is achieved when there is an incremental improvement or a partial reduction in the subject's condition or an associated symptom or complication, or an inhibition or prevention of worsening or progression of the symptom or condition (stabilizing the infection or pathogenesis, or one or more symptoms, adverse side effects or complications), over a short or long duration (hours, days, weeks, months, etc.).

An improvement also includes reducing or eliminating the need, dosage frequency or amount of an antiviral drug or other agent (e.g., protein, antibody) used for treating a subject having or at risk of having a poxvirus infection, or a symptom or complication associated with poxvirus infection.

Methods for protecting a subject from poxvirus infection, decreasing susceptibility of a subject to poxvirus infection or pathogenesis and accelerating or hastening a subject's recovery from poxvirus infection or pathogenesis by one or more poxvirus strains or isolates or subtypes or species are further provided. In one embodiment, a method includes administering to a subject having or at risk of having poxvirus infection or pathogenesis an amount of an antibody that specifically binds to B5R or H3L protein sufficient to protect the subject from poxvirus infection or pathogenesis, or to decrease susceptibility of the subject to poxvirus infection or pathogenesis. In another embodiment, a method includes administering to the subject an amount of antibody that specifically binds to B5R or H3L protein sufficient to accelerate or hasten a subject's recovery from poxvirus infection.

In invention methods in which improvement is a desired outcome, such as a prophylactic or therapeutic treatment method that provides an objective or subjective benefit as for poxvirus infection or pathogenesis, or an adverse side effect or complication associated with or caused by vaccination or immunization, an antibody can be administered in a sufficient or effective amount. As used herein, a "sufficient amount" or "effective amount" or an "amount sufficient" or an "amount effective" refers to an amount that provides, in single or multiple doses, alone or in combination with one or more other treatments, therapeutic regimens or agents (e.g., a drug), a long term or a short term detectable or measurable improvement or beneficial effect in a given subject of any degree or for any time period or duration (e.g., hours, days, months, years, or cured).

An amount sufficient or an amount effective can but need not be provided in a single administration and can but need not be achieved by a B5R or H3L antibody alone or in combination with each other or another compound, agent, treatment or therapeutic regimen. In addition, an amount sufficient or an amount effective need not be sufficient or effective if given in single or multiple doses without a second or additional compound, agent, treatment or therapeutic regimen, since additional doses, amounts or duration above and beyond such doses, or additional drugs, agents, treatment or therapeutic regimens may be included in order to provide a given subject with a detectable or measurable improvement or beneficial effect.

An amount sufficient or an amount effective need not be prophylactically or therapeutically effective in each and every subject treated, nor a majority of subjects treated in a given group or population. An amount sufficient or an amount effective means sufficiency or effectiveness in a particular subject, not a group or the general population. As is typical for such methods, some subjects will exhibit a greater or lesser response to a treatment method.

Methods of the invention, including, for example, prophylactic and therapeutic treatment methods, are applicable to any poxvirus strain or isolate or subtype or a species of poxvirus, or combination of strains or isolates or subtypes or species of poxviruses. Particular examples are infectious or pathogenic viruses that express B5R or H3L proteins or B5R or H3L homologs, such as a poxviruses expressing a sequence having sufficient sequence homology to B5R or H3L protein so as to bind to an antibody that binds to B5R or H3L protein. Specific non-limiting examples of poxviruses include variola major or variola minor smallpox virus. Additional specific non-limiting examples include monkeypox, cowpox, Molluscum Contagiosum, vaccinia and camelpox.

B5R and H3L antibodies of the invention may be combined with each other as well as other therapeutic agents. B5R and H3L antibodies of the invention may be administered as a combination with each other as well as other therapeutic agents in the methods of the invention. B5R and H3L antibodies of the invention may be administered alone prior to, concurrently with, or following administration with other therapeutic agents or treatment protocol or regimen, such as agents having anti-virus activity. Accordingly, combination compositions including B5R and H3L antibodies, methods of using such combinations, as well as methods in which other compositions are administered prior to, concurrently with or following administration of B5R or H3L antibody, in accordance with the methods of the invention, are provided.

Particular non-limiting examples of such combination compositions and combination methods include pooled monoclonal or pooled polyclonal antibodies containing two or more different antibodies that each bind B5R and H3L protein, having the same or a different binding specificity, binding affinity, or efficacy in inhibiting poxvirus infection of a cell in vitro or poxvirus infection or pathogenesis in vivo. In particular embodiments, a plurality of antibodies (e.g., B5R and H3L antibodies) are administered separately or as a combination composition in accordance with the invention. In further particular embodiments, an additional antibody that binds to a poxvirus protein, different from B5R or H3L binding antibody, is administered separately or as a combination composition with B5R and/or H3L binding antibody in accordance with the invention. In particular aspects, the additional antibody that binds to a poxvirus protein binds to one or more forms, for example, intracellular mature virion (IMV), cell-associated enveloped virion (CEV) or extracellular enveloped virion (EEV) forms of smallpox. In additional particular aspects, the additional antibody that binds to a poxvirus protein binds to vaccinia protein B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog. In a further aspect, an additional antibody can include VIG.

Additional examples of such combination compositions and combination methods include administering separately or as a combination composition in accordance with the invention an additional poxvirus protein. In one particular embodiment, a B5R or H3L binding antibody includes an additional poxvirus protein. In another particular embodiment, a method includes administering an additional poxvirus protein. In particular aspects, the additional poxvirus protein is present on one or more of IMV, CEV or EEV forms of smallpox. In additional particular aspects, the additional poxvirus protein is one or more of vaccinia B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog.

Compositions used in accordance with the invention, as well as methods, can exclude certain components or method steps. In one embodiment, a method in which the composition excludes one or more poxvirus proteins or one or more antibodies that bind to poxvirus proteins is administered. In particular aspects, a composition excludes or does not consist of live or attenuated vaccinia virus (e.g., modified vaccinia Ankara (MVA), vaccinia virus Lister strain, vaccinia virus LC16m8 strain, vaccinia virus NYCBOH strain, vaccinia virus Wyeth strain, vaccinia virus ACAM2000 or vaccinia virus prepared from calf lymph, Dryvax®). In another embodiment, a method excludes administering one or more poxvirus proteins or one or more antibodies that bind to poxvirus proteins different from B5R or H3L protein. In particular aspects, a method excludes administering live or attenuated virus (e.g., poxvirus or modified vaccinia Ankara (MVA), vaccinia virus Lister strain, vaccinia virus LC16m8 strain, vaccinia virus NYCBOH strain, vaccinia virus Wyeth strain or vaccinia virus prepared from calf lymph, Dryvax®) with an antibody that binds to B5R or H3L protein. In additional aspects, a method excludes administering poxvirus protein B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog. In further aspects, a method excludes administering an antibody that binds to poxvirus protein. For example, human or non-human vaccinia immune globulin (VIG) or antibody that binds to B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, H3L, A28, A14, A56, A34, A36, or A2 homolog can be excluded in a method or composition that includes an antibody that binds to B5R or H3L protein.

Subjects appropriate for treatment include those having or at risk of having a poxvirus infection or pathogenesis or at risk of having a poxvirus infection. Target subjects therefore include subjects that have been exposed to or contacted with poxvirus, or that have developed one or more adverse symptoms of poxvirus infection or pathogenesis, regardless of the type, timing or degree of onset, progression, severity, frequency, duration of the symptoms.

Target subjects also include those at risk of poxvirus exposure, contact, infection or pathogenesis or at risk of having or developing any poxvirus infection or pathogenesis. The invention methods are therefore applicable to treating a subject who is at risk of poxvirus exposure, contact, infection or pathogenesis, but has not yet been exposed to or contacted with poxvirus. Prophylactic methods are therefore included. Target subjects for prophylaxis can be at increased risk (probability or susceptibility) of poxvirus exposure, contact, infection or pathogenesis, as set forth herein and known in the art. For example, a subject with acute or chronic immunological susceptibility (e.g., an immune-suppressed, immunocompromised, or HIV-positive subject) is at increased risk of poxvirus infection or pathogenesis.

"Prophylaxis" and grammatical variations thereof mean a method in which contact, administration or in vivo delivery to a subject is prior to contact with or exposure to poxvirus, or vaccination or immunization of a subject against poxvirus or with a vaccinia virus (e.g., an infectious or pathogenic poxvirus or live or attenuated vaccinia virus, or vaccinia Ankara (MVA), vaccinia virus Lister strain, vaccinia virus LC16m8 strain, vaccinia virus NYCBOH strain, vaccinia virus Wyeth strain or vaccinia virus prepared from calf lymph, Dryvax). In certain situations it may not be known that a subject has been contacted with or exposed to poxvirus, or vaccinated or immunized against poxvirus or with a vaccinia virus, but administration or in vivo delivery to a subject can be performed prior to manifestation or onset of poxvirus infection or pathogenesis (or an associated symptom). In either case, a method can eliminate, prevent, inhibit, decrease or reduce the probability of or susceptibility towards developing a symptom of poxvirus infection or pathogenesis, or an adverse side effect or complication associated with or caused by vaccination or immunization of a subject against poxvirus or with a vaccinia virus or a vaccinia virus protein or a poxvirus protein.

At risk subjects appropriate for treatment include subjects exposed to other subjects having any poxvirus. At risk subjects appropriate for treatment therefore include human subjects exposed to or at risk of exposure to other humans that may have a poxvirus infection, or are at risk of a poxvirus infection. At risk subjects appropriate for treatment also include subjects where the risk of poxvirus infection or pathogenesis is increased due to changes in virus infectivity or cell tropism, environmental factors, or immunological susceptibility (e.g., an immune-suppressed, immunocompromised, or HIV-positive subject).

Target subjects further include those at risk of an adverse side effect, complication or reaction associated with or caused by a smallpox vaccination (e.g., a live or attenuated vaccinia virus or a vaccinia virus protein, etc.) or immunization or treatment against small pox (e.g., vaccination or immunization with live or attenuated vaccinia virus or poxvirus, VIG, a vaccinia virus or a poxvirus protein, etc.). Such target subjects include those with atopic dermatitis. Subjects afflicted with atopic dermatitis are at risk of developing eczema vaccinatum when vaccinated or immunized against smallpox.

B5R and H3L antibodies and subsequences thereof can be administered in accordance with the methods as a single or multiple dose e.g., one or more times daily, weekly, monthly or annually or between about 1 to 10 weeks, or for as long as appropriate, for example, to achieve a reduction in the onset, progression, severity, frequency, duration of one or more symptoms or complications associated with poxvirus infection or pathogenesis, or an adverse side effect or complication associated with or caused by vaccination or immunization of a subject with a vaccinia virus, a vaccinia virus protein, or against a poxvirus or with a poxvirus protein.

Doses can vary depending upon whether the treatment is prophylactic or therapeutic, the onset, progression, severity, frequency, duration probability of or susceptibility of the symptom, the type of virus infection or pathogenesis to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a prophylactic or therapeutic benefit.

Typically, for therapeutic treatment, antibodies will be administered as soon as practical, typically within 1-2, 2-4, 4-12, 12-24 or 24-72 hours after a subject is exposed to or contacted with any poxvirus, or within 1-2, 2-4, 4-12, 12-24 or 24-48 hours after development of one or more symptoms associated with poxvirus infection or pathogenesis (e.g., onset of fever or rash) or symptoms associated with pathogenic poxviruses such as smallpox and monkeypox. For prophylactic treatment, antibodies can be administered 0-4 weeks, e.g., 2-3 weeks, prior to exposure to or contact with poxvirus since antibodies are predicted to be effective for at least a month following administration. For prophylactic treatment in connection with vaccination or immunization of a subject with vaccinia virus (live or attenuated), poxvirus or a poxvirus protein, antibodies can be administered prior to, concurrently with or following immunization of the subject. Typically, antibodies are administered concurrently with vaccination or immunization of a subject, but can be administered within 1-2, 2-4, 4-12, 12-24 or 24-48 hours prior to vaccination or immunization or within 1-2, 2-4, 4-12, 12-24 or 24-48 hours following vaccination or immunization.

Doses can be based upon current existing passive immunization protocols (e.g., VIG), empirically determined, determined using animal disease models or optionally in human clinical trials. Initial study doses can be based upon the animal studies set forth herein, for a mouse, which weighs about 20 (15-30) grams, and the amount of antibody administered that is determined to be effective. The dose can be adjusted according to the mass of a subject, and will generally be in a range from about 1-10 μg/kg, 10-25 μg/kg, 25-50 μg/kg, 50-100 μg/kg, 100-500 μg/kg, 500-1,000 μg/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 100 mg/kg.

The dose amount, number, frequency or duration may be proportionally increased or reduced, as indicated by the status of the subject. For example, whether the subject has a poxvirus infection or pathogenesis, whether the subject has been exposed to or contacted with a poxvirus or is merely at risk of poxvirus contact or exposure, or whether the subject is a candidate for or will undergo vaccination or immunization with vaccinia virus (live or attenuated), poxvirus or a poxvirus protein. The dose amount, number, frequency or duration may be proportionally increased or reduced, as indicated by any adverse side effects, complications or other risk factors of the treatment or therapy.

The term "subject" refers to an animal, typically a mammalian animal, such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, the mouse models of poxvirus infection (vaccinia virus) exemplified herein.

B5R and H3L binding antibodies of the invention, including modified forms, variants and subsequences/fragments thereof, and nucleic acids encoding B5R and H3L binding antibodies, can be incorporated into pharmaceutical compositions. Such pharmaceutical compositions are useful for administration to a subject in vivo or ex vivo.

Antibodies can be included in a pharmaceutically acceptable carrier or excipient prior to administration to a subject. As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, ophthalmic, optical, intravenous (i.v.), intramuscular, intraglandular, intraorgan, intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9→2-hydroxy-ethoxy methylguanine, adamantanamine, 5-iodo-2'-deoxyuridine, cidofivir, ST-246, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) $20^{th}$ ed., Mack Publishing Co., Easton, Pa.; *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Antibodies and compositions thereof can be packaged in unit dosage form (capsules, troches, cachets, lozenges, or tablets) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention provides kits comprising B5R and H3L antibodies, combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more B5R and H3L antibodies alone or in combination with an anti-poxvirus agent (e.g., a poxvirus protein or an antibody that binds to a poxvirus protein different than B5R and H3L, VIG, etc.) or drug.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., a diskette, hard disk, ZIP disk, etc.), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or prophylactic or therapeutic regimes described herein. Exemplary instructions include, instructions for treating poxvirus infection or pathogenesis. Kits of the invention therefore can additionally include labels or instructions for practicing any of the methods of the invention described herein including treatment, detection, monitoring or diagnostic methods. Thus, for example, a kit can include an antibody that has one or more anti-poxvirus functions or activities as set forth herein, together with instructions for administering the antibody in a prophylactic or therapeutic treatment method of the invention.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include a growth medium (e.g., for a B5R or H3L binding antibody producing cell line), buffering agent, or a preservative or a stabilizing agent in a pharmaceutical formulation containing a B5R or H3L binding antibody. Each component of the kit can be enclosed within an individual container and all of the various containers can be within a single package. Invention kits can be designed for cold storage. Invention kits can further be designed to contain B5R or H3L binding antibody producing hybridoma or other host cells (e.g., CHO cells). The cells in the kit can be maintained under appropriate storage conditions until the cells are ready to be used. For example, a kit including one or more hybridoma or other cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to a "B5R or B5R homolog binding antibody" or "an H3L or H3L homolog binding antibody" includes a plurality of such antibodies and reference to an "activity or function" such as "an anti-poxvirus activity or function" can include reference to one or more activities or functions, and so forth.

As used herein, all numerical values or ranges include fractions of the values and integers within such ranges and fractions of the integers within such ranges unless the context clearly indicates otherwise. Thus, to illustrate, reference to a numerical range, such as a percentage range, 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. For example, in certain embodiments or aspects of the invention, antibodies or subsequences that specifically bind to poxvirus proteins are excluded. In certain embodiments and aspects of the invention, poxvirus proteins are excluded. Thus, even though the invention is generally not expressed herein in terms of what the invention does not include embodiments and aspects that expressly exclude compositions (e.g., poxvirus antibodies or proteins) and method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Antigen Preparation

Baculovirus expressed vaccinia B5R recombinant protein: DNA was isolated from $5\times10^6$ vaccinia virus infected Hela cells using the QIAamp DNA Mini Kit (QIAGEN Inc., Valencia, Calif.) following manufacturer's instructions. The sequence encoding the extracellular domain of vaccinia B5R was amplified by reverse-transcription polymerase chain reaction using primers B5R-Ftopo dir gate and B5R-Rtopo dir gate (Table 1). The product was sub-cloned into the pENTR™/D-TOPO® Gateway entry vector (Invitrogen Corp, Carlsbad, Calif.). The cloned PCR amplified product was sequenced and confirmed to be identical to the published sequence of vaccinia B5R WR stain (SEQ NO:28). Recombinant baculovirus were generated that encoded the C-terminal 6×His tagged vaccinia B5R protein (B5R-His) by performing the recombination reaction between the Gateway pENTR™/D-TOPO B5R-His and the Gateway BaculoDirect tm C-term linear DNA (Invitrogen Corp, Carlsbad, Calif.). *Trichoplusia ni* High-Five BTI-TN-5b1-4 (Tn5) insect cells (Invitrogen Corp.) were infected with the B5R-His recombinant baculovirus for protein production.

The nucleotide sequence of vaccinia B5R-6×His protein from initiation codon (ATG) to 6×His tag (bold) is as follows (SEQ ID NO:69):

```
ATGAAAACGA TTTCCGTTGT TACGTTGTTA TGCGTACTAC CTGCTGTTGT TTATTCAACA  60
TGTACTGTAC CCACTATGAA TAACGCTAAA TTAACGTCTA CCGAAACATC GTTTAATAAT 120
AACCAGAAAG TTACGTTTAC ATGTGATCAG GGATATCATT CTTCGGATCC AAATGCTGTC 180
TGTGAAACAG ATAAATGGAA ATACGAAAAT CCATGCAAAA AAATGTGCAC AGTTTCTGAT 240
TACATCTCTG AACTATATAA TAAACCGCTA TACGAAGTGA ATTCCACCAT GACACTAAGT 300
TGCAACGGCG AAACAAAATA TTTTCGTTGC GAAGAAAAAA ATGGAAATAC TTCTTGGAAT 360
GATACTGTTA CGTGTCCTAA TGCGGAATGT CAACCTCTTC AATTAGAACA CGGATCGTGT 420
CAACCAGTTA AAGAAAAATA CTCATTTGGG GAATATATAA CTATCAACTG TGATGTTGGA 480
TATGAGGTTA TTGGTGCTTC GTACATAAGT TGTACAGCTA ATTCTTGGAA TGTTATTCCA 540
TCATGTCAAC AAAAATGTGA TATACCGTCT CTATCTAATG GATTAATTTC CGGATCTACA 600
TTTTCTATCG GTGGCGTTAT ACATCTTAGT TGTAAAAGTG GTTTTATACT AACGGGATCT 660
CCATCATCCA CATGTATCGA CGGTAAATGG AATCCCATAC TCCCAACATG TGTACGATCT 720
AACGAAAAAT TTGATCCAGT GGATGATGGT CCCGACGATG AGACAGATTT GAGCAAACTC 780
TCGAAAGACG TTGTACAATA TGAACAAGAA ATAGAATCGT TAGAAAAGGG TGGGCGCGCC 840
GACCCAGCTT TCTTGTACAA AGTGGTGAGA ATGAATGAAG ATCTGGGGAA GCCTATCCCT 900
AACCCTCTCC TCGGTCTCGA TTCTACGCGT ACCGGTCATC ATCACCATCA CCATTGA     960
```

The amino acid sequence of vaccinia virus B5R 6×His protein, signal peptide (bold) and 6×His (underlined) is as follows (SEQ ID NO:70):

```
MKTISVVTLL CVLPAVVYST CTVPTMNNAK LTSTETSFNN NQKVTFTCDQ GYHSSDPNAV   1
CETDKWKYEN PCKKMCTVSD YISELYNKPL YEVNSTMTLS CNGETKYFRC EEKNGNTSWN  60
DTVTCPNAEC QPLQLEHGSC QPVKEKYSFG EYITINCDVG YEVIGASYIS CTANSWNVIP 120
SCQQKCDIPS LSNGLISGST FSIGGVIHLS CKSGFILTGS PSSTCIDGKW NPILPTCVRS 180
NEKFDPVDDG PDDETDLSKL SKDVVQYEQE IESLEKGGRA DPAFLYKVVR MNEDLGKPIP 240
NPLLGLDSTR TGHHHHHH                                              300
```

Bacterially Expressed Recombinant H3L Protein:

The DNA from cells infected with the vaccinia virus that was used for B5R cloning above, was likewise used as a PCR template for cloning full length H3L. The sequence encoding the full-length open reading frame of vaccinia H3L was amplified by reverse-transcription polymerase chain reaction using primers H3L F NdeI pET-15b and H3L R Bam HI pET-15b (Table 1). As a cloning intermediate, this PCR product was cloned into the TA-topo 2.1 vector following manufacturers instructions (Invitrogen, Carlsbad Calif.). This H3L-TA-topo2.1 plasmid was then used as a template for PCR using primers H3L NheI fwd pET28 and H3L XhoI rev pET28 (Table 1). The amplified full-length PCR product was digested with NheI and XhoI and ligated into the NheI and XhoI sites of the bacterial expression vector pET28a to create pET28a-full length H3L-His, which encodes a H3L with a C-terminal 6×His tag. The nucleotide sequence of vaccinia H3L-6×His protein from initiation codon (ATG) to 6×His tag (bold) is as follows (SEQ ID NO:71):

```
ATGGCTAGCG CGGCGGCGAA AACTCCTGTT ATTGTTGTGC CAGTTATTGA TAGACTTCCA   60
TCAGAAACAT TTCCTAATGT TCATGAGCAT ATTAATGATC AGAAGTTCGA TGATGTAAAG  120
GACAACGAAG TTATGCCAGA AAAAAGAAAT GTTGTGGTAG TCAAGGATGA TCCAGATCAT  180
TACAAGGATT ATGCGTTTAT ACAGTGGACT GGAGGAAACA TTAGAAATGA TGACAAGTAT  240
ACTCACTTCT TTTCAGGGTT TTGTAACACT ATGTGTACAG AGGAAACGAA AAGAAATATC  300
GCTAGACATT TAGCCCTATG GGATTCTAAT TTTTTTACCG AGTTAGAAAA TAAAAAGGTA  360
GAATATGTAG TTATTGTAGA AAACGATAAC GTTATTGAGG ATATTACGTT TCTTCGTCCC  420
GTCTTGAAGG CAATGCATGA CAAAAAAATA GATATCCTAC AGATGAGAGA AATTATTACA  480
GGCAATAAAG TTAAAACCGA GCTTGTAATG GACAAAAATC ATGCCATATT CACATATACA  540
GGAGGGTATG ATGTTAGCTT ATCAGCCTAT ATTATTAGAG TTACTACGGA GCTGAACATC  600
GTAGATGAAA TTATAAAGTC TGGAGGTCTA TCATCGGGAT TTTATTTTGA AATAGCCAGA  660
ATTGAAAACG AAATGAAGAT CAATAGGCAG ATACTGGATA ATGCCGCCAA ATATGTAGAA  720
CACGATCCCC GACTTGTTGC AGAACACCGT TTCGAAAACA TGAAACCGAA TTTTTGGTCT  780
AGAATAGGAA CGGCAGCTAC TAAACGTTAT CCAGGAGTTA TGTACGCGTT TACTACTCCA  840
CTGATTTCAT TTTTTGGATT GTTTGATATT AATGTTATAG GTTTGATTGT AATTTTGTTT  900
ATTATGTTTA TGCTCATCTT TAACGTTAAA TCTAAACTGT TATGGTTCCT TACAGGAACA  960
TTCGTTACCG CATTTATCCT CGAGCACCAC CACCACCACC ACTGA                1020
```

The amino acid sequence of vaccinia virus H3L-His protein and 6×His (underlined) is as follows (SEQ ID NO:72):

```
MASAAAKTPV IVVPVIDRLP SETFPNVHEH INDQKFDDVK DNEVMPEKRN VVVVKDDPDH   60
YKDYAFIQWT GGNIRNDDKY THFFSGFCNT MCTEETKRNI ARHLALWDSN FFTELENKKV  120
EYVVIVENDN VIEDITFLRP VLKAMHDKKI DILQMREIIT GNKVKTELVM DKNHAIFTYT  180
GGYDVSLSAY IIRVTTELNI VDEIIKSGGL SSGFYFEIAR IENEMKINRQ ILDNAAKYVE  240
HDPRLVAEHR FENMKPNFWS RIGTAATKRY PGVMYAFTTP LISFFGLFDI NVIGLIVILF  300
IMFMLIFNVK SKLLWFLTGT FVTAFILEHH HHHH
```

H3L production and protein purification: To produce H3L-His in bacteria, the expression vector pET28a-full length H3L-His was transformed into BL21 (DE3) pLysS competent cells and bacterial cultures were induced to express H3L-His by a 2 hr. incubation of diluted (1:20) overnight cultures in 1 mM IPTG (sopropyl-beta-D-thiogalactopyranoside). Cells were harvested by centrifugation for protein purification. Recombinant full-length H3L with N-terminal HisTag® was purified by metal chelate affinity chromatography with Ni Sepharose 6 Fast Flow resin (GE Healthcare). Bacterial cells were lysed with microfluidizer (model M10L, Microfluidics, Inc.). Lysis buffer included 0.5% Triton X-100 (Calbiochem), and the chromatography was performed in the presence of appropriate non-ionic detergent, like 0.5% Triton X-100 or 0.58% Octyl Glucoside (Calbiochem). H3L was eluted from the column with 200 mM imidazole, and subsequently dialyzed against 20 mM Na phosphate buffer, pH 8.0, 0.25M NaCl, 10% glycerol, and appropriate detergent (see above). Protein concentration was determined by DC Lowry protein assay (Bio-Rad) using BSA standard (Pierce Biotechnology) in the same buffer.

B5R production and protein purification: B5R-His recombinant protein was generated by infecting 1 liter of insect Tn5 cells with B5R-His baculovirus for 4 days. Growth media was harvested and clarified by centrifugation. Recombinant B5R-His was purified by metal chelate affinity chromatography with Ni Sepharose 6 Fast Flow resin (GE Healthcare). The baculovirus-infected Tn5 insect cell supernatant was concentrated and diafiltered into PBS by tangential flow filtration using a membrane with 10 kDa molecular weight cut off. B5R was eluted from the column with 200 mM imidazole, and subsequently dialyzed against PBS. Protein concentration was determined by Lowry protein assay (Bio-Rad) using BSA standard (Pierce Biotechnology).

Mice: Human trans-chromosomic KM Mice™ (WO02/43478, WO02/092812, Ishida and Lonberg, IBC's $11^{th}$ Antibody Engineering Meeting. Abstract (2000); and Kataoka, S. IBC's $13^{th}$ Antibody Engineering Meeting. Abstract (2002)) harboring human chromosome fragments encoding the human immunoglobulin region were obtained from Kirin Brewery Co., Ltd., Japan, and were housed in the animal facility at the La Jolla Institute for Allergy and Immunology. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human antibodies and human monoclonal antibodies are described (see, e.g., WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). Development of bovine carrying human immunoglobulin genes, TC cows, is described in Kuroiwa et al., *Nat. Biotechnol.* 20:889 (2002), and Kuroiwa et al., *Nat. Genet.* 36:775 (2004).

Immunization: B5R-His or H3L-His recombinant protein was mixed with an equal volume of complete Freund's adjuvant (CFA, Sigma) and an emulsion was prepared. KM Mice™ were immunized subcutaneously with 25 to 50 μg protein of soluble recombinant B5R-His or H3L-His in CFA/IFA. Mice were boosted subcutaneously with 10 to 20 μg of protein emulsified in incomplete Freund's adjuvant (IFA, Sigma) at 1 to 2 week intervals for 2 boosts. The first boost was with 10% CFA/90% IFA, the second boost was IFA alone. A final intravenous injection of 10 μg of soluble B5R-His or H3L-His without adjuvant was given 3 days prior to fusion.

Hybridoma production: Several of the mice raised anti-B5R or H3L specific antibodies, with a range in human IgG B5R or H3L specific titers. The mice with the highest anti-B5R or anti-H3L IgG specific antibody titer in their serum were selected for production of monoclonal antibodies. Spleens were harvested and single cell suspensions were fused to a myeloma cell line (SP2/O—Ag14) (ATCC, Rockville, Md.) at a ratio of 5:1 with 50% polyethylene glycol (Boehringer Mannheim, Indianapolis, Ind.) to generate human anti-vaccinia B5R or H3L producing hybridomas. The fusions were plated into 96 well flat bottom plates at an optimal density and cultured in complete DMEM-10 medium (Dulbecco's Modified Engle's Medium with 10% fetal bovine serum (FBS, Invitrogen, Corp.), 2 mM L-glutamine, 100 U/ml penicillin, 100 μg/ml streptomycin sulfate (all from BioWhittaker, Walkersville, Md.), HAT supplement (Sigma), and 10% Hybridoma Cloning Factor (HCF, Biovaris, San Diego, Calif.) in a 10% $CO_2$, 37° C. incubator. Approximately 1100 wells from 4 fusions were screened by ELISA for human IgG containing B5R or H3L specific antibodies. Production of human anti-vaccinia B5R or H3L IgG antibodies were confirmed by ELISA. Crude hybridoma supernatant was used for a preliminary evaluation of virus neutralizing activity in vitro. Positive wells were expanded and subjected to 2 to 3 rounds of limiting dilution cloning to obtain monoclonal antibodies.

Antibody protein purification: For antibody purification, hybridomas were cultured in 2 liter roller bottles at 350 milliliter to 1 liter/bottle or in a 1 liter Integra system (INTEGRA Bioscience, Inc. Ijamsville, Md.) with hybridoma-SFM medium (Invitrogen, Corp.) supplemented with ultra low IgG fetal bovine serum (Invitrogen, Corp.) Human monoclonal antibodies were purified from culture media using recombinant Protein A-Sepharose Fast Flow gel (Amersham Biosciences). Conditioned medium generated in roller bottles was first concentrated using an Ultrasette tangential flow system (Pall Corp., East Hills, N.Y.). The conditioned medium was filtered with a 0.22 μm vacuum filter unit (Millipore, Bedford, Mass.) and loaded onto a Protein A-Sepharose Fast Flow column (Amersham Biosciences) of appropriate size for the amount of human antibody in the medium. The column was washed thoroughly with 20 column volumes of PBS and the antibody was eluted with 0.1 M Gly-HCl, pH 3.6, 0.15 M NaCl and neutralized with 1 M Tris-HCl, pH 8.0. The fractions were analyzed by SDS-PAGE and the positive fractions were pooled and concentrated with a centrifugal concentrator (Vivaspin, 50,000 MWCO: Sartorius, Gettingen, Germany). Sephadex G-25 desalting columns, (NAP, Amersham Biosciences), were used for buffer exchange to PBS, pH 7.4. Finally, the antibody was filter sterilized using syringe filters with 0.22 μm pore diameters and the antibody concentration was determined by the Lowry method. Pyrogen content was determined using a *Limulus Amebocyte* Lysate (LAL) assay (Associates of Cape Cod, Falmouth, Mass.). The limits of detection of this assay are 0.06 EU/mg. If the test was negative, the samples were considered endotoxin free.

Human IgG Quantitation ELISA: To determine the amount of human antibody present in supernatants and purified stocks the following protocol was used. Goat anti-human Fcγ specific antibody (Jackson Immunoresearch Laboratories, West Grove, Pa.) was coated to 96 well plates (Nunc, Denmark) in carbonate buffer at 0.5 μg/well for 1 hour at 37° C. The plates were then blocked with Superblock (Pierce, Rockford, Ill.) for 30 minutes followed by addition of the samples to the plates. Standard curves were generated using total human IgG (Sigma) or purified human IgG1 or IgG4 (Kirin Brewery Co., Ltd). The plates were incubated for 1 hour at 37° C., washed in PBS/1% BSA/0.1% Tween20 (Sigma), and the bound antibody was detected with goat anti-human Fcγ specific antibody conjugated to horseradish peroxidase (HRP, Jackson Immunoresearch) for 1 hour at 37° C. The TMB substrate (Sigma) was added for 10 minutes and the reaction was stopped with $H_2SO_4$ (LabChem, Pittsburgh, Pa.). The OD was measured at 450 nm on a microplate reader.

B5R or H3L Specific Antibody Detection ELISA: Antibody titers, specificity, and production by hybridomas were determined by ELISA. In brief, 96 well flat bottom plates were coated with 50 μl of B5R-His or H3L at 5 μg/ml in carbonate buffer (pH 9.4) overnight at 4° C. or at 37° C. for 1 hour. After washing twice with PBS/0.1% Tween 20, plates were blocked with PBS/1% BSA/0.1% Tween20 at 37° C. for 1 hour. The serum, supernatant, or purified antibody was diluted in blocking buffer, added to the wells, and the plates were incubated for 1 hour at 37° C. The plates were washed 4 times with PBS/0.1% Tween 20 and the peroxidase conjugated sheep anti-human kappa detection antibody (The Binding Site, Birmingham, UK) was added at a dilution of 1:2000. Following a 1 hour incubation at 37° C., the plates were washed and the TMB (Sigma) substrate was added and incubated at room temperature for 10 to 30 minutes. The reaction was stopped with $H_2SO_4$ (LabChem) and the optical density was measured at 450 nm by a microplate reader. ELISAs were also performed using whole vaccinia virus antigen from infected cell lysates.

Anti-B5R or H3L Antibody Cross-blocking (Binding Competition) Assays: In order to determine if the antibodies bind the same "epitope" of B5R or H3L an ELISA protocol was used. Nunc 96 well flat bottom ELISA plates were coated with the human anti-B5R or H3L antibodies in carbonate buffer at 2 μg/ml for 1 hour at 37° C. The plates were washed and then blocked with PBS/1% BSA/Tween 20. The human anti-B5R or H3L antibodies were then pre-incubated with recombinant B5R-His or H3L protein for 30 minutes at room temperature. The combinations of antibody-B5R or H3L protein were added to the plate and incubated for 1 hour at 37° C. After 3 washes, bound B5R-His or H3L-His was detected with peroxidase conjugated mouse anti-poly His IgG2a (Clonetech). The ELISA was completed as described above. The percent inhibition was determined using the OD of each sample in the following formula: % inhibition=100−((sample/Maximum binding)*100).

Isolation of Human Anti-B5R or H3L Antibody Genes: Cultured hybridoma cells, which produce either anti-B5R or H3L antibodies were collected by centrifugation. Total RNA was purified from these cells using the RNeasy kit (QIAGEN Inc., Valencia, Calif.) following the manufacturer's instructions. The SMART-RACE cDNA Amplification Kit (Clontech Co., Ltd., Palo Alto, Calif.) was used for cloning of cDNA that encodes the variable region of the immunoglobulin genes from total hybridoma cell RNA. Briefly, first strand cDNA was prepared by reverse transcriptase from 2 microgram of total RNA. This cDNA was used as a template for polymerase chain reaction (PCR) to amplify the variable region and a part of the constant region of heavy and light chains (HV and LV, respectively). The amplified sequences also contained the antibody leader peptide sequences. The reaction was as follows: 2.5 U Pfu Ultra DNA polymerase (Stratagene, La Jolla, Calif.); 0.2 μM 3' Primer (for Heavy chain: IgG1p, for Light chain: hk5, Table 1); 1× Universal Primer Mix A for the 5' end (UMP primer Mix A included in the SMART RACE Kit); 200 μM dNTP mix; 1 mM $MgCl_2$; Pfu Ultra Buffer (final concentration is lx); and cDNA template. The thermocycling program was 5 cycles of: 94° C.×30 sec, 72° C.×3 min. 5 cycles of: 94° C.×30 sec, 70° C.×30 sec, 72° C.×3 min. 25 cycles of: 94° C.×30 sec, 68° C.×30 sec, 72° C.×3 min followed by an extension at 72° C.×7 min. Amplified DNA fragments were collected by agarose gel electrophoresis, and purified using the QIAquick Gel Extraction Kit (Qiagen Co., Ltd., Germany). Purified DNA fragments of HV and LV were integrated into the PCR 4 Blunt-TOPO vector using the Zero Blunt TOPO PCR Cloning Kit (Invitrogen, Carlsbad, Calif.), and each construct plasmid was transformed into *E. coli*. Bacterial colonies were selected and plasmid purified from those containing plasmid with HV or LV sequences. Nucleotide sequences of each insert (HV and LV) in the construct plasmids were analyzed using specific primers (M13F, M13R, Table 1). Based on the sequence obtained from HV and LV, oligonucleotide primers were designed to amplify VH and VL (Table 1).

Anti-B5R 131C12 antibody VH and VL were cloned into the IgG1 mammalian expression vector. Briefly, oligonucleotide primers, containing 5'-SalI and 3'-NheI restriction enzyme recognition sites were designed to amplify the variable region of the Heavy chain (HV) by PCR. PCR was performed using pTopo-VH miniprep DNA as a template and antibody clone 131C12 specific primers 12H FWD SalI and 12H REV NheI (Table 1), with Pfu Ultra DNA polymerase. After digestion of the PCR product with NheI and SalI, a 410 bp fragment was sub-cloned into the IgG1 expression vector (IDEC Pharmaceuticals, San Diego, Calif., N5KG1-Val Lark (a modified vector of N5KG1, U.S. Pat. No. 6,001,358)) that was pre-digested with NheI and SalI (8.9 kilobases DNA fragment). The existence of variable region of the Heavy chain (HV) was analyzed by restriction digest. As the second step, LV was inserted into N5KG1-Val Lark-VH vector as follows: the DNA vector was digested by two DNA restriction enzymes, BglII and BsiWI. The 9.1 kb DNA fragment was isolated. Similarly to the heavy chain construct, a primer set for PCR of LV was designed to contain the recognition sites for 5'BglI and 3'BsiWi. These primers, 12K FWD BglII and 12K REV BsiWI (Table 1), were used to amplify LV from the pTopo-LV miniprep plasmid DNA. The PCR product was digested with BglII and BsiWI and isolated by agarose gel electrophoresis and gel purification. This fragment, containing either B5R or H3L specific antibody LV, was ligated to the prepared 9.1 kb vector with T4 DNA ligase and used to transform Top10 cells (Invitrogen). Positive *E. coli* transformants were selected. The resulting expression vectors were purified, and the presence of both LV and HV regions confirmed by restriction analysis and DNA sequencing.

Generation of vectors to produce recombinant 131C14, 131C18, 130D67 and 130D53 antibodies was performed in the manner described above, the 3' primers used for amplification of the heavy and light chain genes in the RACE reactions were HH-2 and HK-2, respectively.

Amplification of the heavy chains for 131C14, 131C18, 130D25, 130D67 and 130D53 was performed using the respective primers listed in Table 1. The 131C14, 131C18, 130D25, 130D67 and 130D53 light chain variable region amplification was also performed using the respective primers listed in Table 1. The resulting vectors, pKLG1/131C14, pKLG1/131C18, pKLG1/130D25, and pKLG1/130D67 were confirmed by restriction enzyme digestion and sequencing.

TABLE 1

Synthesized DNA primers (SEQ ID NOS: 73-107)

| Seq Id No | Name | Sequence 5' to 3' | Length |
|---|---|---|---|
| 73 | B5R-Ftopo dir gate | CACCATGAAAACGATTTCCGTTGTTA | 26-mer |
| 74 | B5R-Rtopo dir gate | TTCTAACGATTCTATTTCTTGTTCATATTGTAC | 33-mer |
| 75 | H3L F NdeI pET-15b | AGAGAGAGACATATGGCGGCGGCGAAAACT | 30-mer |
| 76 | H3L R Bam HI pET-15b | CTCTCTCTCTGGATCCTTAGATAAATGCGGTAACGA | 37-mer |

TABLE 1 -continued

| Seq Id No | Name | Sequence 5' to 3' | Length |
|---|---|---|---|
| | | Synthesized DNA primers (SEQ ID NOS: 73-107) | |
| 77 | H3L fwd NheI pET28 | AGAGAGAGAGCTAGCGCGGCGGCGAAAACT | 30-mer |
| 78 | HK5 | AGGCACACAACAGAGGCAGTTCCAGATTTC | 30-mer |
| 79 | HH-2 | GCTGGAGGGCACGGTCACCACGCTG | 25-mer |
| 80 | HK-2 | GTTGAAGCTCTTTGTGACGGGCGAGC | 26-mer |
| 81 | M13F | GTAAAACGACGGCCAGTG | 18-mer |
| 82 | M13R | CAGGAAACAGCTATGAC | 17-mer |
| 83 | HK5 | AGGCACACAACAGAGGCAGTTCCAGATTTC | 30-mer |
| 84 | 12H FWD SalI | AGAGAGAGAGGTCGACCACCATGGAGTTTGGGCT GAGCTGG | 41-mer |
| 85 | 12H REV NheI | AGAGAGAGAGGCTAGCTGAGGAGACGGTGACCG TGGT | 37-mer |
| 86 | 12K FWD BglII | AGAGAGAGAGAGATCTCACAGCATGGACATGAG GGTCCCCGCT | 43-mer |
| 87 | 12K REV BsiwI | AGAGAGAGAGCGTACGTTTGATATCCACTTTGGT CCCAGG | 40-mer |
| 88 | 14H FWD SalI | AGAGAGAGAGGTCGACCACCATGGAACTGGGGC TCCGC | 38-mer |
| 89 | 14H REV NheI | AGAGAGAGAGGCTAGCTGAGGAGACGGTGACCG TGGT | 37-mer |
| 90 | 14K1 FWD BglII | AGAGAGAGAGAGATCTCACAGCATGGACATGAG GGTCCCCGCTC | 44-mer |
| 91 | 14K1 REV BsiWI | AGAGAGAGAGCGTACGTTTGATCTCCAGCTTGGT CCCCTG | 40-mer |
| 92 | 25H FWD SalI | AGAGAGAGAGGTCGACCACCATGGAGTTGGGAC TGAGC | 38-mer |
| 93 | 25H REV NheI | AGAGAGAGAGGCTAGCTGAGGAGACGGTGACCA G | 34-mer |
| 94 | 25K1 FWD BglII | AGAGAGAGAGAGATCTGGAACCATGGAAGCCCC AGCT | 37-mer |
| 95 | 25K1 REV BsiWI | AGAGAGAGAGCGTACGTTTGATCTCCACCTTGGT | 34-mer |
| 96 | 25K2 FWD BglII | AGAGAGAGAGAGATCTCACAGCATGGACATGAG GGTC | 37-mer |
| 97 | 25K2 REV BsiWI | AGAGAGAGAGCGTACGTTTGATATCCACTTTGGT | 34-mer |
| 98 | 25K3 FWD BglII | AGAGAGAGAGAGATCTCACAGCATGGACATGAG GGTC | 37-mer |
| 99 | 25K3 REV BsiWI | AGAGAGAGAGCGTACGTTTGATTTCCACCTTGGT | 34-mer |
| 100 | 67H FWD SAlI | AGAGAGAGAGGTCGACCACCATGGAGTTGGGAC TG | 35-mer |
| 101 | 67H REV NheI | AGAGAGAGAGGCTAGCTGAGGAGACGGTGACCA G | 34-mer |
| 102 | 67K1 FWD BglII | AGAGAGAGAGAGATCTCACAGCATGGACATGAG GGTC | 37-mer |
| 103 | 67K1 REV BsiWI | AGAGAGAGAGCGTACGTTTGATATCCACTTTGGT | 34-mer |
| 104 | 67K2 FWD BglII | AGAGAGAGAGAGATCTGGAACCATGGAAGCCCC AGCT | 37-mer |

TABLE 1 -continued

| Synthesized DNA primers (SEQ ID NOS: 73-107) | | | |
|---|---|---|---|
| Seq Id No | Name | Sequence 5' to 3' | Length |
| 105 | 67K2 REV BsiWI | AGAGAGAGAGCGTACGTTTGATCTCCACCTTGGT | 34-mer |
| 106 | 67K3 FWD BglII | AGAGAGAGAGAGATCTCACAGCATGGACATGAG GGTC | 37-mer |
| 107 | 67K3 REV BsiWI | AGAGAGAGAGCGTACGTTTGATTTCCACCTTGGT | 34-mer |

Production of recombinant human anti-B5R antibody from CHO Cells: For production of recombinant antibody, individual antibody vectors containing anti-B5R or H3L antibody were nucleofected into host cell dhfr-defective strain of Chinese Hamster Ovary cell (CHO cells, ATCC #CRL-9096) and recombinant antibody was isolated from the supernatant of the transfected cells. Briefly, 2 μg DNA of purified DNA expression vector was linearized by a DNA restriction enzyme, AscI, and the DNA was nucleofected into $1\times10^7$ cells CHO cells using the nucleofector kit V (Cat. No. VCA-1003) and the Amaxa nucleofector (Amaxa Biosystems) following manufacturer's instructions. The transfected cells were seeded in 96-well culture plates in EX-CELL 325 PF CHO serum-free medium with glutamine (JRH Bioscience, Lenexa, Kans.), supplemented with penicillin/streptomycin (BioWhitaker), HT (Sigma), and Geneticin (Invitrogen, Corp.) for selecting CHO cells containing the DNA vector. After the selection of several stable transfectant lines, high human IgG producers were identified by ELISA, and used for production of recombinant antibody.

Example 2

This example describes exemplary heavy and light chain variable region sequences of antibodies that bind to B5R.

Nucleotide sequence of cDNA of 131C12 heavy chain variable region (HV) (from initiation codon (ATG) to the end of variable region) is as follows (SEQ ID NO:1):

```
ATGGAGTTTG GGCTGAGCTG GCTTTTTCTT GTGGCTATTT TAAAAGGTGT CCAGTGTGAG  60
GTGCAGCTGT TGGAGGCCGG GGGAGGCTTG GTACAGCCTG GGGGGTCCCT GAGACTCTCC 120
TGTGCAGCCT CTGGATTCAC CTTTAGCAGC TCTGCCATGA GCTGGGTCCG CCAGGCTCCA 180
GGGAAGGGGC TGGAGTGGGT CTCAGTTATT AGTATTAGTG GTGGTAGCAC ATACTACGCA 240
GACTCCGTGA AGGGCCGGTT CACCATCTCC AGAGACAATT CCAAGAACAC GCTGAATCTG 300
CAAATGAACA GCCTGAGAGC CGAGGACACG GCCGTATATT ACTGTGCGAA AGAAACTCGG 360
TACTATTATT CCTACGGTAT GGACGTCTGG GGCCAAGGGA CCACGGTCAC CGTCTCCTCA 420
```

Nucleotide sequence of cDNA of 131C12 light chain variable region (LV) (from initiation codon (ATG) to the end of variable region) is as follows (SEQ ID NO:3):

```
ATGGACATGA GGGTCCCCGC TCAGCTCCTG GGGCTTCTGC TGCTCTGGCT CCCAGGTGCC  60
AGATGTGCCA TCCAGTTGAC CCAGTCTCCA TCCTCCCTGT CTGCATCTGT AGGGGACAGA 120
GTCACCATCA CTTGCCGGGC AAGTCAGCGC ATTGGCTTTG CTTTAGCCTG GTATCAGCAG 180
AAACCAGGGA AAGCTCCTAA ACTCCTGATC CATGATGCCT CCAGTTTGGA AACTGGGGTC 240
CCATCAAGGT TCAGCGGCAG TGGATCTGGG ACAGATTTCA CTCTCGCCAT CAGCAGCCTG 300
CAGCCTGAAG ATTTTGCAAC TTATTACTGT CAACAGTTTA ATACTTACCC ATTCACTTTC 360
GGCCCTGGGA CCAAAGTGGA TATCAAA                                    420
```

Nucleotide sequence of cDNA of 131C14 heavy chain variable region (HV) (from initiation codon (ATG) to the end of variable region) is as follows (SEQ ID NO:5):

```
ATGGAACTGG GGCTCCGCTG GGTTTTCCTT GTTGCTATTT TAGAAGGTGT CCAGTGTGAG  60
GTGCAGCTGG TGGAGTCTGG GGGAGGCCTG GTCAAGCCTG GGGGGTCCCT GAGACTCTCC 120
TGTGCAGCCT CTGGATTCAC GTTCAGCAGC TATAGCATGA ACTGGGTCCG CCAGGCTCCA 180
```

-continued

```
GGGAAGGGAC TGGAGTGGGT CTCATCTATT AGTAGTAGTA GAAGTTTCAT ATACTACGCA 240

GACTCAGTGA AGGGCCGATT CACCATCTCC AGAGACATCG CCAAGAACTC ACTGTCTCTG 300

CAAATGAGCA GCCTGAGAGT CGAGGACACG GCTGTGTATT ACTGTGCGAG AGAAAGGAGG 360

TACTACTACT CCTACGGTCT GGACGTCTGG GGCCAAGGGA CCACGGTCAC CGTCTCCTCA 420
```

Nucleotide sequence of cDNA of 131C14 light chain variable region (LV) (from initiation codon (ATG) to the end of variable region) is as follows (SEQ ID NO:7):

```
ATGGACATGA GGGTCCCCGC TCAGCTCCTG GGGCTTCTGC TGCTCTGGCT CCCAGGTGCC  60

AGATGTGCCA TCCAGTTGAC CCAGTCTCCA TCCTCCCTGT CTGCATCTGT AGGAGACAGA 120

GTCACCATCA CTTGCCGGGC AAGTCAGGGC ATTAGCAGTG CCTTAGCCTG GTATCAGCAG 180

AAACCAGGGA AAGCTCCTAA GCTCCTGATC TATGATGCCT CCAGTTTGGA AAGTGGGGTC 240

CCATCAAGGT TCAGCGGCAG TGGATCTGGG ACAGATTTCA CTCTCACCAT CAGCAGCCTG 300

CAGCCTGAAG ATTTTGCAAC TTATTACTGT CAACAGTTTA ATAGTTACCC GTACACTTTT 360

GGCCAGGGGA CCAAGCTGGA GATCAAA                                    420
```

Nucleotide sequence of cDNA of C18 kappa light chain variable region (LV) (from initiation codon (ATG) to the end of variable region) is as follows (SEQ ID NO:9):

```
ATGGACATGA GGGTCCCCGC TCAGCTCCTG GGGCTTCTGC TGCTCTGGCT CCCAGGTGCC  60
AGATGTGCCA TCCAGTTGAC CCAGTCTCCA TCCTCCCTGT CTGCATCTGT AGGGGACAGA 120
GTCACCATCA CTTGCCGGGC AAGTCAGCGC ATTGGCTTTG CTTTAGCCTG GTATCAGCAG 180
AAACCAGGGA AAGCTCCTAA ACTCCTGATC CATGATGCCT CCAGTTTGGA AACTGGGGTC 240
CCATCAAGGT TCAGCGGCAG TGGATCTGGG ACAGATTTCA CTCTCGCCAT CAGCAGCCTG 300
CAGCCTGAAG ATTTTGCAAC TTATTACTGT CAACAGTTTA ATACTTACCC ATTCACTTTC 360
GGCCCTGGGA CCAAAGTGGA TATCAAA                                    420
```

Nucleotide sequence of cDNA of C18 heavy chain variable region (HV) (from initiation codon (ATG) to the end of variable region) is as follows (SEQ ID NO:11):

```
ATGGAACTGG GGCTCCGCTG GGTTTTCCTT GTTGCTATTT TAGAAGGTGT CCAGTGTGAG  60

GTGCAGCTGG TGGAGTCTGG GGGAGGCCTG GTCAAGTCTG GGGGGTCCCT GAGACTCTCC 120

TGTGCAGCCT CTGGATTCAC CCTCAGTAGC TATAGCATGA ACTGGGTCCG CCAGGCTCCA 180

GGGAAGGGGC TGGAGTGGGT CTCATCCATT AGTAGTAGTA GTAGTTACAT ATACTACGCA 240

GACTCAGTGA AGGGCCGATT CACCATCTCC AGAGACATCG CCAAGAACTC ACTGTCTCTG 300

CAAATGAGCA GCCTGAGAGC CGAGGACACG GCTGTGTATT ACTGTGCGAG AGAAAGGAGG 360

TACTACTACT CCTACGGTAT GGACGTCTGG GGCCAAGGGA CCACGGTCAC CGTCTCCTCA 420
```

Amino acid sequence of cDNA of 131C12 heavy chain variable region (HV) (leader sequence (bold) and variable region) is as follows (SEQ ID NO:2):

```
MEFGLSWLFL VAILKGVQCE VQLLEAGGGL VQPGGSLRLS CAASGFTFSS SAMSWVRQAP 60
GKGLEWVSVI SISGGSTYYA DSVKGRFTIS RDNSKNTLNL QMNSLRAEDT AVYYCAKETR 120
YYYSYGMDVW GQGTTVTVSS                                           180
```

Amino acid sequence of cDNA of 131C12 light chain variable region (LV) (leader sequence (bold) and variable region) is as follows (SEQ ID NO:4):

```
MDMRVPAQLL GLLLLWLPGA RCAIQLTQSP SSLSASVGDR VTITCRASQR IGFALAWYQQ 60
KPGKAPKLLI HDASSLETGV PSRFSGSGSG TDFTLAISSL QPEDFATYYC QQFNTYPFTF 120
GPGTKVDIK                                                       180
```

Amino acid sequence of cDNA of 131C14 heavy chain variable region (HV) (leader sequence (bold) and variable region) is as follows (SEQ ID NO:6):

```
MELGLRWVFL VAILEGVQCE VQLVESGGGL VKPGGSLRLS CAASGFTFSS YSMNWVRQAP 60
GKGLEWVSSI SSSRSFIYYA DSVKGRFTIS RDIAKNSLSL QMSSLRVEDT AVYYCARERR 120
YYYSYGLDVW GQGTTVTVSS                                           180
```

Amino acid sequence of cDNA of 131C14 light chain variable region-A (LV) (leader sequence (bold) and variable region) is as follows (SEQ ID NO:8):

```
MDMRVPAQLL GLLLLWLPGA RCAIQLTQSP SSLSASVGDR VTITCRASQG ISSALAWYQQ 60
KPGKAPKLLI YDASSLESGV PSRFSGSGSG TDFTLTISSL QPEDFATYYC QQFNSYPYTF 120
GQGTKLEIK                                                       180
```

Amino acid sequence of C18 kappa light chain variable region (LV) (leader sequence (bold) and variable region) is as follows (SEQ ID NO:10):

```
MDMRVPAQLL GLLLLWLPGARCAIQLTQSP SSLSASVGDR VTITCRASQR      60
IGFALAWYQQ KPGKAPKLLI HDASSLETGV PSRFSGSGSG TDFTLAISSL    120
QPEDFATYYC QQFNTYPFTF GPGTKVDIK                           180
```

Amino acid sequence of C18 heavy chain variable region (HV) (leader sequence (bold) and variable region) is as follows (SEQ ID NO:12):

```
MELGLRWVFLVAILEGVQCE VQLVESGGGL VKSGGSLRLS CAASGFTLSS      60
YSMNWVRQAP GKGLEWVSSI SSSSSYIYYA DSVKGRFTIS RDIAKNSLSL    120
QMSSLRAEDT AVYYCARERR YYYSYGMDVW GQGTTVTVSS               180
```

Example 3

This example describes exemplary heavy and light chain variable region sequences of antibodies that bind to H3L.

Analysis of 130D25, 130D67 and 130D53 heavy and light chains revealed that they had the same heavy and light chain sequences. Hence, only the heavy and light chain variable region sequences of 130D67 are shown.

Nucleotide sequence of cDNA of 130D67 heavy chain variable region (HV) (from initiation codon (ATG) to the end of variable region) is as follows (SEQ ID NO:13):

```
ATGGAGTTGG GACTGAGCTG GATTTTCCTT TTGGCTATTT TAAAAGGTGT CCAGTGTGAA      60
GTGCAGCTGG TGGAGTCTGG GGGAGGCTTG GTACAGCCTG GCAGGTCCCT GAGACTCTCC     120
TGTGCAGCCT CTGGATTCAC CTTTGATGAT TATGCCATTC ACTGGGTCCG GCAAGCTCCA     180
GGGAAGGGCC TGGAGTGGGT CTCAGGTATT AGTTGGAATG GTCGTAGCAT AGGCTATGCG     240
GACTCTGTGA AGGGCCGATT CACCATCTCC AGAGACAACG CCAAGAACTC CCTGTATCTG     300
CAAATGAACA GTCTGAGAGC TGAGGACACG GCCTTGTATT ACTGTGCAAA GGATATAGGC     360
TTCTATGGTT CGGGGAGCCT TGACTACTGG GGCCAGGGAA CCCTGGTCAC CGTCTCCTCA     420
```

Nucleotide sequence of cDNA of 130D67K-Light chain variable region (LV) (from initiation codon is as follows (SEQ ID NO:15):

```
ATGGAAGCCC CAGCTCAGCT TCTCTTCCTC CTGCTACTCT GGCTCCCAGA TACCACCGGA      60
GAAATTGTGT TGACACAGTC TCCAGCCACC CTGTCTTTGT CTCCAGGGGA AAGAGCCACC     120
CTCTCCTGCA GGGCCAGTCA GAGTGTTAGC AGCTACTTAG CCTGGTACCA ACAGAAACCT     180
GGCCAGGCTC CCAGGCTCCT CATCTATGAT GCATCCAACA GGGCCACTGG CATCCCAGCC     240
AGGTTCAGTG GCAGTGGGTC TGGGACAGAC TTCACTCTCA CCATCAGCAG CCTAGAGCCT     300
GAAGATTTTG CAGTTTATTA CTGTCAGCAG CGTAGCAACT GGCCTGCGCT CACTTTCGGC     360
GGAGGGACCA AGGTGGAGAT CAAA                                            420
```

Amino acid sequence of cDNA of 130D67 heavy chain variable region (HV) (leader sequence (bold) and variable region) is as follows (SEQ ID NO:14):

MELGLSWIFL LAILKGVQCE VQLVESGGGL VQPGRSLRLS CAASGFTFDD YAIHWVRQAP 60

GKGLEWVSGI SWNGRSIGYA DSVKGRFTIS RDNAKNSLYL QMNSLRAEDT ALYYCAKDIG 120

FYGSGSLDYW GQGTLVTVSS 140

Amino acid sequence of cDNA of 130D67 light chain variable region (LV) (leader sequence (bold) and variable region) is as follows (SEQ ID NO:16):

MEAPAQLLFL LLLWLPDTTG EIVLTQSPAT LSLSPGERAT LSCRASQSVS SYLAWYQQKP 61

GQAPRLLIYD ASNRATGIPA RFSGSGSGTD FTLTISSLEP EDFAVYYCQQ RSNWPALTFG 121

GGTKVEIK

Example 4

This example includes a description of CDRs for exemplary B5R and H3L antibodies. This example also includes ATCC deposit numbers for exemplary B5R and H3L antibodies.

Exemplary CDR sequences (CDR1, CDR2 and CDR3) for variable region heavy (VH) and variable region light (VL) of exemplary B5R and H3L antibodies are set forth in Table 2 below:

TABLE 2

(SEQ ID NOs: 17-40):

| Antibody name | VH CDR1 | VH CDR2 | VH CDR3 | VL CDR1 | VL CDR2 | VL CDR3 |
|---|---|---|---|---|---|---|
| C12 | SSAMS (SEQ ID NO: 17) | VISISGGSTYYADSVKG (SEQ ID NO: 18) | ETRYYYSYGMDV (SEQ ID NO: 19) | RASQRIGFALA (SEQ ID NO: 29) | DASSLET (SEQ ID NO: 30) | QQFNTYPFT (SEQ ID NO: 31) |

TABLE 2-continued (SEQ ID NOs: 17-40):

| Antibody name | VH CDR1 | VH CDR2 | VH CDR3 | VL CDR1 | VL CDR2 | VL CDR3 |
|---|---|---|---|---|---|---|
| C14 | SYSMN (SEQ ID NO: 20) | SISSSRSFIYYADSVKG (SEQ ID NO: 21) | ERRYYYSYGLDV (SEQ ID NO: 22) | RASQGISSALA (SEQ ID NO: 32) | DASSLES (SEQ ID NO: 33) | QQFNSYPYT (SEQ ID NO: 34) |
| C18 | SYSMN (SEQ ID NO: 23) | SISSSSSYIYYADSVKG (SEQ ID NO: 24) | ERRYYYSYGMDV (SEQ ID NO: 25) | RASQRIGFALA (SEQ ID NO: 29) | DASSLET (SEQ ID NO: 30) | QQFNTYPFT (SEQ ID NO: 31) |
| D67 | DYAIH (SEQ ID NO: 26) | GISWNGRSIGYADSVKG (SEQ ID NO: 27) | DIGFYGSGSLDY (SEQ ID NO: 28) | RASQSVSSYLA (SEQ ID NO: 38) | DASNRAT (SEQ ID NO: 39) | QQRSNWPALT (SEQ ID NO: 40) |

The CDR sequences of light and heavy chain in Table 2 were identified using the NCBI Ig BLAST tool (CDR1 and CDR2 for both heavy and light chain) using the Kabat rules, and the position of CDR3 (CDR-L3 and -H3) was determined by applying the following rules:

The Cys residues are the most conserved feature.

For CDR-L1, start approximately at residue 24, Residue before a Cys, Residue after a Trp. Typically, for example, Trp-Tyr-Gln, but also, Trp-Leu-Gln, Trp-Phe-Gln, Trp-Tyr-Leu. Length 10 to 17 residues. For CDR-L2, start 16 residues after the end of L1, residues before generally Ile-Tyr, but also, Val-Tyr, Ile-Lys, or Ile-Phe. Length typically 7 residues (except NEW (7FAB) which has a deletion in this region). For CDR-L3, start 33 residues after end of L2 (except NEW (7FAB) which has the deletion at the end of CDR-L2), residue before a Cys, residues after Phe-Gly-XXX-Gly (SEQ ID NO:123). Length 7 to 11 residues. For CDR-H1, start approximately at residue 26 (4 after a Cys) [Chothia/AbM definition], Kabat definition starts 5 residues later. Residues before Cys-XXX-XXX-XXX (SEQ ID NO:124), residues after a Trp. Typically Trp-Val, but also, Trp-Ile, Trp-Ala. Length 10 to 12 residues [AbM definition], Chothia definition excludes the last 4 residues.

For CDR-H2, start 15 residues after the end of Kabat/AbM definition of CDR-H1, residues before typically Leu-Glu-Trp-Ile-Gly (SEQ ID NO:108), but there are variations, residues after Lys/Arg-Leu/Ile/Val/Phe/Thr/Ala-Thr/Ser/Ile/Ala. Length Kabat definition 16 to 19 residues; AbM (and recent Chothia) definition ends 7 residues earlier.

For CDR-H3, start 33 residues after end of CDR-H2 (2 after a Cys), residues before Cys-XXX-XXX (typically Cys-Ala-Arg), and residues after Trp-Gly-XXX-Gly (SEQ ID NO:109). Length 3 to 25 residues.

ATCC deposit numbers for exemplary B5R and H3L antibodies are set forth in Table 3 below:

TABLE 3

| Identification Reference by Depositor: | | ATCC ® Patent Deposit Designation: |
|---|---|---|
| Hybridoma Cell Line | 131C14 | PTA-8654 |
| | 131C18 | PTA-8562 |
| | 131C12 | PTA-8653 |
| | 130D67 | PTA-8564 |

Example 5

This example describes functional and molecular studies to characterize H3L and B5R antibodies. The panel of 12 human anti-H3 mAbs was characterized in vitro by assays to identify anti-H3 mAb for further examination and development. One functional test was virus neutralization in vitro. Molecular characterizations also assess relatedness of the clones, isotypes and affinities.

Supernatants from uncloned anti-H3 hybridoma cultures were pre-screened for neutralization activity. After cloning, anti-H3 mAbs of known concentration were screened in a conventional in vitro neutralization assay (Davies et al., *J Virol* 79:11724 (2005), Crotty et al., *J Immunol* 171:4969 (2003), Newman et al., *J Clin Microbiol* 41:3154 (2003), Frey et al., *N Engl J Med* 346:1275 (2002)). Neutralization potency of each mAb was determined by quantitative dose titrations, measuring the lowest mAb concentration able to inhibit VACV infection 50%, as measured by plaque assay ($PRNT_{50}$). The mAbs were analyzed in a series of three independent studies. Human mAbs were compared against several controls. Serum from an unvaccinated human was used as a negative control. Serum from a vaccinated human was used as a positive control. Mouse anti-H3 mAbs have also been isolated, and the best of those mAbs #41 was used as an additional comparison.

The results of analysis of anti-H3 mAbs are shown in FIG. 1. Seven out of 9 clones analyzed exhibited VACV virus neutralization activity. Six of these clones had strong virus neutralization activity (#25, #53, #58, deposited on Apr. 6, 2010, and has a deposit designation of PTA-10767 (ATCC 10801 University Blvd., Manassas, Va. 20110-2209), #62, #67, #137) (FIG. 1). In this assay, the best human mAb was #67, with a neutralization activity of 0.06 μg/ml, which was better than the best mouse mAb isolated in a pilot study (#41, $PRNT_{50}$=0.3 μg/ml, tested in parallel).

Anti-H3 mAbs were or will be subjected to molecular characterization. First, all anti-H3 mAbs were isotyped for both heavy chain and light chain, and all clones are human IgG1 κ. Second, estimates of relative affinities are determined by endpoint dilution ELISA using recombinant H3 as the capture antigen. Anti-H3 mAbs with higher affinities will generally report better endpoint dilution titers. Third, IEF gels will determine if all nine anti-H3 mAbs are independent clones, as indicated by distinct isoelectric points. Fourth, cross-blocking studies will determine if there are different epitopes on H3 recognized by the panel of 12 mAbs, and which mAbs are specific for the same (or overlapping) epitopes. Mouse mAbs will also be used in the cross-blocking studies to obtain more complete complementation groups.

Candidates for in vivo studies are determined by identifying the clones with potent in vitro neutralization activity. Clones with non-overlapping epitopes (i.e. clones 1, 2, and 3 for in vivo testing not all being specific to one epitope) are analyzed as different epitopes may have different levels of exposure in vivo. Finally, since all H3L clones thus far are human IgG1, and human IgG1 is a complement-fixing isotype, selection based on isotype at this point is unnecessary.

The panel of 11 B5R mAbs were characterized in vitro by assays to identify the best anti-B5 mAbs for further examination and development. One functional assay was direct neutralization in vitro. A second was a complement dependent neutralization assay (described in Example 8).

Vaccinia EEV neutralization is desired for an anti-B5 mAb to be used as a human immunotherapeutic. However, neutralization of EEV is less well defined than neutralization of IMV. EEV particles are highly labile and therefore it is difficult to produce EEV stocks (Smith et al., *J Gen Virol* 83:2915 (2002), Amanna et al., *Immunol Rev* 211:320 (2006), Isaacs et al., *J Virol* 66:7217 (1992), Lustig et al., *Virology* 328:30 (2004)). Furthermore, direct neutralization of EEV is very inefficient, with ~50% neutralization as a common best case scenario (Aldaz-Carroll et al., *J Virol* 79:6260 (2005)). One assay that resolves some of these problem is the comet tail inhibition assay (Amanna et al., *Immunol Rev* 211:320 (2006), Galmiche et al., *Virology* 254:71 (1999)).

Some poxvirus strains, particularly if left for a longer time (e.g. 72 hrs) will form "comet tail" plaques. The comet tails are due to the release of EEV virions from infected cells, and the EEV particles diffuse a short distance before infecting new cells. The directionality of the comet tail is due to weak convection currents in the medium. Comet tail formation can be inhibited by addition of anti-B5 antibodies to medium (Lustig et al., *J Virol* 79:13454 (2005), Bell et al., *Virology* 325:425 (2004), Lustig et al., *Virology* 328:30 (2004), Viner et al., *Microbes Infect* 7:579 (2005)).

The full panel of human anti-B5 mAbs were analyzed by comet tail inhibition. $VACV_{IHDJ}$ was used in the assay as it produces a higher percentage of EEV than $VACV_{NYBOH}$ and thereby more distinct comet tails. $VACV_{IHDJ}$ is used by other research groups studying EEV for this reason.

Figure 2:
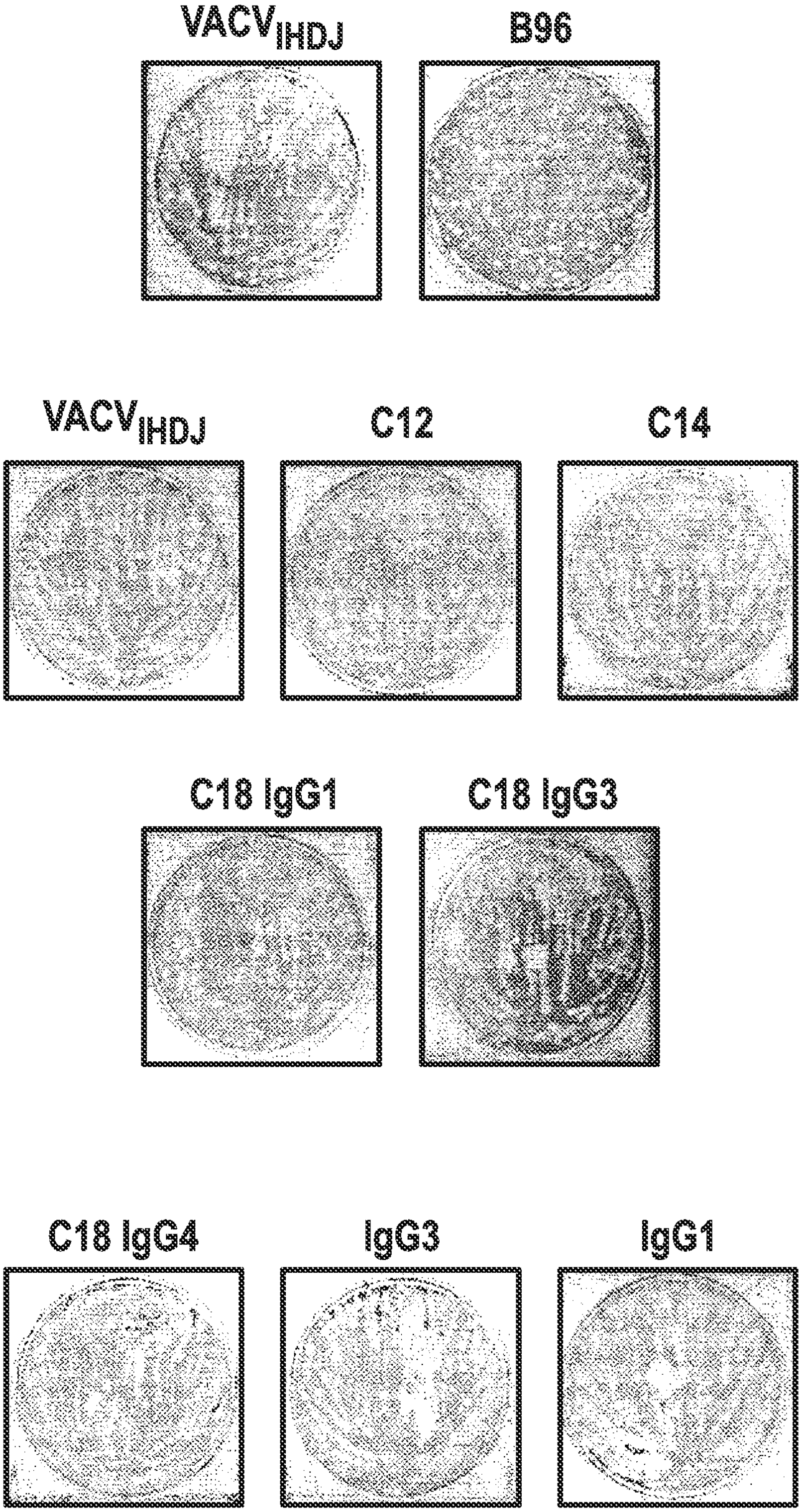
FIG. 2 shows data of $VACV_{IHDJ}$ comet tail plaque assay in the presence of no serum ($VACV_{IHDJ}$), isotype control antibodies (IgG3 and IgG1), and a panel of anti-B5 monoclonal antibodies (B96, C12, C14, C18 IgG1, C18 IgG3, C18 IgG4). B96 was a very efficient inhibitor of comet tail formation. C12 provided some inhibition, and C14 provided minimal inhibition. C18 IgG1 provided some inhibition, but the IgG3 and IgG4 versions did not inhibit comet tails.

Hela cells were infected at low density (40 PFU in a 6 well dish) and then overlaid with medium containing 20 μg/ml anti-B5 mAb. Serum from a vaccinated donor with the highest anti-B5 titer was used as a positive control (at a 1:10 dilution), and serum samples from several unvaccinated donors were used as negative controls (also at 1:10 dilution). Cells were incubated for 72 hrs without disturbance and then developed with crystal violet fixation to observe comet tails. Positive control serum from a vaccinated donor with the highest anti-B5 IgG titer gave nearly complete inhibition of comet tail formation (FIG. 2A). Serum from unvaccinated donors did not prevent comet tail formation. Isotype control IgG1 or IgG3 mAbs did not prevent comet tail formation (FIG. 2). Several anti-B5 mAbs partially inhibited comet tail formation (e.g. 131C12 and B96), while others had no detectable effect on comet tail formation (e.g. 131C18-G3 or 131C18-G4) (FIG. 2).

While the comet tail in vitro assay can measure functional anti-EEV neutralization, this assay has two limitations. First, comet tails can be inhibited by anti-EEV B5-specific antibodies, but the inhibition requires a high concentration of antibody −20-40 μg/ml is frequently used. This is ~500× more IgG than the amount of anti-H3 mAb needed to neutralize IMV. It is also much higher than the IgG concentrations required to neutralize a wide variety of viruses in vitro, such as influenza, SARS, polio, and rabies. Such high levels of anti-B5 IgG may not be physiological. Second, anti-EEV antibodies targeting the A33 protein are protective in vivo but do not inhibit comet tail formation, indicating a distinction between in vitro EEV comet tail inhibition and in vivo EEV neutralization (Lustig et al., *J Virol* 79:13454 (2005), Galmiche et al., *Virology* 254:71 (1999)). Given these limitations, the power of the comet tail assay to predict which anti-B5 mAbs would be most efficacious in vivo is limited. Thus, the complement dependent neutralization assay described in Example 8 can be used as a primary endpoint. B5R mAbs were also subjected to the molecular characterizations described above for H3 mAbs. The 11 human anti-B5 mAbs were isotyped for both heavy chain and light chain (All κ). Six of 11 were IgG1, three were IgG4, one was IgG3, and one was IgG2. Second, estimates of relative affinity of the purified clones are determined by endpoint dilution ELISA using recombinant B5 as the capture antigen in a standard BIAcore assay using purified mAbs. MAbs with higher affinities will generally report better endpoint dilution titers. Third, IEF gels were run to determine if all six of the most promising mAbs are independent clones, as indicated by distinct isoelectric points.

Cross-blocking studies were performed to determine the number of different epitopes on B5 recognized by a panel of mAbs, and which mAbs are specific for the same (or overlapping) epitopes. An ELISA was used to determine if the antibodies bind to the same B5R epitope.

In brief, NUNC 96 well flat bottom ELISA plates were coated with individual mouse or human anti-B5R antibodies in carbonate buffer at 2 μg/ml for 1 hour at 37° C. The plates were washed and then blocked with PBS/1% BSA/Tween 20. Anti-B5R antibodies were then pre-incubated with recombinant vaccinia virus 6×His tagged soluble B5R for 30 minutes at 4° C. The combinations of antibody-protein were added to the plate and incubated for 1 hour at 4° C. After 3 washes, bound B5R-6×His was detected with peroxidase conjugated anti-6×His epitope tag Ig (Clonetech). C12 and C14 are human anti-B5R antibodies and B96, B116 and B126 are mouse anti-B5R antibodies. The percent inhibition was determined using the OD of each sample in the following formula: % inhibition=(max−sample/max)*100. Max represents the OD from the sample with no inhibiting Ab or hIgG isotype control. The cross-blocking results are illustrated in Tables 4A and 4B:

TABLE 4A

| | Plate coated Ab | | | | | |
|---|---|---|---|---|---|---|
| Soluble Ab | C12 | C14 | C18 | B96 | B116 | B126 |
| C12 | 92 | 92 | 95 | 0 | 0 | 5 |
| C14 | 85 | 92 | 92 | 0 | 0 | 4 |
| C18 | 63 | 84 | 83 | 0 | 0 | 17 |
| B96 | 0 | 0 | 26 | 93 | 0 | 17 |
| B116 | 0 | 0 | 0 | 0 | 91 | 10 |
| B126 | 0 | 0 | 20 | 0 | 0 | 96 |
| Hum IgG1 | 0 | 0 | 0 | 0 | 0 | 0 |

TABLE 4B

| Soluble | Plate coated Ab | | | | |
|---|---|---|---|---|---|
| Ab | C12 | C14 | C18 | C33 | C30 |
| C12 | 65 | 94 | 88 | 92 | 82 |
| C14 | 61 | 93 | 0 | 92 | 78 |
| C18 | 0 | 0 | 95 | 0 | 0 |

TABLE 4B-continued

| Soluble | Plate coated Ab | | | | |
|---|---|---|---|---|---|
| Ab | C12 | C14 | C18 | C33 | C30 |
| C33 | 57 | 92 | 12 | 89 | 79 |
| C30 | 65 | 93 | 68 | 92 | 81 |
| no Ab | 0 | 0 | 0 | 0 | 0 |

The data show that C12, C14, C18, C33 and C30 block each other and are therefore members of the same epitope group. B116, B126 and B96 are not blocked, and therefore each represent distinct epitope groups. In toto, there are five epitope groups (Groups A-D) recognized by the anti-B5R antibodies based on competition for binding to recombinant B5R protein (B5R-6×His) by ELISA. Top B5R antibody candidates bind to the overlapping epitope groups: C12 and C14 seem to recognize the same or very closely related epitope, and C18 seem to recognize an epitope cluster overlapping with but not identical to that of C12 and C14.

Example 6

This example describes in vivo efficacy studies of B5R and H3L antibodies, using three standard lethal challenge vaccinia models.

There are three in vivo models used to study the ability of mAb pretreatment to protect mice. The first is intranasal challenge of BALBc with $VACV_{WR}$. The second is intravenous challenge of SCID mice with $VACV_{WR}$ vaccine strain. The third is intravenous challenge of SCID mice with $VACV_{NYBOH}$ vaccine strain. Studies with these models are described in detail below.

All 10 anti-B5 mAbs were analyzed for the ability to protect BALBc mice from a lethal intranasal challenge with $VACV_{WR}$. This is the same assay used in the studies described in Example 4 and is widely used as a model for smallpox inhalation in humans (Ramirez et al., *J Gen Virol* 83:1059 (2002), Zhang et al., *J Virol* 74:11654 (2000), Belyakov et al., *Proc Natl Acad Sci USA* 100:9458 (2003), Alcami et al., *Cell* 71:153 (1992)). In this regard, the respiratory route of infection of $VACV_{WR}$ and smallpox are the same. An excellent feature of this model is that while the primary endpoint is survival, weight loss can also be tracked as a quantitative measure of protection. Both severity (nadir) and duration of weight loss can be used as criteria to measure the severity of the infection in instances of partial protection. In brief, each mouse was administered 100 μg of a particular anti-B5 mAb i.p. at day −1 (5 mice/group). After light anesthesia (isofluorane), mice were infected intranasally with $3\times10^4$ PFU $VACV_{WR}$ (2 $LD_{50}$) in a 10 μl volume. Mouse weight was measured daily for a period of four weeks. Any mouse with 30% weight loss was euthanized as per the animal protocol, based on earlier work showing mice do not recover from that severe weight loss. Mice were also examined for clinical symptoms (lethargy, ruffled fur, hunched back) that can be composited into a mean clinical disease score (similar to Crotty et al., Blood 108:3085 (2006)). The human mAbs were compared to a murine mAb #B96.

Figure 3C:
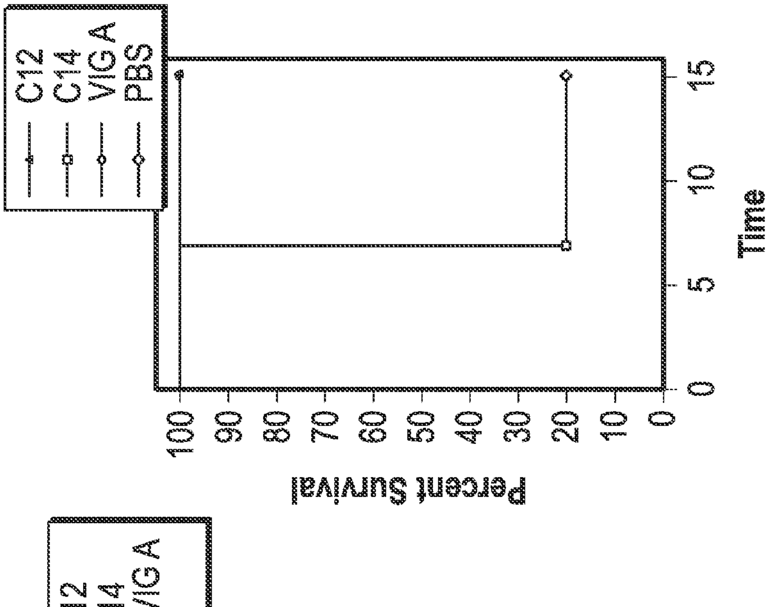
FIGS. 3A-3C show protection of BALBc mice from lethal intranasal $VACV_{WR}$ infection data. A) and B) Average weight of mice after infection. A) Murine mAb #B96 versus two candidate human mAbs, #C14 and #C33 (100 μg each), i.p., PBS as negative control; B) Human mAbs #C14 and #C12 versus VIG (vaccinia immune globulin); and C) Survival curve from panel B study.
Figure 3B:
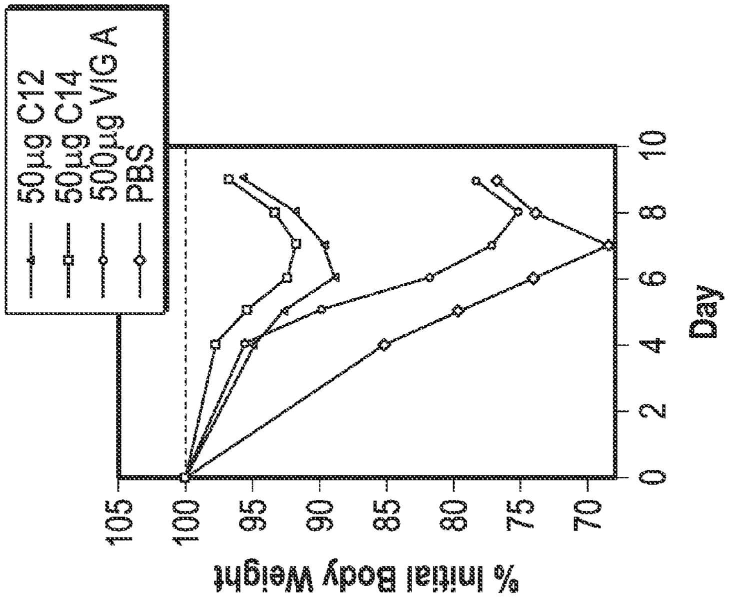
Figure 3A:
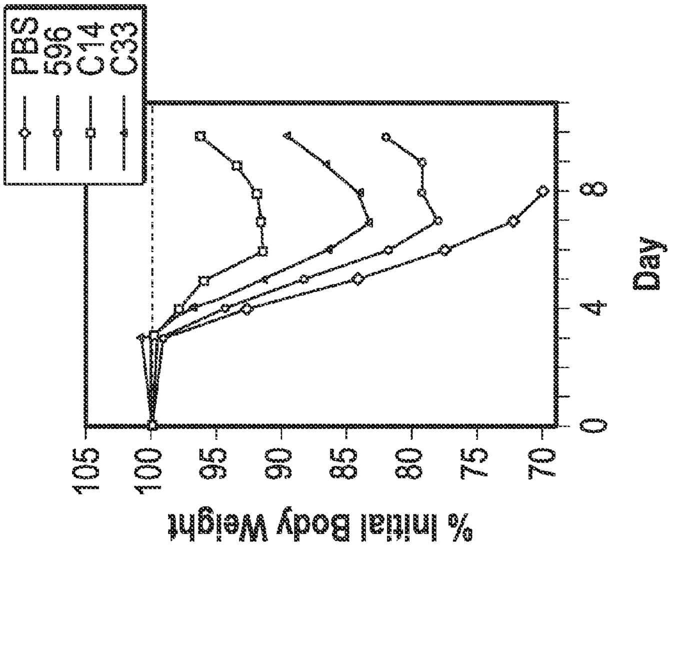

In a first study, human anti-B5 mAbs #C14 and #C33 provided 100% protection from death and provided better protection against weight loss than the mouse mAb #B96 (FIG. 3A). Plasma from an unvaccinated person was used as a negative control and had no protective effect. A study of the full panel of human anti-B5 mAbs was then performed. Eight of 10 human anti-B5 provided at least partial protection against mouse death (B5 antibodies, C12, C14, C30, C33, C18, C35, C29, C39).

In a subsequent study, the best candidate human mAbs, based on weight loss amelioration, were compared side-by-side in the $VACV_{WR}$ i.n. challenge model with VIG used as the benchmark treatment. The specific VIG used for this study was the reference Baxter VIG currently used by the FDA and CDC as their benchmark standard (Goldsmith et al., *Vox Sang* 86:125 (2004), Manischewitz et al., *J Infect Dis* 188:440 (2003)). Four of five untreated (PBS) mice lost weight rapidly and died or were euthanized by day 7 (FIG. 3B). VIG barely protected the mice from death (the 70% weight cutoff was almost reached for 3 of the 4 VIG-treated mice). In contrast, two human anti-B5 mAbs, namely C12 and C14, given as 50 μg doses, provided complete protection against death and both mAbs ameliorated weight loss substantially better than VIG (FIG. 3B-3C). These results indicate that both human mAbs are superior to VIG, even as a single mAb therapy. These results also demonstrate that high quality mAb, of comparable protective efficacy, virus, neutralization, B5R binding affinity, etc., can be readily obtained from KM mice using the protocol described herein.

The ability of particular B5 antibodies to protect in vivo was not predicted by the in vitro comet tail inhibition assay, highlighted most clearly by comparisons against B96, the best comet tail inhibiting mAb, which had poor protection in vivo. These results confirmed that the comet tail assay, although providing valuable information, is somewhat limited in predicting in vivo efficacy. In contrast, the complement dependent neutralization assay described herein was highly predictive of protective efficacy, both for mouse and human mAbsantibodies (Table 5). A summary of the isotype, binding, neutralization and in vivo protective activity of several anti-B5R antibodies is illustrated in Table 5. C12, C14 and C18 are human anti-B5R antibodies.

Using similar conditions, the protective efficacy of several human anti-B5 mAbs were studied in SCID mice infected with $VACV_{WR}$, a more virulent VACV strain than $VACV_{NYBOH}$. The data is shown in FIG. 4.

Figure 4A:
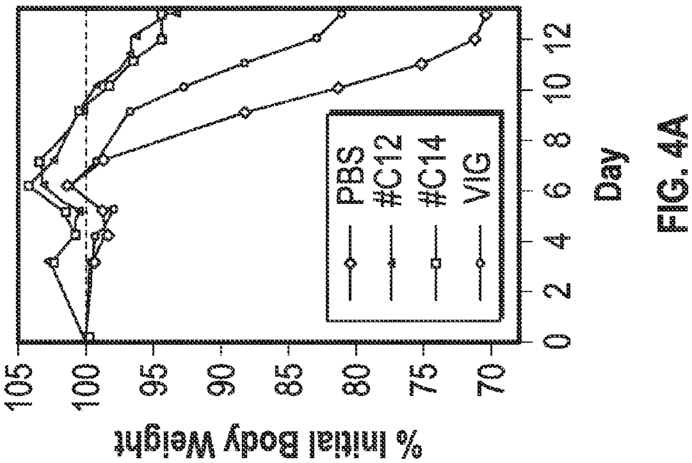
FIGS. 4A and 4B show protection of SCID mice from $VACV_{WR}$ data. A) Mice administered VIG, anti-B5 human mAb #C12, anti-B5 human mAb #C14, or PBS, then infected with $VACV_{WR}$; and B) Mice administered VIG, anti-H3 mAb #41, or PBS, then infected with $VACV_{WR}$. (VIG and PBS control groups are the same in both panels. All data shown is from an individual study.)

In brief, groups of 5 SCID mice were administered VIG, 100 μg anti-B5 human mAb #C12, 100 μg anti-B5 human mAb #C14, or PBS at day −1, then infected i.v. with $1\times10^3$ PFU $VACV_{WR}$ on day 0. Mice pretreated with either human anti-B5 mAb (C12, C14) were well protected from $VACV_{WR}$. The anti-B5 mAb treated mice had minimal weight loss and were all alive at day 14, while untreated mice (PBS) rapidly lost weight and all died by day 14. The anti-B5 mAbs both protected significantly better than VIG (FIG. 4A). This is similar to protection observed in the intranasal model (FIG. 3).

TABLE 5

| Antibody | Isotype | Epitope group | in vivo protection | comet tail neutralization | EEV + complement neutralization |
|---|---|---|---|---|---|
| C12 | human IgG1 | A1 | +++ | + | +++ |
| C14 | human IgG1 | A1 | +++ | +/− | +++ |
| C18 | human IgG1 | A2 | +++ | +/− | +++ |
| B96 | mouse IgG1 | B | + | +++ | + |
| B116 | mouse IgG1 | C | + | +++ | + |

TABLE 5-continued

| Antibody | Isotype | Epitope group | in vivo protection | comet tail neutra-lization | EEV + complement neutralization |
|---|---|---|---|---|---|
| B126 | mouse IgG2a | D | +++ | ++ | +++ |

The full panel of anti-H3 human mAbs, which have been characterized for virus neutralization in vitro, are tested in vivo. The best three candidates based upon neutralization assays are #67, #25, and #53, with #78 and #58, deposited on Apr. 6, 2010, and has a deposit designation of PTA-10767 (ATCC University Blvd., Manassas, Va. 20110-2209), also being of similar potency. Antibody #54 is a suitable negative control mAb, since it exhibited no detectable neutralization in vitro. The $VACV_{WR}$ BALBc i.n. challenge system and the $VACV_{NYBOH}$ SCID i.v. challenge system are used as described above for anti-B5. Since anti-H3 antibodies are protective in vivo (Davies et al., *J Virol* 79:11724 (2005)), rabbit anti-H3 serum is used as a positive control.

Figure 4B:
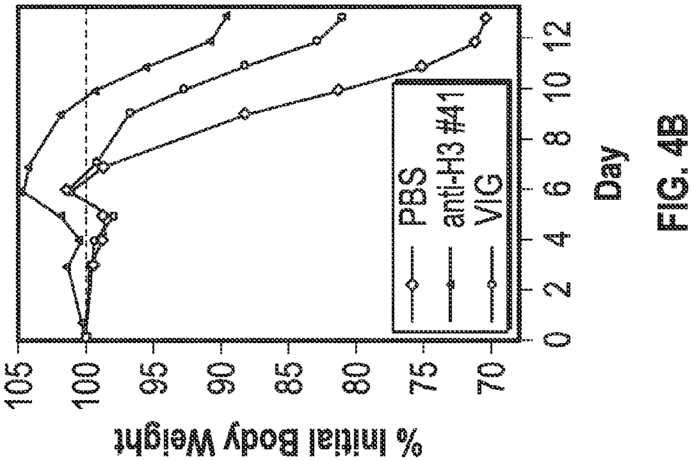

An in vivo protection study with mouse anti-H3 mAb #41 was performed. In brief, SCID mice were administered VIG, 200 μg anti-H3 #41 or PBS at day −1, then infected i.v. with $1\times10^3$ PFU $VACV_{WR}$ on day 0. The mice administered anti-H3 #41 exhibited substantial protection from weight loss for greater than two weeks after infection with virulent $VACV_{WR}$ (FIG. 4B). This data indicates that single mAb treatment with either anti-B5 or anti-H3 can outperform VIG in an in vivo SCID protection model similar to the one used for licensure of VIG. Since three human anti-H3 mAbs (#67, #25, and #53) have been identified that neutralize better than or equal to #41, it was expected that these antibodies will exhibit in vivo protection. This is demonstrated in Example 10. Combination anti-H3L and anti-B5R antibody therapy is therefore predicted to be very potent. This is also demonstrated below.

Combination anti-H3L and anti-B5R antibody therapy is therefore predicted to be very potent, which is also demonstrated below.

The third in vivo assay used as a screen for candidate mAbs is the animal model considered to resemble closely human progressive vaccinia. In this system, SCID mice are infected with smallpox vaccine $VACV_{NYBOH}$ and then measured for weight loss, pox formation, and death. This model has been used by VIG vendors (Shearer et al., *Antimicrob Agents Chemother* 49:2634 (2005)) and the FDA (Goldsmith et al., *Vox Sang* 86:125 (2004)). This model is valuable both because it uses the human vaccine strain of vaccinia and immunodeficient or immunocompromised humans are a group of concern for failing to control VACV and develop progressive vaccinia or other life threatening side effects, which are the clinical conditions for which VIG is licensed.

In this model, treatment with a human mg/kg equivalent dose of VIG is able to extend life by >1 week (Shearer et al., *Antimicrob Agents Chemother* 49:2634 (2005)), (Goldsmith et al., *Vox Sang* 86:125 (2004)). Since SCID mice are fully immunodeficient, a complete cure is not expected, but life extension correlates with the ability of VIG to reduce or prevent severe vaccinia side effects in humans, and an effective post-exposure prophylactic against smallpox. Since this assay uses the human smallpox vaccine strain, models vaccinia infection in an immunodeficient/immunocompromised setting, and has been used at the FDA, this animal model is useful for identifying successful candidate mAbs.

Figure 5:
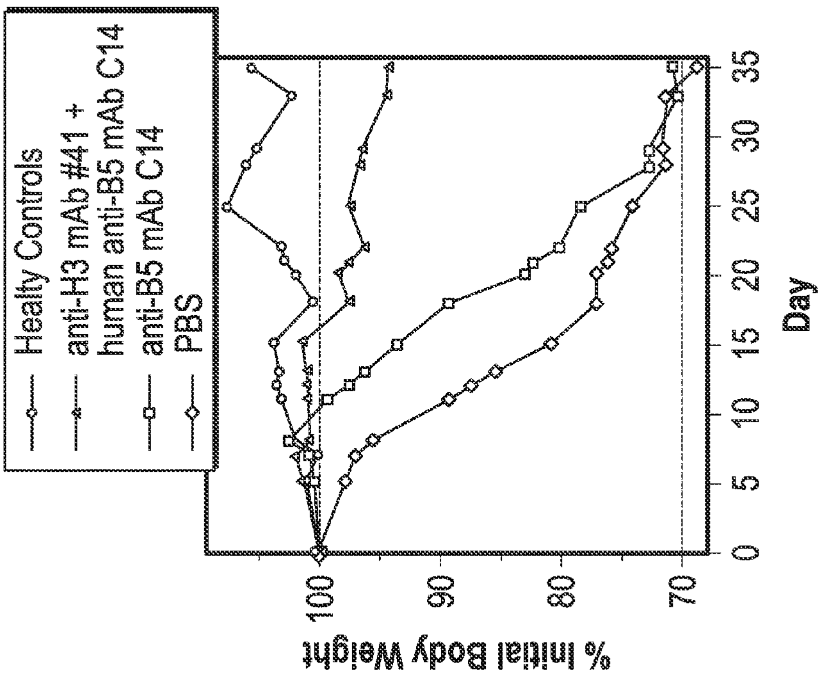
FIG. 5 shows data indicating that combination mAb therapy protects against $VACV_{NYBOH}$ in SCID mice better than monotherapy. SCID mice administered anti-H3 mAb #41+human anti-B5 mAb C14 (triangle symbols), anti-B5 mAb C14 alone (filled square symbols), or PBS (filled circles). Untreated, uninfected "naive" mice were used as controls (open circles).

In brief, groups of six SCID mice were administered anti-H3 mAb #41+human anti-B5 mAb C14 (200 μg and 100 μg respectively) (FIG. 5, triangle symbols), or anti-B5 mAb C14 alone (100 μg) (FIG. 5, filled square symbols), or PBS (FIG. 5, filled circles) i.p. at day −1. Mice were then infected with $1\times10^4$ PFU $VACV_{NYBOH}$ i.v. Untreated, uninfected "naive" mice were used as healthy controls (FIG. 5, open circles). As illustrated in FIG. 5, anti-H3+anti-B5 mAb combination far outperformed anti-B5 mAb monotherapy ($P<0.0007$).

Figure 6A:
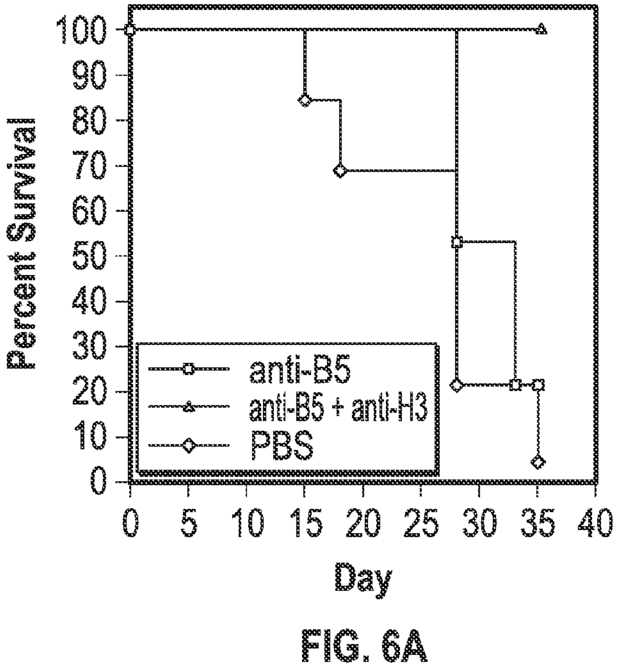
FIGS. 6A-6C show data indicating that combination mAb therapy protects against $VACV_{NYBOH}$ better than mAb monotherapy by multiple parameters of disease progression. SCID mice administered anti-H3 mAb #41 and human anti-B5 mAb C14 (filled triangle symbols), anti-B5 mAb C14 alone (filled square symbols), or PBS (filled circles). Control untreated, uninfected "naive" mice (open circles). A) Survival curve; B) percent of mice remaining pox free; and C) percent of mice remaining disease free (less than 5% body weight loss).
Figure 6B:
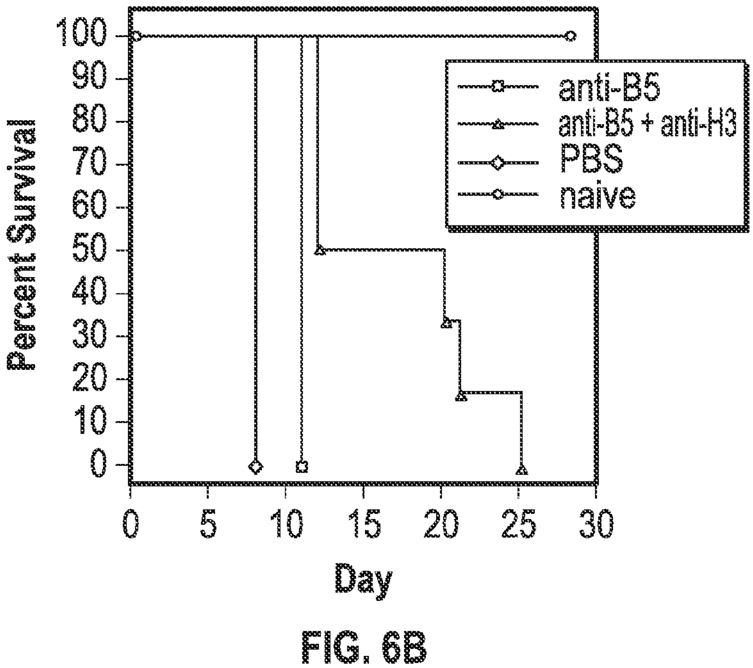
Figure 6C:
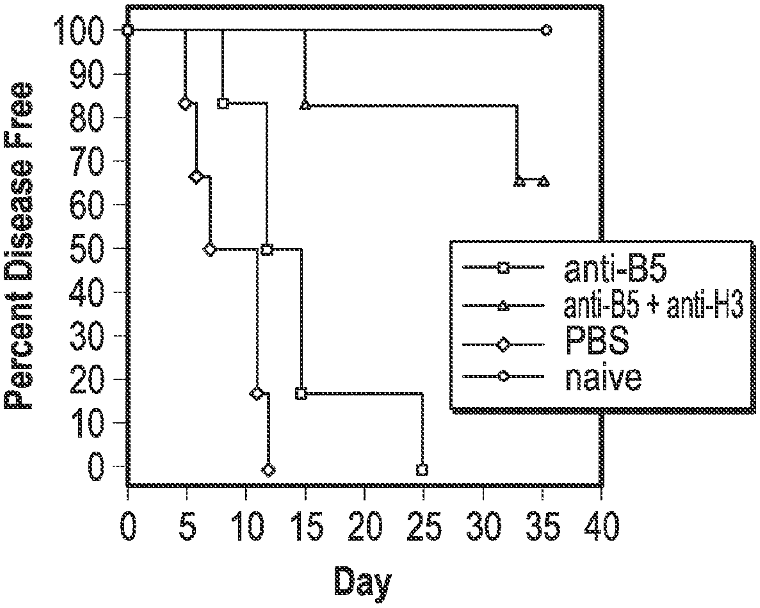

These mice were also scored for percent survival, development of pox lesions and those mice that remained disease free (FIG. 6). Untreated, uninfected "naive" mice were used as healthy controls (FIG. 6, open circles). Combination mAb therapy (FIG. 6A, filled triangle symbols) was significantly better than monotherapy (FIG. 6A, Filled square symbols) ($P<0.0047$) and no therapy (PBS, FIG. 6A, filled circles) ($P<0.0007$) in terms of survival. Mice were examined for the development of pox lesions daily, and the percent of mice that remained pox free is shown in FIG. 6B. Combination mAb therapy was significantly better than monotherapy ($P<0.0009$), and monotherapy or combination therapy was significantly better than no therapy ($P<0.0009$). The percent of mice that remained disease free, defined on the basis of weight loss is shown in FIG. 6C. The start of observable disease was defined as >5% weight loss. Combination mAb therapy was significantly better than monotherapy ($P<0.003$) and monotherapy or combination therapy were both significantly better than no therapy ($P<0.0006$ and $P<0.016$).

Work by other groups has shown that after initiation of infection, VIG can have a modest partial effect given post-exposure at day +2 to +4 (Shearer et al., *Antimicrob Agents Chemother* 49:2634 (2005)). Given the data with the more virulent $VACV_{WR}$ strain, human mAbs will likely outperform VIG.

The mAbs were compared to the commercially available "standard of care" VIG therapy. Mabs are considered "non-inferior" to VIG if they extend survival time by an equivalent number of days, and mAbs are considered "superior" to VIG if they extend survival time longer than VIG, as measured by standard Kaplan-Meier survival curve statistical analysis.

Figure 7:
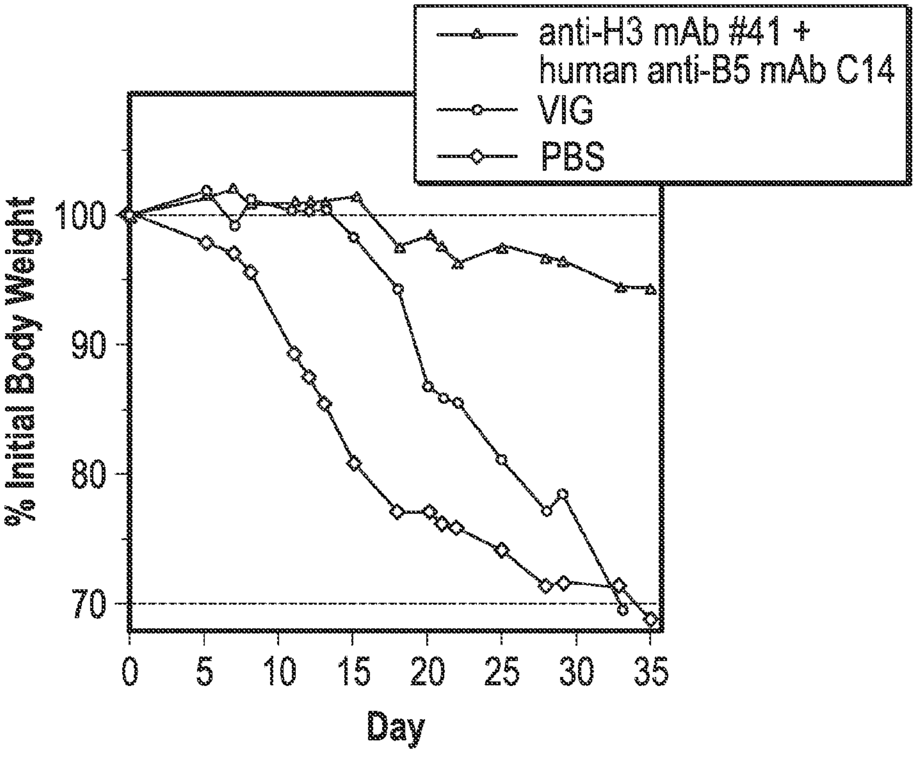
FIG. 7 shows data indicating that combination mAb therapy protects against $VACV_{NYBOH}$ in SCID mice better than commercially available therapy, VIG. SCID mice administered anti-H3 mAb #41 and human anti-B5 mAb C14 (triangle symbols), VIG (filled square symbols), or PBS (filled circles).

In brief, groups of six SCID mice were given anti-H3 mAb #41 (200 μg)+human anti-B5 mAb C14 (100 μg) (FIG. 7, triangle symbols), or VIG (2 mg) (FIG. 7, filled square symbols), or PBS (FIG. 7, filled circles) at day −1. Mice were then infected with $1\times10^4$ PFU $VACV_{NYBOH}$ i.v. As shown in FIG. 7, anti-H3+anti-B5 mAb combination outperformed VIG ($P<0.004$).

Figure 8A:
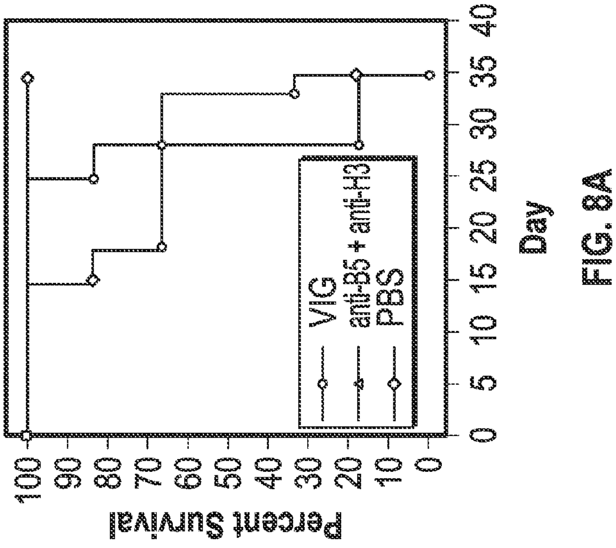
FIGS. 8A-8C show data indicating that combination mAb therapy protects against $VACV_{NYBOH}$ in SCID mice better than VIG by multiple parameters of disease progression. SCID mice administered anti-H3 mAb #41 and human anti-B5 mAb C14 (triangle symbols), VIG (Filled square symbols), or PBS (filled circles). A) Survival curve; B) percent of mice remaining pox free; and C) percent of mice remaining disease free (less than 5% body weight loss).
Figure 8B:
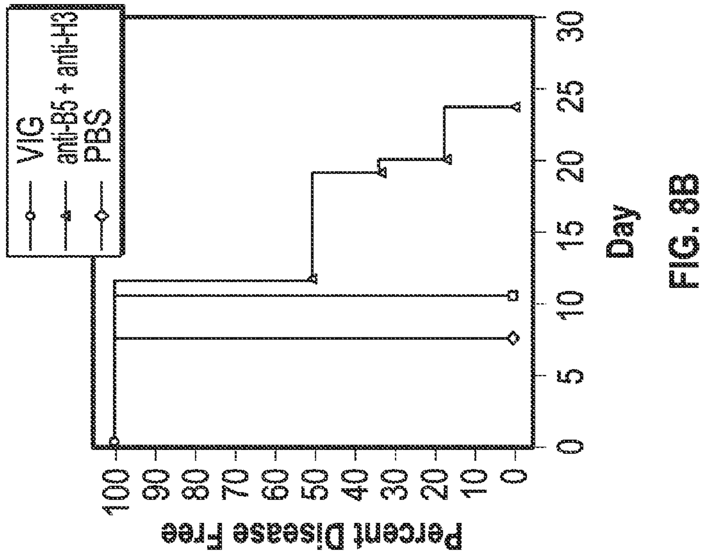
Figure 8C:
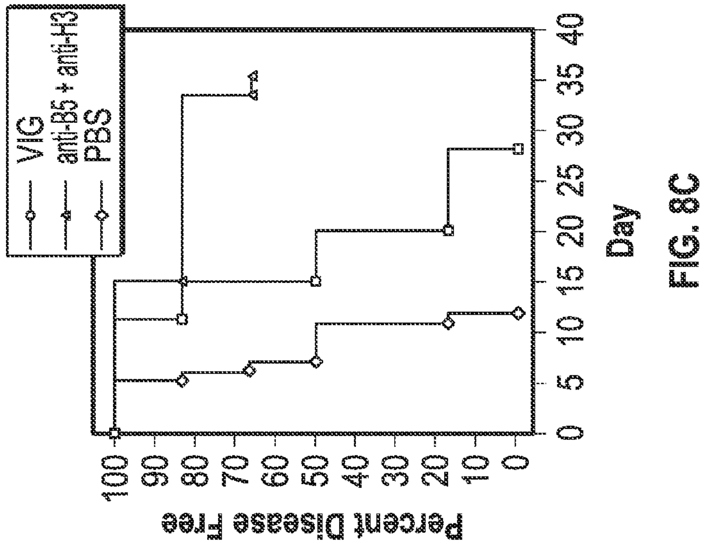

These mice were also scored for percent survival, development of pox lesions and for those that remained disease free (FIG. 8). As shown in FIG. 8, anti-H3+anti-B5 mAb combination therapy was significantly better than VIG therapy in terms of survival (FIG. 8A, $P<0.0045$), the percent of mice remaining pox free (FIG. 8B, $P<0.0009$), and the percent of mice remaining disease free (FIG. 8C, $P<0.0062$).

WorkReports by others groups has have shown that after initiation of infection, VIG can have a modest partial effect given post-exposure at day +2 to +4 (Shearer et al., Antimicrob Agents Chemother 49:2634 (2005)). Given the data with the more virulent VACVWR strain, human mAbsantibodies will likely outperform VIG.

Example 7

This example includes a description of additional assays useful in characterizing function and broad reactivity spectrum of antibodies.

Demonstration of immunological cross-reactivity of top antibodies with variola Virus homologs: H3 protein is highly conserved among orthopox viruses. The H3 protein sequence is 96-98% conserved between VACV and variola (smallpox), and 94% conserved between VACV and monkeypox. B5 has similarly high levels of conservation, close to 92%. For some mAbs, Western blot analysis can be used to check their cross-reactivity in vitro.

Bacterially expressed recombinant full-length B6 protein and its fragments: 825 nucleotides of the predicted nucleotide sequence coding for amino acids 1-275 of the variola virus protein B6 (accession #X65519) were synthesized by GenScript Corporation (Piscataway, N.J., USA). Five vectors for the expression of various lengths of the B6 protein were produced using bacterial expression vector pMAL-C4X (New England BioLabs, Ipswich, Mass., USA). The pMAL-C4X vector contains the malE gene for expression of maltose-binding protein (MBP). All of the vectors were constructed such that the nucleotides coding for the B6 protein were inserted downstream of, and in the same translational reading frame as, the malE gene. As a result, the translation initiating with the MBP protein should continue through the coding region of the B6 forming an MBP-B6 fusion protein. In general, the resulting fusion proteins consist of 391 amino acids at the amino-terminal end coding for the maltose-binding protein followed by the portion of B6 protein coded for by the region of B6 cloned into that particular expression vector. Constructs encoding B6 fragments were designed to contain overlapping short consensus repeat sequences (SCR) to facilitate narrowing down epitope specificity for top anti-B5 mAbs. The five expression vectors created are: 1) pMAL-B6R (B6 amino acids 20-275), 2) pMAL-B6R(SCR1-SCR2) (B6 amino acids 20-132), 3) pMAL-B6R(SCR2-SCR3) (B6 amino acids 71-184), 4) pMAL-B6R(SCR3-SCR4) (B6 amino acids 133-275), 5) pMAL-B6R (20-100) (B6 amino acids 20-100). All of the above vectors were constructed using the same technique. Briefly, oligonucleotide primers specific for the regions of interest were designed containing 5'-EcoRI and 3'-HinDIII restriction endonuclease recognition sites: B6 (20-275) (primers SCR1_EcoR1_F58, ExCell_HindIII_R828), B6 (20-132) (primers SCR1_EcoR1_F58, SCR2_HindIII_R396), B6 (71-184) (primers SCR2_EcoR1_F211, SCR3_HindIII_R552), B6 (133-275) (primers SCR3_EcoR1_F397, ExCell_HindIII_R828), B6 (20-100) (primers SCR1_EcoR1_F58, B6R_HindIII_R300). (Table 6) Respective oligonucleotide primers were used to amplify B6 gene fragments from the B6 template by polymerase chain reaction (PCR) with KOD Hot Start DNA polymerase (EMD Chemicals, Inc., Gibbstown, N.J., USA). The resulting nucleotide fragments were digested with restriction enzymes EcoRI and HinDIII (New England BioLabs), as was the pMAL-C4X vector. All nucleotide fragments were run on agarose gels, and DNA bands corresponding to the theoretical nucleotide size were extracted and purified by column purification (QIAquick Gel Extraction Kit, Qiagen Inc., Valencia, Calif., USA). Each of the B6 nucleotide fragments were separately ligated into the pMAL-C4X vector using DNA Ligase Mighty Mix (Takara Bio USA, Madison, Wis., USA). Ligation mix was transformed into *E. coli* bacteria strain DH5a (Invitrogen Corp., Carlsbad, Calif., USA) and grown on Luria-Bertani (LB) broth (MP Biomedicals, LLC, Solon, Ohio, USA) agarose plates containing ampicillin (100 ug/mL) (Sigma-Aldrich, St. Lois, Mo., USA). Colonies were grown in LB broth with ampicillin, plasmid DNA was isolated (QIAprep Spin Miniprep Kit, Qiagen, Inc.), analyzed by restriction digest and sequenced to verify nucleotide sequence of the B6 fragments (GENEWIZ, Inc., San Diego, Calif., USA).

TABLE 6

(SEQ ID NOs: 110-116)

| Number | Name | Sequence 5'-3' | Length |
|---|---|---|---|
| 1 (110) | SCR1_1_EcoR1_F58 | ACGTATCGAATTCACATGTACTGTACCCACTATGAATAACG | 41-mer |
| 2 (111) | ExCell_HindIII_R828 | TTACGATAAGCTTTCATTCTAACGATTCTATTTCTTGTT CATATTGTAC | 49-mer |
| 3 (112) | SCR2_HindIII_R396 | CTAGTACAAGCTTTCAAGATTGACATTCCGCATTAG | 36-mer |
| 4 (113) | SCR3_HindIII_R552 | ATAGCTAAGCTTTCATTGTTGACATGATGGAATAAC | 36-mer |
| 5 (114) | SCR2_EcoRI_F211 | ACGTACTGAATTCCCATGTAAAAAAATGTGTACAGTTTCTG | 41-mer |
| 6 (115) | SCR3_EcoR1_F397 | ATCGTACAGAATTCCTTCAATTAGATCACGGATCTTGTC | 39-mer |
| | | TTACGATAAGCTTTCAAATTAGTGTTATGATGGCATTT | 49-mer |
| 7 (116) | B6R_HindIII_R300 | ACTTCGTATAG | |

B6 Bacterial Expression:

B6 expression vectors were transformed into *E. coli* bacteria strain DH5a and grown on LB broth-agarose plates containing ampicillin (100 ug/mL). Individual colonies were grown over night (~18 hours) at 37° C. shaking at 250 rpm in liquid LB containing ampicillin (100 ug/mL). Cultures were diluted 1 part in 20 into two containers of fresh LB with ampicillin and incubated as before. When cultures reached an optical density at a wavelength of 600 nm ($OD_{600}$) of 0.5-0.8, one of the duplicate cultures was induced to express the B6 protein by adding isopropyl β-D-1-thiogalactopyranoside (IPTG) (BioPioneer, Inc., San Diego, Calif., USA) to a final concentration of 1 mM; the other paired culture was not induced. The cultures were grown as before for three hours. Equal volumes of each culture were removed, bacteria pelleted by centrifugation, supernatant removed, and pellets were lysed by adding 2× Laemmli buffer (Laemmli UK, Nature 227, 680-685, 1970) and incubating at 95° C. for 5 minutes.

B6 Sequences

Nucleotide sequence of the extracellular domain of variola virus B6 cDNA (accession #X65519) from initiation codon (ATG) to the end of extracellular domain (nucleotides 1-825) SEQ ID NO:117

```
ATGAAAACGA TTTCCGTTGT TACGTTGTTA TGCGTACTAC CTGCGGTTGT TTATTCAACA   60
TGTACTGTAC CCACTATGAA TAACGCTAAA TTAACGTCTA CCGAAACATC GTTTAATGAT  120
AAACAAAAAG TTACATTTAC ATGTGATTCG GGATATTATT CTTTGGATCC AAATGCTGTC  180
TGTGAAACAG ATAAATGGAA ATACGAAAAT CCATGTAAAA AAATGTGTAC AGTTTCTGAT  240
TATGTCTCTG AACTATATAA TAAACCGCTA TACGAAGTAA ATGCCATCAT AACACTAATT  300
TGTAAAGACG AAACAAAATA TTTTCGTTGT GAAGAAAAAA ATGGAAATAC TTCTTGGAAT  360
GATACTGTTA CGTGTCCTAA TGCGGAATGT CAATCTCTTC AATTAGATCA CGGATCTTGT  420
CAACCAGTTA AAGAAAAATA CTCATTTGGG GAACATATAA CTATCAACTG TGATGTTGGA  480
TATGAGGTTA TTGGTGCTTC GTACATAACT TGTACAGCTA ATTCTTGGAA TGTTATTCCA  540
TCATGTCAAC AAAAATGTGA TATACCGTCT CTATCTAATG GATTAATTTC CGGATCTACA  600
TTTTCTATCG GTGGCGTTAT ACATCTTAGT TGTAAAAGTG GTTTTATACT AACGGGATCT  660
CCATCATCCA CATGTATCGA CGGTAAATGG AATCCCGTAC TCCCAATATG TATACGATCT  720
AACGAAGAAT TTGATCCAGT GGAGGATGGT CCCGATGATG AGACAGATTT AAGCAAACTC  780
TCAAAAGACG TTGTACAATA TGAACAAGAA ATAGAATCGT TAGAA                  840
```

Amino acid sequence of Variola major virus, strain India-1967, B6 extracellular domain (amino acids 1-275, leader sequence (bold)); SEQ ID NO:118

```
MKTISVVTLL CVLPAVVYST CTVPTMNNAK LTSTETSFND KQKVTFTCDS GYYSLDPNAV   60
CETDKWKYEN PCKKMCTVSD YVSELYNKPL YEVNAIITLI CKDETKYFRC EEKNGNTSWN  120
DTVTCPNAEC QSLQLDHGSC QPVKEKYSFG EHITINCDVG YEVIGASYIT CTANSWNVIP  180
SCQQKCDIPS LSNGLISGST FSIGGVIHLS CKSGFILTGS PSSTCIDGKW NPVLPICIRS  240
NEEFDPVEDG PDDETDLSKL SKDVVQYEQE IESLE                            300
```

Figure 9:
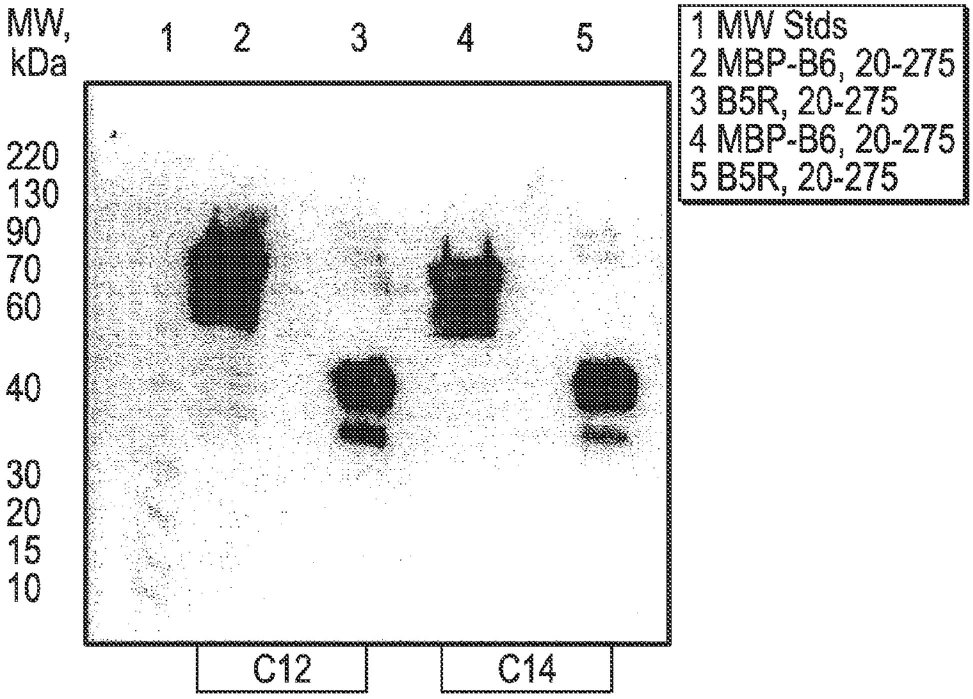
FIG. 9 shows results of a Western blot confirming cross-reactivity of anti-B5 top mAbs 131C12 and 131C14 with Variola B6 homolog. Similar results have been obtained with 131C18 mAb.

Demonstration of cross-reactivity of the lead anti-B5R mAbs with variola virus homolog by western blot: All top anti-B5R mAbs demonstrated their reactivity against B5R in Western blot conditions. Based on this result, Western blot assay could be used to check their cross-reactivity with variola homolog, B6. In this assay, adequate amounts of B6 ectodomain, its fragments, and B5R protein were blotted on PVDF membrane (0.45 um, Invitrogen) following electrophoresis on SDS PAGE (4-20% Tris-Glycine gels, Invitrogen). The blocked with milk membranes were incubated with 131C12, 131C14, or 131C18 human mAbs, and their binding was detected with goat anti-human IgG Fcγ HRP conjugate (Jackson Immunoresearch Labs). The antigen bands were visualized on X-ray film following exposure of the membranes pre-incubated with ECL Plus™ chemilimunescence substrate (GE Healthcare). Based on the western blot data, all top human anti-B5R mAbs demonstrated strong cross-reactivity with variola homolog protein, B6 (FIG. 9).

Figure 10:
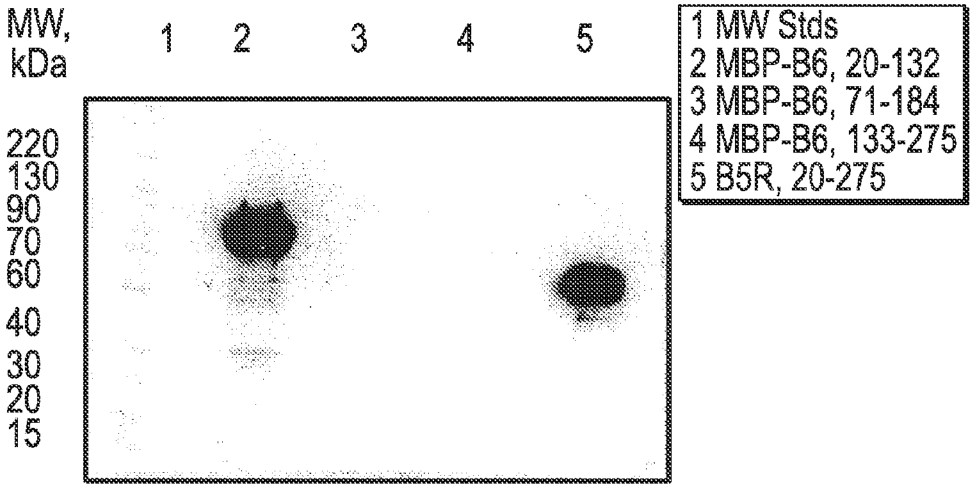
FIG. 10 shows results of a Western blot identifying SCR1 as an epitope cluster recognized by anti-B5 mAbs 131C12, 131C14 and 131C18. 131C12 mAb was used in the representative Western blot shown. Similar results were obtained with 131C14 and 131C18 mAbs.
Figure 11:
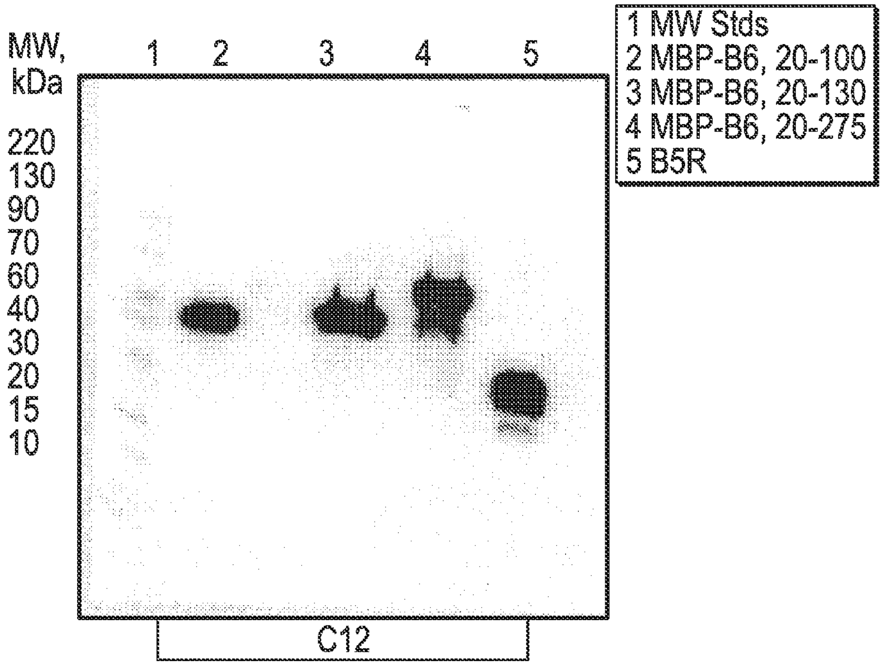
FIG. 11 shows results of a Western blot showing summary of anti-B5 mAbs (131C12, 131C14, and 131C18) reactivity. It confirmed that the antibodies recognized B6R peptide 20-100, including SCR1 and N-terminal portion of SCR2. 131C12 mAb was used in the representative Western blot shown. Similar results have been obtained with 131C14 and 131C18 mAbs.

Narrowing down epitope specificity for the top human anti-B5R mAbs by western blot: The epitope specificity of human anti-B5R mAbs was narrowed down to N-terminal portion of B5R protein, including SCR1, based upon the demonstrated reactivity towards fragments of B6 protein (FIGS. 10 and 11). The results are summarized in Table 7.

TABLE 7

| | Tested B6 Antigen | | | | |
|---|---|---|---|---|---|
| mAb | B6 ectodomain (aa 20-275) | SCR1 + N − SCR2 (aa20-100) | SCR1 + SCR2 (aa20-132) | SCR2 + SCR3 (aa71-184) | SCR3 + SCR4 (aa 133-275) |
| 131C12 | + | + | + | − | − |
| 131C14 | + | + | + | − | − |
| 131C18 | + | + | + | − | − |

Cloning of vaccinia and variola H3L ectodomains: Homologous nucleotide regions coding for amino-terminal extracellular domains of the H3 protein from variola virus strain Lister (VACVlis) (accession #AY678276), and variola major virus strain Bangladesh-1975 (VARVban) (accession #L22579) were separately cloned into bacterial expression vector pET21a(+) (EMD, Novagen Brand, Madison, Wis., USA) such that translation of the H3 coding frame would add a six histidine tag (6-HIS tag), coded for by nucleotides in the vector, at the carboxy-terminus of the H3 protein. Specifically, 807 nucleotides of the predicted nucleotide sequence coding for amino acids 1-269 of the H3 protein from VACVlis, and 810 nucleotide of the predicted nucleotide sequence coding for amino acids 1-270 of the H3 protein from VARVban were synthesized by GenScript Corporation (Piscataway, N.J., USA). Nucleotides coding for the restriction endonuclease sites of NdeI and XhoI were added at the 5' and 3' ends respectively of each H3 nucleotide fragment during synthesis. The nucleotide fragments were digested with restriction enzymes NdeI and XhoI, as was vector pET21a(+). Resulting H3 and pET21a(+) nucleotide fragments were isolated by agarose gel electrophoresis and purified using QIAquick Gel Extraction Kit (Qiagen Inc., Valencia, Calif., USA). Purified H3 nucleotide fragments were then ligated individually into the digested pET21a(+) vector, transformed into *E. coli* bacteria strain DH5a (Invitrogen Corp., Carlsbad, Calif., USA) and grown on Luria-Bertani (LB) broth (MP Biomedicals, LLC, Solon, Ohio, USA) agarose plates containing ampicillin (100 ug/mL) (Sigma-Aldrich, St. Lois, Mo., USA). Colonies were grown in LB broth with ampicillin, plasmid DNA was isolated (QIAprep Spin Miniprep Kit, Qiagen, Inc.), analyzed by restriction digest and sequenced to verify nucleotide sequence of the H3 fragments (GENEWIZ, Inc., San Diego, Calif., USA).

Protein Expression: Individually, H3 expression vectors were transformed into *E. coli* bacteria strain DH5αand grown on LB broth-agarose plates containing ampicillin (100 ug/mL). Individual colonies were grown over night (~18 hours) at 37° C. shaking at 250 rpm in liquid LB broth containing ampicillin (100 ug/mL). Cultures were diluted 1 part in 20 into two containers of fresh LB with ampicillin and incubated as before. When cultures reached an optical density at a wavelength of 600 nm ($OD_{600}$) of 0.5-0.8, one of the duplicate cultures was induced to express the H3 protein by adding isopropyl β-D-1-thiogalactopyranoside (IPTG) (BioPioneer, Inc., San Diego, Calif., USA) to a final concentration of 1 mM; the other paired culture was not induced. The cultures were grown as before for three hours. Equal volumes of each culture were removed, bacteria pelleted by centrifugation, supernatant removed, and pellets were lysed by adding 2× Laemmli buffer (Laemmli UK, Nature 227, 680-685, 1970) and incubating at 95° C. for 5 minutes.

H3L Ectodomains Nucleotide Sequences

Synthesized nucleotide sequence of H3 from vaccinia virus strain Lister (from NdeI restriction site (CATATG) through XhoI restriction site (CTCGAG). Start codon is ATG.) SEQ ID NO: 119

```
CATATGGCGG CGGTGAAAAC TCCTGTTATT GTTGTGCCAG TTATTGATAG ACCTCCATCA   60
GAAACATTTC CTAATGTTCA TGAGCATATT AATGATCAGA AGTTCGATGA TGTAAAGGAC  120
AACGAAGTTA TGCCAGAAAA AAGAAATGTT GTGGTAGTCA AGGATGATCC AGATCATTAC  180
AAGGATTATG CGTTTATACA GTGGACTGGA GGAAACATTA GAAATGATGA CAAGTATACT  240
CACTTCTTTT CAGGGTTTTG TAACACTATG TGTACAGAGG AAACGAAAAG AAATATCGCT  300
AGACATTTAG CCCTATGGGA TTCTAATTTT TTTACCGAGT TAGAAAATAA AAAGGTAGAA  360
TATGTAGTTA TTGTAGAAAA CGATAACGTT ATTGAGGATA TTACGTTTCT TCGTCCCGTC  420
TTGAAGGCAA TGCATGACAA AAAAATAGAT ATCCTACAGA TGAGAGAAAT TATTACAGGC  480
AATAAAGTTA AAACCGAGCT TGTAATGGAC AAAAATCATG CCATATTCAC ATATACAGGA  540
GGGTATGATG TTAGCTTATC AGCCTATATT ATTAGAGTTA CTACGGCGCT GAACATCGTA  600
GATGAAATTA TAAAGTCTGG AGGTCTATCA TCGGGATTTT ATTTTGAAAT AGCCAGAATC  660
GAAAACGAAA TGAAGATCAA TAGGCAGATA CTGGATAATG CCGCCAAATA TGTAGAACAC  720
GATCCTCGAC TTGTTGCAGA ATACCGTTTC GAAAACATGA AACCGAATTT TTGGTCTAGA  780
ATAGGAACGG CAGCTGCTAA ACGTTATCCA CTCGAG                             840
```

Synthesized nucleotide sequence of H3 from variola major virus strain Bangladesh-1975 (from NdeI restriction site (CATATG) through XhoI restriction site (CTCGAG). Start codon is ATG.) SEQ ID NO:120

```
CATATGGCGA CTGTGAATAA AACTCCTGTT ATTGTTGTGC CAGTTATTGA TAGACCTCCA   60
TCAGAAACAT TTCCTAATCT TCATGAGCAT ATTAATGATC AGAAGTTCGA TGATGTGAAG  120
GACAACGAAG TTATGCCAGA AAAAAGAAAT GTTGTGATAG TCAAGGATGA TCCAGATCAT  180
TACAAGGATT ATGCGTTTAT ACACTGGACT GGAGGAAACA TTAGAAATGA TGACAAGTAT  240
ACTCACTTCT TTTCAGGGTT TTGTAACACC ATGTGTACAG AGGAAACGAA AAGAAATATC  300
GCTAGACATT TAGCCCTATG GGATTCTAAA TTTTTTACCG AGTTAGAAAA TAAAAAGGTA  360
GAATATGTAG TTATTGTAGA AAATGATAAC GTTATTGAGG ATATTACGTT TCTTCGTCCA  420
```

-continued

```
GTCTTAAAGG CAATGCATGA CAAGAAAATA GATATCCTAC AGATGAGAGA AATTATTACA   480

GGCAATAAAG TTAAAACCGA GCTAGTAATG GACAAAAATC ATGTCATATT CACATATACA   540

GGAGGGTATG ATGTTAGCTT GTCAGCCTAT ATTATTAGAG TTACTACGGC GCTGAACATT   600

GTAGATGAAA TTATAAAGTC TGGAGGTCTA TCATCGGGAT TTTATTTTGA AATAGCCAGA   660

ATCGAAAACG AAATGAAGAT TAACAGGCAA ATAATGGATA ACTCTGCCAA ATACGTAGAA   720

CACGATCCTC GTCTTGTTGC AGAACACCGC TTTGAAAACA TGAAACCAAA TTTTTGGTCT   780

AGAATAGGAA CGGCAGCTGT TAAACGTTAT CCACTCGAG                          840
```

Amino acid sequence of H3 protein from vaccinia virus strain Lister expressed from vector pET21a(+) (amino acids 1-269 of H3 through the 6-HIS tag coded by the vector (underlined)) SEQ ID NO:121

```
MAAVKTPVIV VPVIDRPPSE TFPNVHEHIN DQKFDDVKDN EVMPEKRNVV VVKDDPDHYK    60

DYAFIQWTGG NIRNDDKYTH FFSGFCNTMC TEETKRNIAR HLALWDSNFF TELENKKVEY   120

VVIVENDNVI EDITFLRPVL KAMHDKKIDI LQMREIITGN KVKTELVMDK NHAIFTYTGG   180

YDVSLSAYII RVTTALNIVD EIIKSGGLSS GFYFEIARIE NEMKINRQIL DNAAKYVEHD   240

PRLVAEYRFE NMKPNFWSRI GTAAAKRYPL EHHHHHH                            300
```

Amino acid sequence of H3 protein from variola major virus strain Bangladesh-1975 expressed from vector pET21a (+) (amino acids 1-269 of H3 through the 6-HIS tag coded by the vector (underlined)) SEQ ID NO 122:

```
MATVNKTPVI VVPVIDRPPS ETFPNLHEHI NDQKFDDVKD NEVMPEKRNV VIVKDDPDHY    60

KDYAFIHWTG GNIRNDDKYT HFFSGFCNTM CTEETKRNIA RHLALWDSKF FTELENKKVE   120

YVVIVENDNV IEDITFLRPV LKAMHDKKID ILQMREIITG NKVKTELVMD KNHVIFTYTG   180

GYDVSLSAYI IRVTTALNIV DEIIKSGGLS SGFYFEIARI ENEMKINRQI MDNSAKYVEH   240

DPRLVAEHRF ENMKPNFWSR IGTAAVKRYP LEHHHHHH                           300
```

Figure 12A:
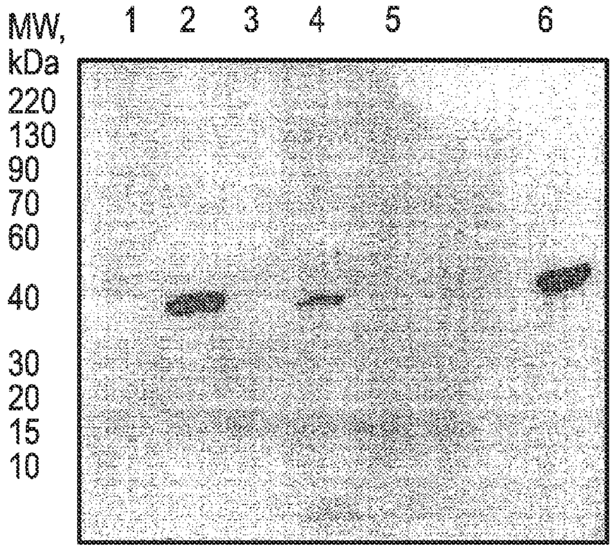
FIGS. 12A-12B show results of two Western blots confirming cross-reactivity of human anti-vaccinia H3 mAb 131D67 with variola homolog. Lanes 3 and 5: lysate of *E. coli* cells transformed with H3L ectodomain constructs from Variola and Vaccinia (respectively) before induction with IPTG. Lanes 2 and 4: lysate of *E. coli* cells expressing H3L ectodomain from Variola and Vaccinia (respectively) after induction with IPTG. Lane 6: Purified recombinant full-length H3L-His Tag®, 0.5 μg per lane. The membranes were probed with 130D67 antibody (A) and mouse monoclonal antibody specific to His Tag® (B).
Figure 12B:
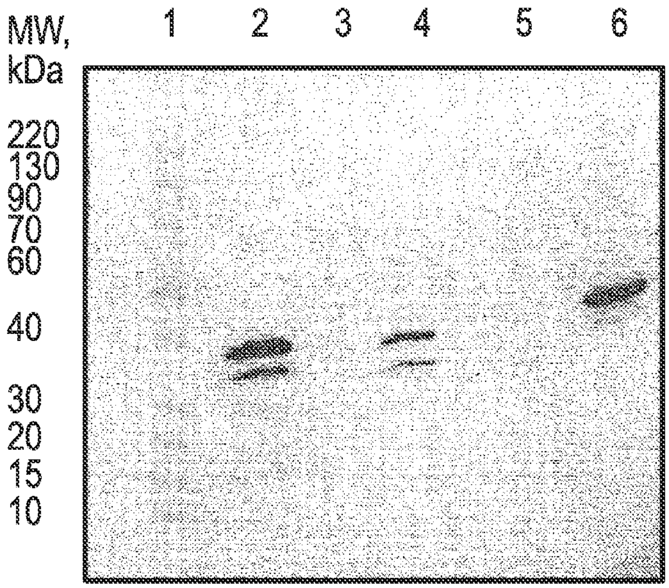

Demonstration of cross-reactivity of human anti-vaccinia H3L 130D67 mAb with variola virus homolog by western blot:

Western blot assay confirmed that 130D67 human mAb raised against vaccinia H3L cross-reacts with variola homolog. The antibody showed strong recognition of H3L ectodomain both from vaccinia and variola viruses (FIG. 12 A). Based on the lack of reactivity with the lower H3L band recognized by anti-His Tag® mAb, the epitope of 130D67 has been mapped to the 1-80 aa region of H3 (FIG. 12 A,B). This finding supports broad spectrum reactivity of the 130D67 antibody and its suitability to protect against variola smallpox virus.

Neutralization of Variola and Monkeypox: While VIG lots are not directly tested for efficacy against variola or monkeypox, mAbs can be assayed for neutralization of variola and/or monkeypox. Given that the best available data indicates that post-exposure treatment with VIG is ~75% effective against smallpox (Hopkins et al., *Clin Infect Dis* 39:819 (2004)), a national or military VIG stockpile would likely be dual purpose-treatment of smallpox vaccine side effects, and emergency treatment of a smallpox outbreak.

Ng/NDA $VACV_{WR}$ Eczema Vaccinatum Model: A mouse model for eczema vaccinatum has been established (Kawakami et al., *Alergol. Int.* Epub, 56, September (2007)) Given that eczema vaccinatum is a concern of the smallpox vaccine, the ability of mAb therapy to treat eczema vaccinatum is studied. Atopic dermatitis is induced in Ng/NDA mice, which are then infected with $VACV_{WR}$ at the site of the dermatitis. Eczema vaccinatum is measured by lesion size and clinical score. Mice are treated with anti-B5 mAb, anti-H3 mAb, or VIG intravenously immediately prior to $VACV_{WR}$ scarification. Protection is measured by reduction of eczema vaccinatum lesion size and lesion duration. In a separate set of studies, protection is measured by reduction of viral loads in the lesion (at the site of infection) at day 7, and prevention/reduction of viral spread as measured by viral titers in lung at day 7 post-infection. Skin biopsies can also be taken from this study at day 7, and pathology scoring of histological sections from each animal will be done to measure severity of epithelial damage and leukocyte infiltration.

SCID $VACV_{WR}$ tail pocks model: This is a model that has been used by investigators to query protection against pock/lesion formation after VACV infection. While the lesions are not histologically the same as human smallpox, monkeypox, or vaccinia infection, the model does recapitulate the basic phenomenon of distinct viral skin pustules. While this assay has been around for 40 years (Joshi et al., *Appl Microbiol* 18:935 (1969)), there can be large variability between individual mice, making it necessary to use large numbers of animals to determine statistically significant differences (Shearer et al., *Antimicrob Agents Chemother* 49:2634 (2005)). Groups of 12 BALBc mice are treated with mAbs or VIG at day −1 and then infected with $2\times10^5$ PFU $VACV_{NYBOH}$ at day 0 by subcutaneous injection of the tail. Necrotic pocks on the tail skin are visualized at day 8 by counterstaining (Shearer et al., *Antimicrob Agents*

*Chemother* 49:2634 (2005)), Joshi et al., *Appl Microbiol* 18:935 (1969)) and quantified. If $VACV_{NYBOH}$ vaccine strain fails to give sufficient pocks, a more virulent VACV strain ($VACV_{WR}$ or $VACV_{IHD-J}$) can be used, as has been done by other investigators (CangeneCorporation, (ed. WIPO) (2003), Neyts et al., *Antimicrob Agents Chemother* 46:2842 (2002), Spriggs et al., *Proc Natl Acad Sci USA* 89:6070 (1992)).

Example 8

This example includes a description of a new EEV neutralization assay that correlates with in vivo protection against vaccinia. This example also includes in vivo protection data and data generated with this EEV neutralization assay.

Conventional neutralization assays are done in the absence of complement (using heat inactivated serum) and are what can be called "direct neutralization" assays. While such assays provide useful information, it is likely that aspects of neutralization in vivo are heavily influenced by complement and mAbs are likely to vary in their virus neutralization in the presence of complement (see, for example, B5, described later). Thus, it is useful to assay virus neutralization in the presence of complement. Given that the EEV comet tail inhibition assay is limited in terms of predicting protective efficacy of anti-B5 mAbs in vivo (Table 5), and EEV are resistant to conventional direct neutralization, a new in vitro EEV neutralization assay that more accurately predicts or correlates with in vivo protection was developed. This assay can be used to develop data to provide greater in vivo relevancy for comparing functional antiviral characteristics of mAbs vs. VIG.

Figure 13:
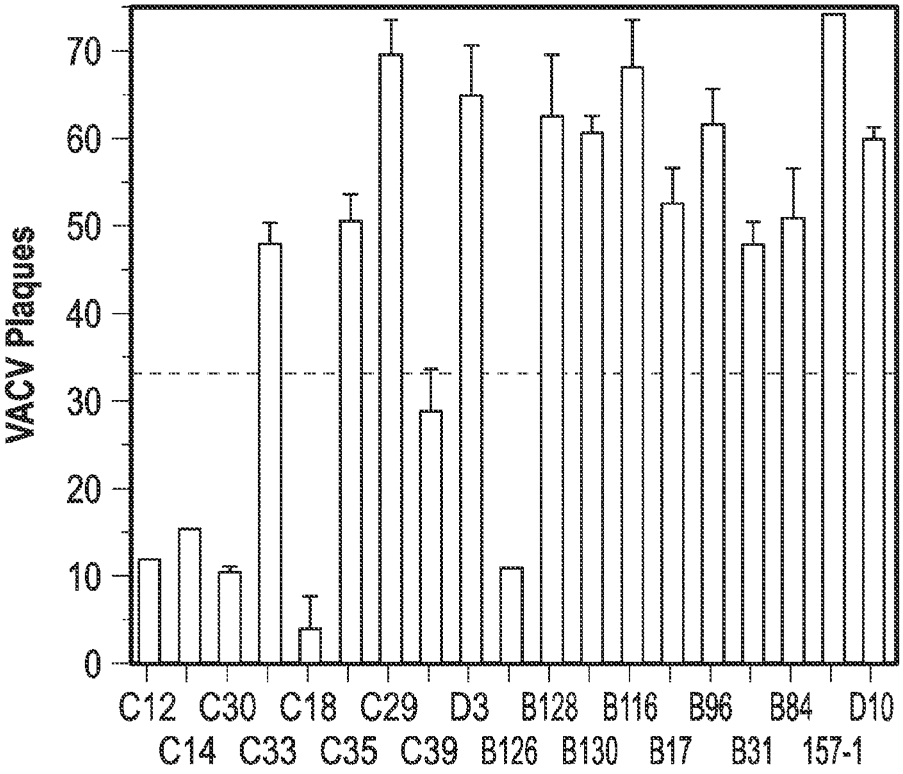
FIG. 13 shows results of a new EEV neutralization assay. 50% plaque reduction level indicated by the dashed line. "D10" is medium alone negative control. "157-1" is unvaccinated human negative control.

In brief, $VACV_{WR}$ (80 PFU) EEV (standard preparation of secreted EEV as the 48 hr supernatant of $VACV_{WR}$ infected HeLa cells, titered and kept at 4° C. for ≤30 days, ref. (Bell et al., *Virology* 325:425 (2004), Lustig et al., *Virology* 328:30 (2004), Viner et al., *Microbes Infect* 7:579 (2005)) was incubated with 10% rabbit complement plus 1 μg/ml anti-B5 mAb for 60 min at 37° C., then added to Vero cells. After 1 hr, virus was washed from the monolayer and cells were incubated 42 hrs at 37° C. and then developed with crystal violet and VACV plaques were enumerated. This assay was performed on a large panel of human and murine anti-B5 mAbs (FIG. 13). Individual mAbs alone without complement did not exhibit any significant neutralization. Complement alone did not significantly reduce PFU ("D10" medium (DMEM+10% heat inactivated FBS) plus complement (10% rabbit complement) FIG. 13 far right). In the presence of complement, anti-B5 human mAbs with good in vivo protective efficacy (#C12, #C14, B 126) exhibited potent anti-EEV neutralization activity, while minimally protective or non-protective mAbs (#D3, #C29) did not.

Figure 14A:
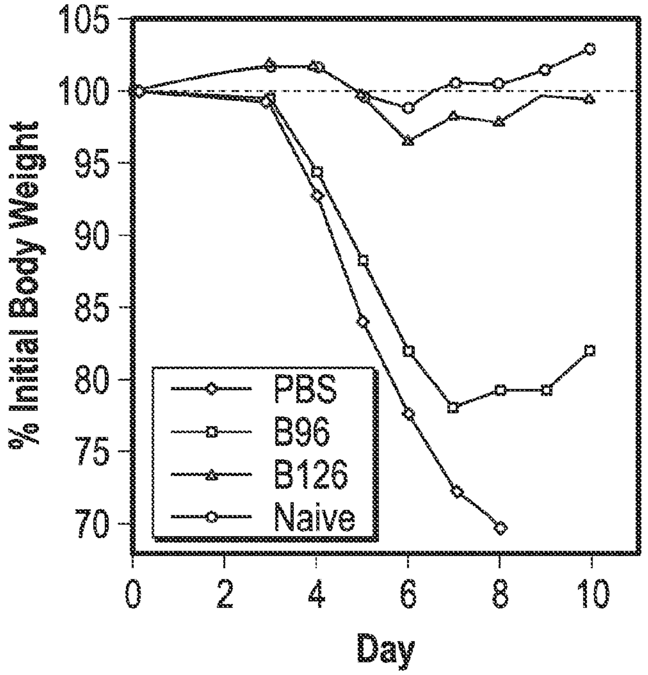
FIGS. 14A-14B show in vivo protection with particular B5R antibodies, namely A) B96 (filled square), B126 (open triangle); and B) C18 (filled square), as reflected in loss of body weight. PBS (filled circles).
Figure 14B:
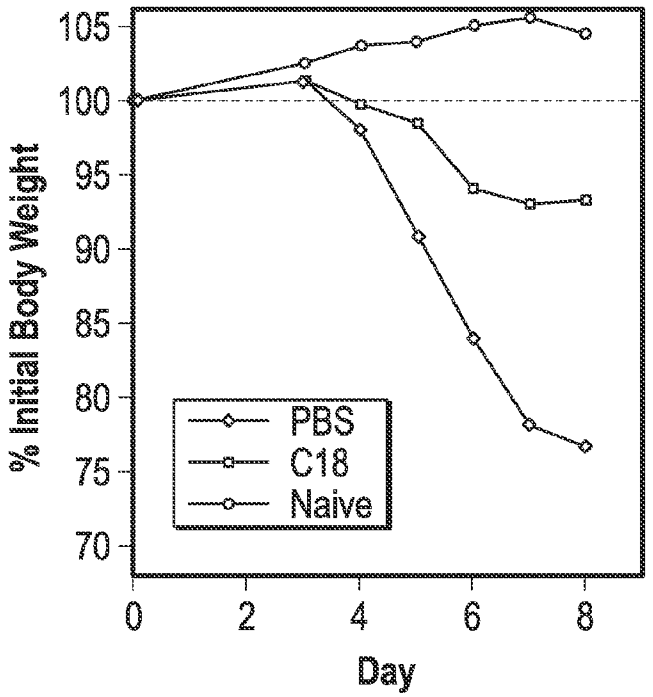
Figures 15A, 15B, 15C:
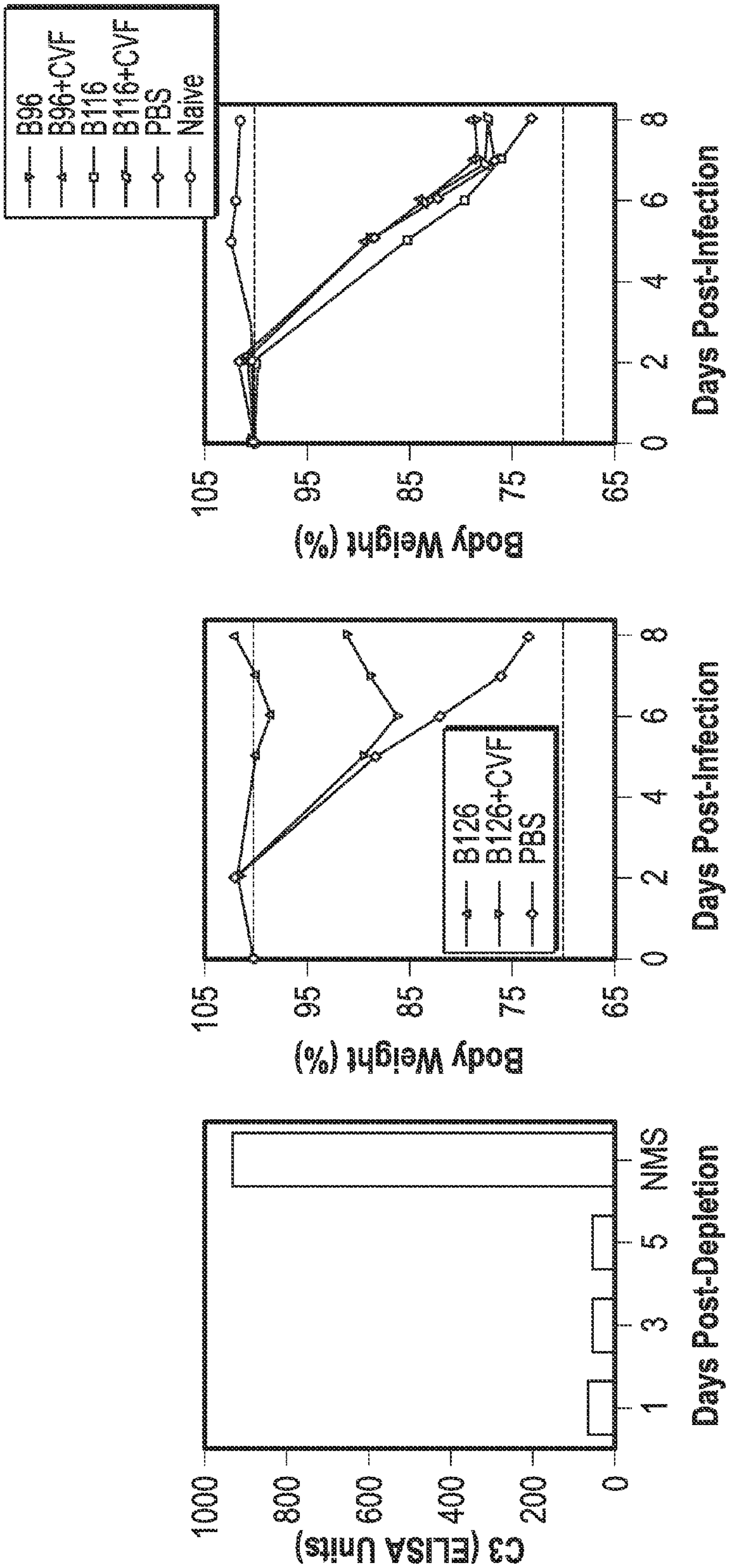
FIGS. 15A-15G show that anti-B5 protection in vivo is complement dependent. Complement depletion in vivo abrogated the majority of anti-B5 protection against VACV (A-D). (A) Complement C3 levels in cobra venom factor (CVF) treated mice, days 1-5 after treatment. Serum from mice prior to treatment (NMS) was used as control. (B-D) Complement-depleted ("+CVF") or nondepleted mice were treated with 100 μg of anti-B5 mAbs (B96, B116, or B126) or PBS ("PBS") at day −1 and challenged i.n with $5\times10^4$ PFU of purified $VACV_{WR}$ at day 0. (B-C) Mean weight loss kinetics in each group, and (D) maximum weight loss (weight nadir). (B) VACV infected mice treated with B 126 were fully protected compared with untreated infected mice (P<0.0001) but complement depleted mice had a >50% specific loss in B 126 mAb protection. (C) B96 and B 116 provided minimal protection against disease, and neither B96 nor B116 were affected by CVF treatment. (D) Abrogation of anti-B5 B126 protection by complement-depletion was highly statistically significant (P<0.0001, "B126+CVF" vs. B126 in complement-sufficient recipients, "B 126"), while there were no significant effect of complement depletion on any other group (P>>0.05, ns). One of three independent studies shown. Error bars in (D) indicate SEM in each group. Complement depletion in vivo (CVF treatment) did not affect disease in untreated mice (E-F), or the modest activities of B96 or B116 (G).
Figure 15F:
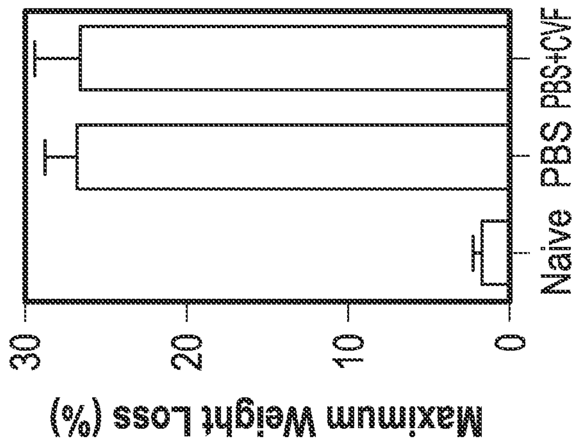
Figure 15E:
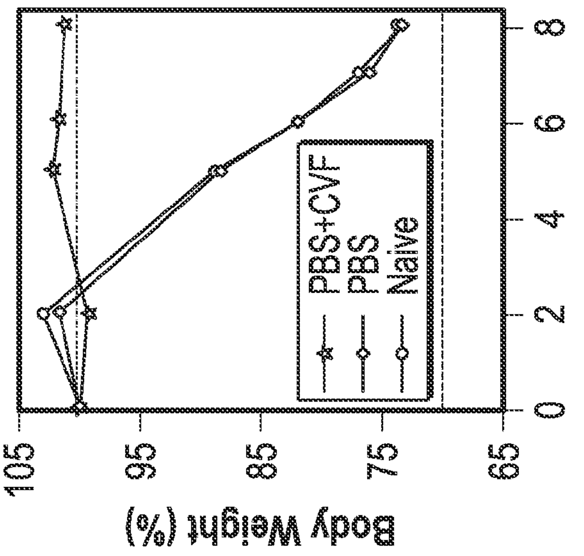
Figure 15D:
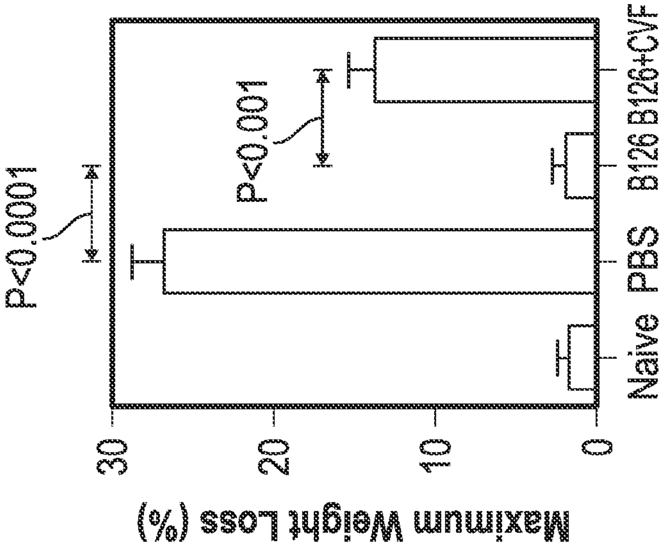
Figure 15G:
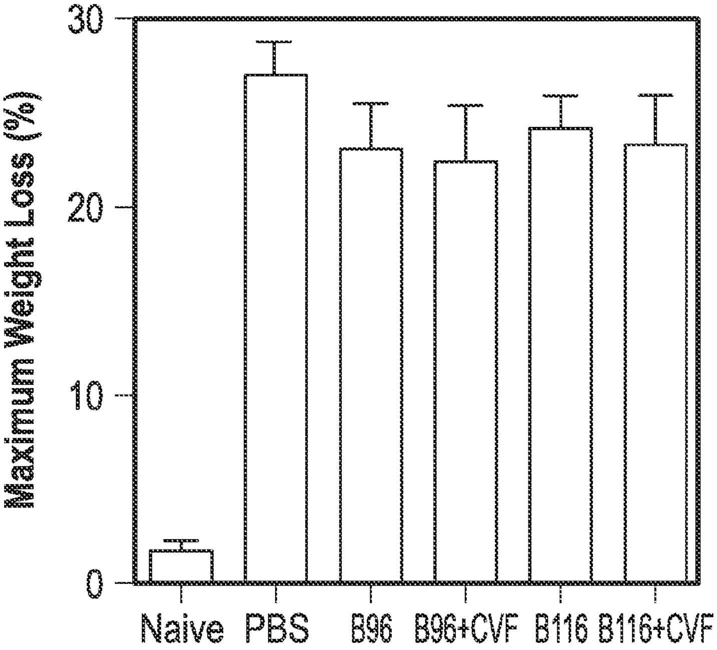
Figure 16A:
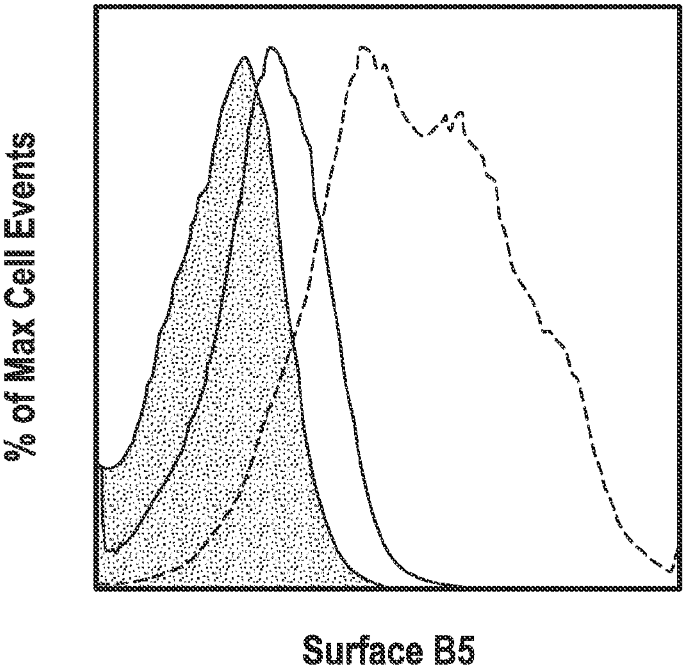
FIGS. 16A-16F show that complement and complement fixing anti-B5 IgG cooperate to efficiently mediate destruction of VACV infected cells. Anti-B5 antibodies are able to direct complement lysis of VACV infected cells due to their surface expression of B5. (A) Cell monolayers (Vero E6) were infected with $VACV_{WR}$ (MOI=5) and surface expression of B5 was tested at 4 hours (black line) and 8 hours (red line) after infection by surface staining infected cells with anti-B5 mAb and performing flow cytometry. Uninfected cells, negative control (filled curve). (B-F) Anti-B5 directed complement lysis of infected cells. Virus infected Vero E6 monolayer cells (crystal violet stained) at 40× magnification. VACV infected cells were treated with media (B) or complement ("+C'") in the absence (C) or presence of anti-B5 IgG1 mAb B96 (D) or IgG2a mAb B 126 (E). VACV infected cells were completely and specifically destroyed by anti-B5 IgG2a and complement. High magnification images (100×) shown in Supplementary FIG. 4. (F) Quantitation of live cell numbers. Destruction of VACV infected cells was highly statistically significant in the presence of anti-B 5 mAb B 126 and complement, vs. B 126 alone (P<0.0001), complement alone (P<0.001), or B96 plus complement (P<0.0001). No killing was observed for IgG1 B96 in the absence or presence of complement (P>>0.05, ns).
Figure 16B:
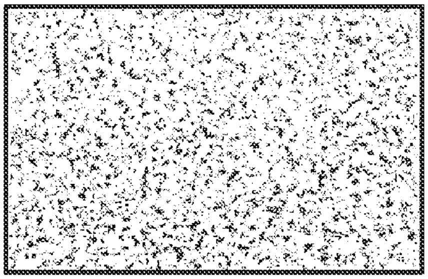
Figure 16C:
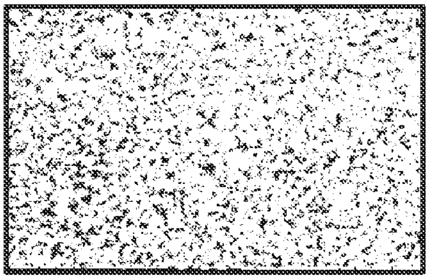
Figure 16D:
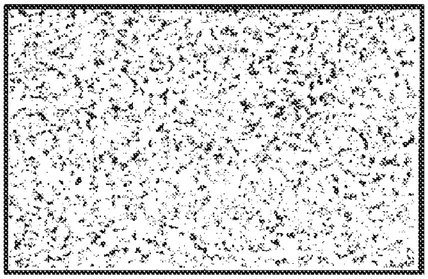
Figure 16E:
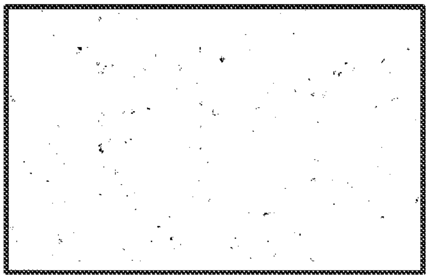
Figure 16F:
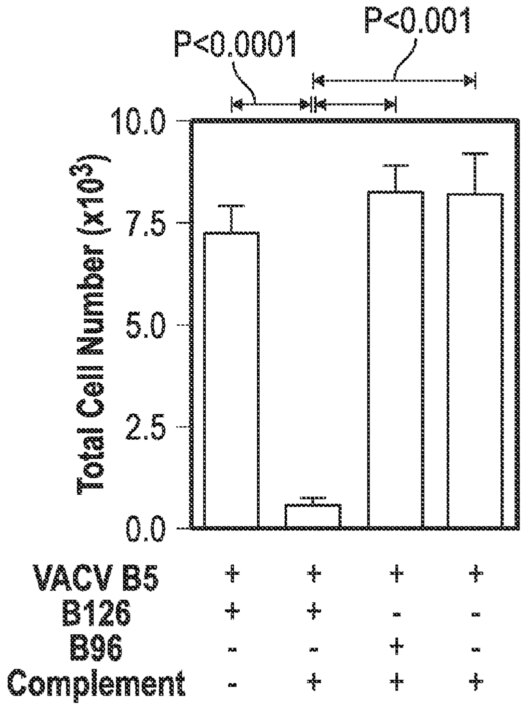

In brief, this was confirmed in vivo: mice were administered 100 μg of a particular anti-B5 mAb i.p. (or PBS as a negative control) at day −1 (5 mice/group). After light anesthesia (isofluorane), mice were infected intranasally with $3\times10^4$ PFU $VACV_{WR}$ (2 $LD_{50}$) in a 10 μl volume. Mouse weight was measured daily. Any mouse with 30% weight loss was euthanized. Monoclonal antibody B126 was highly protective, while B96 was weakly protective (FIG. 14A). Monoclonal antibody C14 was also highly protective (FIG. 14B).

The data demonstrate a high correlation between in vitro neutralization activity in the presence of complement and protection in vivo against a lethal $VACV_{WR}$ challenge (FIG. 14, Table 5). Human mAb #C18 exhibited potent in vitro neutralization activity, and provides in vivo protection against a lethal $VACV_{WR}$ (FIG. 14). The most protective murine anti-B5 mAb in vivo, #B126, was the only murine mAb to possess strong complement-mediated EEV neutralization (FIG. 13, 14).

The best comet tail inhibiting mAB, #B96, did not exhibit complement-mediated EEV neutralization, nor was this antibody effective in vivo (FIG. 13, 14) further confirming the limited predictive power of the comet tail assay. While comet tail inhibiting mAbs can be protective (Chen et al., *Proc Natl Acad Sci USA* 103:1882 (2006)), this data shows that this assay does not correlate with in vivo protection. These studies have been repeated multiple times with reproducible results. This data strongly supports the accuracy and utility of the complement-mediated EEV neutralization assay.

Example 9

This example includes demonstration of the significant role of the complement in the protection mechanism of anti-B5 antibodies.

Requirement for Complement In Vivo. B 126 antibody was distinguished from other murine anti-B5 mAbs by its ability to neutralize EV in vitro. The neutralization assay incorporated complement. B126 was also the only murine IgG2a clone identified, and IgG2a is the most efficient complement binding murine isotype. These findings indicated that the potent protective efficacy of B 126 in vivo was likely due to its ability to fix complement. To confirm this hypothesis the efficacy of B 126 after depleting complement was analyzed in vivo. Complement was depleted by administering cobra venom factor (CVF), which was confirmed by measuring serum levels of C3 (94% depletion, FIG. 15 A). Two different anti-B5 IgG1 mAbs were used for comparison to B 126: B116 and B96. Complement depletion did not affect the modest protection provided by either B96 or B 116 (average nadir weight loss: 22-24%, FIG. 15 C, G). Nor did depletion of complement affect pathogenesis or kinetics of disease in untreated mice infected with VACV (FIG. 15 E-F). In contrast, depletion of complement ablated B126 activity by more than 50% (FIG. 15 B, D). Mice treated with B 126 and infected with $VACV_{WR}$ lost no weight (average nadir weight loss: 1%, FIG. 6B, D), but complement depleted mice had a specific loss in B 126 mAb protection (average nadir weight loss: 14%, FIG. 15 B, D). This data demonstrated that the majority of the protection against VACV provided by the IgG2a anti-B5 mAb B126 was due to complement ($P<0.001$). Even so, some protection was still present in the absence of complement, and B 126 was still more protective than IgG1 isotype B5 antibodies of comparable affinity ($P<0.02$), implicating additional Fc-mediated functions. The physiological EV neutralization assay in vitro demonstrated that anti-B5 antibodies can efficiently neutralize EV virions, and this functionality was predictive of protective efficacy in vivo. Complement can function in multiple ways, and the observation that complement fixing mAbs were so effective in vivo that mice developed no clinical symptoms suggested that the VACV infection may be stopped very rapidly. These observations mean that anti-B5 antibodies are likely able to direct complement-mediated destruction of VACV infected cells, utilizing the membrane attack complex, and thereby rapidly quenching the spread of VACV, leading to resolution of the infection.

The ability of anti-B5 mAbs to direct complement lysis of cells infected with VACV was studied. While MV VACV virions (MV), the most abundant virion form, are produced intracellularly and do not have cell surface exposed proteins, EV are secreted from the plasma membrane. VACV infected cells express B5 on the surface. This expression can be detected within 4 hours of infection, and is at high levels by 8-10 hours (infected MFI 500 vs. uninfected MFI 16, FIG. 16 A).

Adherent cells were infected with VACV and examined for susceptibility to antibody directed complement lysis at time points after infection when virus expression of B5 protein led to an accumulation of B5 on the surface of infected cells (8-12 hrs). Treatment with antibody or complement alone had no effect on infected cells (FIG. 16 B, C). In stark contrast, addition of anti-B5 mAb B126 with complement resulted in rapid and complete killing of infected cells (P<0.0001. FIG. 15 E, FIG. 16 F). Treatment with a non-complement fixing anti-B5 mAb (B96 murine IgG1) in the presence of complement did not direct cell lysis, again highlighting the importance of antibody isotype and complement fixation in this antiviral activity (P>>0.05, ns. FIG. 16 D, F).

Figure 17A:
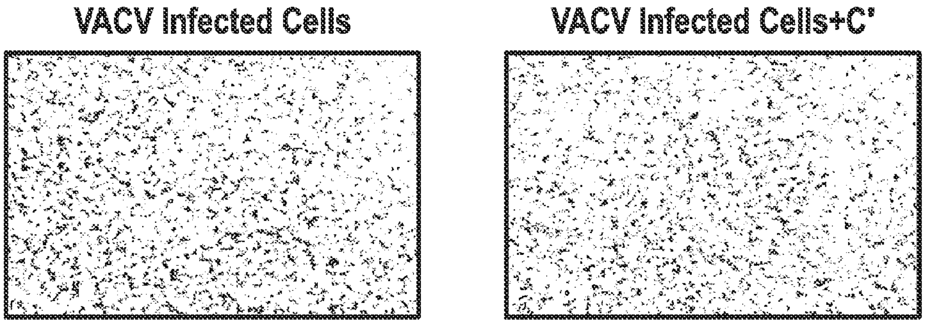
FIGS. 17A-17C show how complement and complement fixing anti-B5 IgG cooperate to efficiently mediate destruction of VACV infected cells. Anti-B5 directed complement lysis of infected cells. Virus infected Vero E6 monolayer cells (crystal violet stained) at 40× magnification. VACV infected cells were treated with media (A) or complement ("+C'") in the absence (A) or presence of human anti-B5 IgG1 mAb C12 (B) or C18 IgG1 (C). VACV infected cells were completely and specifically destroyed by anti-B5 IgG1 and complement.
Figure 17B:
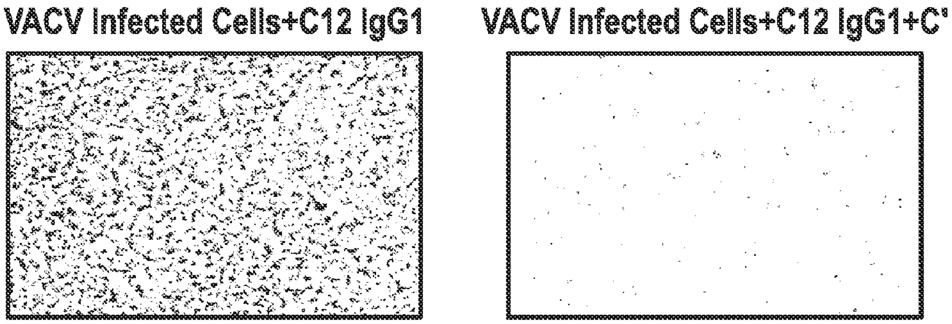
Figure 17C:
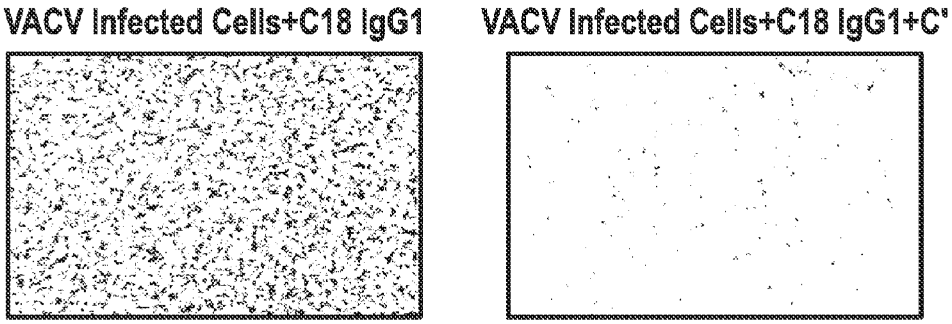

Similar data on in vitro direct complement-mediated lysis of VACV infected cells were obtained with human antibodies (FIG. 17). In summary, human antibodies that had subclasses capable of fixing complement (IgG1 and IgG3) proven to be effective in lysing infected cells. These results provided further confirmation of the importance of complement in the protective mechanism of anti-B5 antibodies.

Antibody modifications leading to increased Fcγ complement fixation have been described (see, for example, Idusogie E E, Wong P Y, Presta L G, et al. Engineered antibodies with increased activity to recruit complement. J Immunol 2001; 166:2571-5). Several studies have reported that CDC can be enhanced through improved C1q binding as a result of engineered Fc or hinge antibody regions (Dall'Acqua et al. *J Immuno;* 177:1129 (2006); Michaelsen et al. *Scand J Immuno;* 32:517 (1990) 8; Brekke et al. *Mol Immunol* 30: 1419 (1993) Scientists of Kyowa-Hacco Kogyo Co., Ltd. have described an approach to generate highly potent CDC activity by creating unique chimeric Fey construct sharing domains of human IgG1 and IgG3 isotypes (see, Natsume et al. *Cancer Res* 68:3863 (2008). The data indicate that anti-B5 antibodies with modifications enhancing complement fixation and CDC will have enhanced protective potency in vivo and therefore greater therapeutic value.

Example 10

This example includes a description of in vivo protection data of human anti-B5 antibody, anti-H3 antibody, and a combination therapy with anti-B5 antibody and anti-H3 antibody.

A combination of two mAbs specific to H3L and B5R were compared to individual mAbs and VIG for in vivo protection of mice, as described in Example 6. This study was done with fully human mAbs. In brief, SCID mice were injected at Day −1 with 100 μg human anti-B5 (C14), 200 μg human anti-H3 (#67), a combination of both, or VIG (1.25 mg per mouse). Mice were infected at Day 0 with $VACV_{NYBOH}$ i.v. $1\times10^4$ PFU.

Figure 19A:
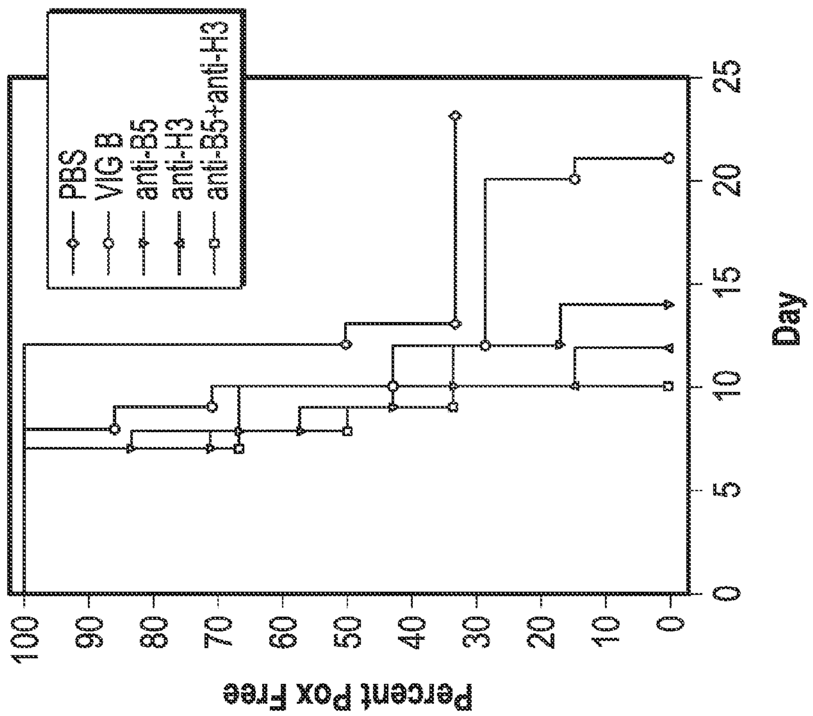
FIGS. 19A-19C show in vivo protection of SCID mice injected with human anti-B5 (C14), human anti-H3 (#67), a combination of both human antibodies or VIG. Mice were infected with VACVny, as described in Example 9 for FIG. 11. A) percent pox free mice; B) percent disease free mice; and C) percent survival.
Figure 18:
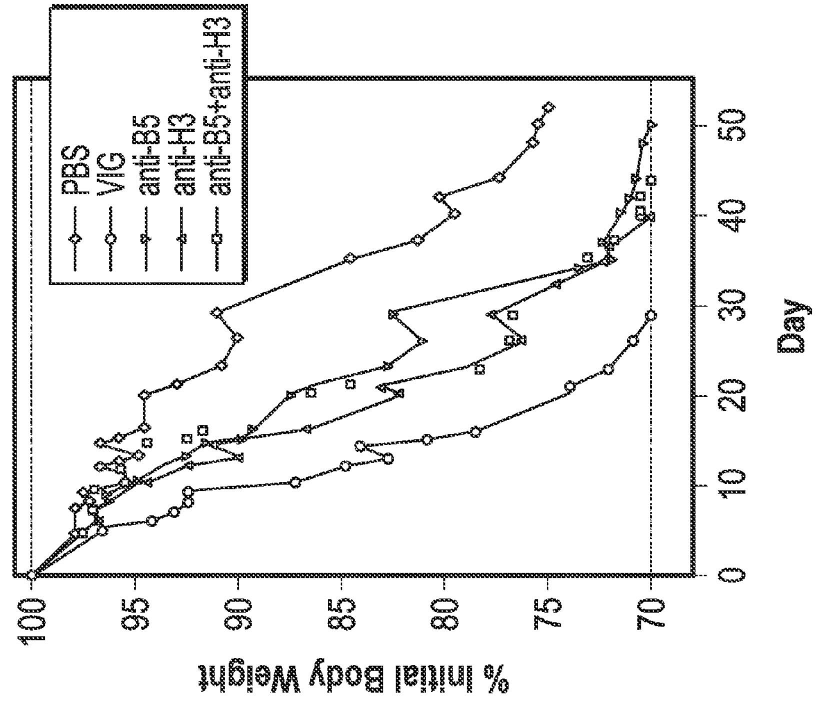
FIG. 18 shows in vivo protection of SCID mice injected with human anti-B5 (C14) (open diamond), human anti-H3 (#67) (open triangle), a combination of both human antibodies, or VIG (filled square). Control, PBS (filled circles). Mice were infected at Day 0 with VACVny.
Figure 19B:
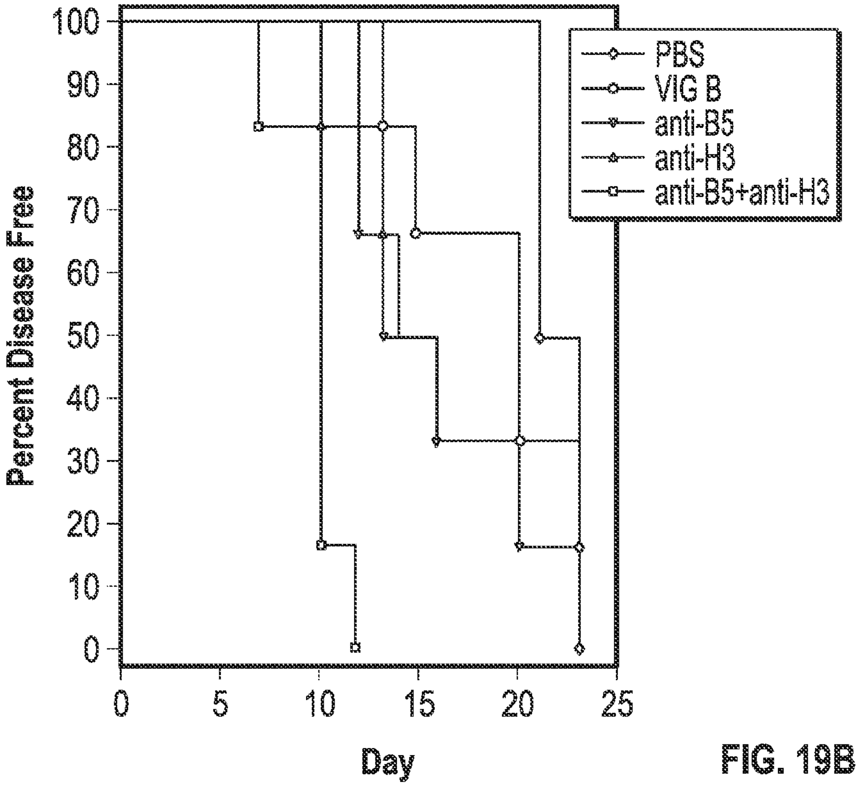
Figure 19C:
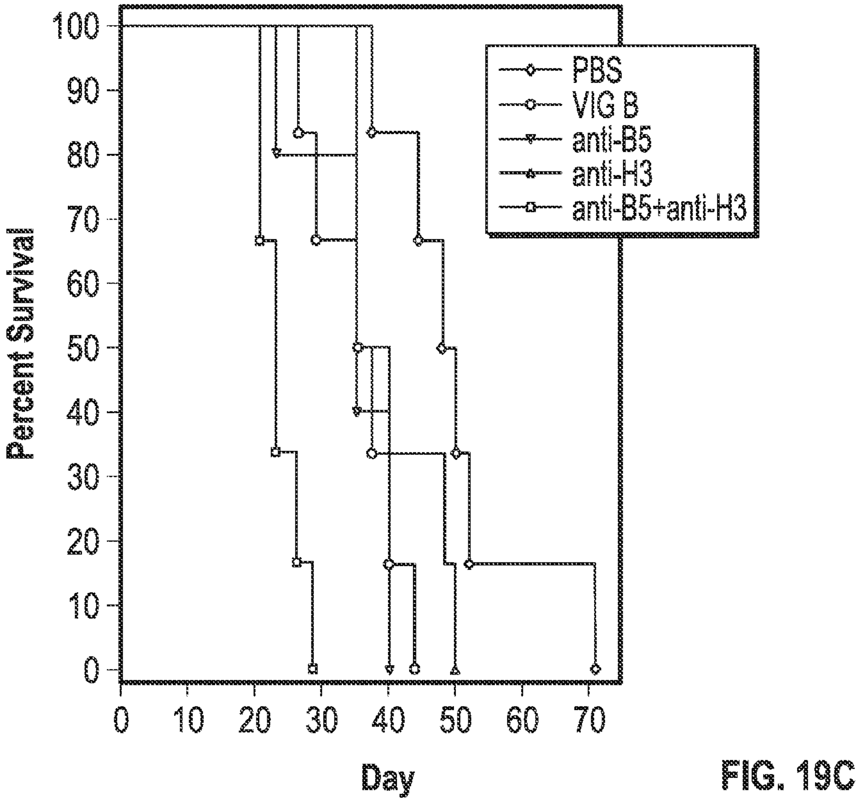

Individual administration of human mAbs specific for H3L or B5R provided equivalent protection to VIG, measured by weight loss (FIG. 18), clinical scores (pox formation, FIG. 19A), time to disease (FIG. 19B), and survival (FIG. 19C). Administration of human H3L and B5R mAbs in combination was superior to VIG or single mAb protection by all or almost all of the foregoing measurements (FIGS. 18 and 19). In particular, weight loss was substantially ameliorated by the combination therapy (P<0.0001 VIG vs. combination therapy) and survival time was extended by 13 days over VIG and 26 days over no treatment, both of which were statistically significant. This was also reflected in the measurement of disease-free mice (weight loss less than 5%, and no pox) (P<0.0109 VIG vs. combination therapy and P<0.0006 PBS vs. combination therapy.) A related clinical measure was observation of pox formation, which again was most delayed by the mAb combination therapy (P<0.0007 PBS vs. combination therapy.)

Example 11

This example includes a description of in vivo protection data of combination therapy with anti-B5 antibody and VIG.

Using an intranasal $VACV_{WR}$ challenge model, fully human mAbs can be used to supplement VIG. In brief, mice were injected at Day −1 with 600 μg human VIG, or 600 μg human VIG supplemented with 0.5 μg human anti-B5 mAb (C12), or 600 μg human VIG supplemented with 5.0 μg human anti-B5 mAb (C12), or PBS. Mice were infected at Day 0 with VACVwr i.n. ($5\times10^4$ PFU).

Figure 20:
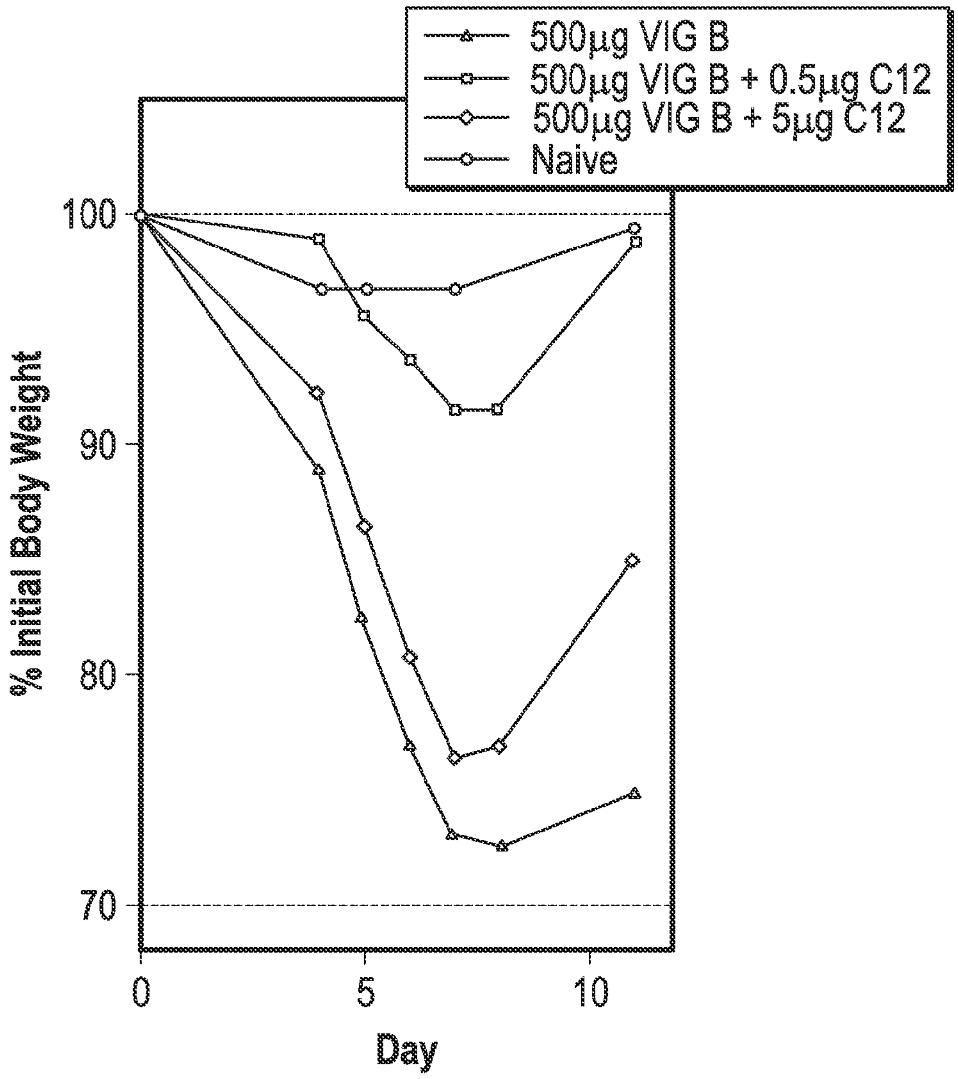
FIG. 20 shows in vivo protection with a human monoclonal antibody, anti-B5 mAb (C12) to supplement VIG. Body weight was tracked as the measure of clinical illness.

Mice treated with VIG supplemented with 0.5 or 5.0 μg human anti-B5 mAb (C12) exhibited better heath than mice provided VIG alone (FIG. 20). Body weight was tracked as the measure of clinical illness. Mean weight loss at nadir were 73% for VIG B, 76% for VIG B+0.5 μg anti-B5, and 91% for VIG B+5 μg anti-B5.

Supplementing VIG with anti-B5 human monoclonal antibody (Mab) had a significant benefit protecting mice. The data therefore indicate that monoclonal antibodies can be used to supplement VIG and provide therapeutic enhancement.

What is claimed:

1. An isolated or purified antibody or subsequence thereof that binds to an H3L envelope protein of vaccinia virus, wherein the antibody or subsequence comprises heavy chain and light chain variable region sequence CDRs identical to heavy chain and light chain variable region sequence CDRs of an antibody produced by a hybridoma deposited at American Type Culture Collection having a deposit designation of PTA-10767.

2. An isolated or purified antibody or subsequence thereof that binds to an H3L envelope protein of vaccinia virus, wherein the antibody or subsequence comprises a heavy chain variable region sequence and a light chain variable region sequence identical to a heavy chain variable region sequence and a light chain variable region sequence of an antibody produced by a hybridoma deposited at American Type Culture Collection having a deposit designation of PTA-10767.

3. The antibody or subsequence thereof of claim 1, wherein the antibody is produced by the hybridoma having the deposit designation of PTA-10767.

4. The antibody or subsequence of claim 1, wherein said antibody or subsequence thereof inhibits or competes for binding of the antibody produced by the hybridoma having the deposit designation of PTA-10767 to the H3L envelope protein of vaccinia virus.

5. The antibody of claim 1, wherein the antibody inhibits at least 50% of the binding of the antibody produced by the hybridoma having the deposit designation of PTA-10767 to the H3L envelope protein of vaccinia virus, as determined in an ELISA assay.

6. The antibody or subsequence of claim 1, wherein the antibody or subsequence thereof is humanized.

7. The antibody or subsequence thereof of claim 1, wherein the H3L envelope protein comprises or consists of a sequence set forth in SEQ ID NO:53.

8. The antibody or subsequence thereof of claim 1, wherein the antibody or subsequence thereof binds to an epitope comprised within SEQ ID NO:53.

9. The antibody or subsequence thereof of claim 1, wherein the isotype comprises IgM, IgG, IgA, IgD or IgE.

10. The antibody or subsequence thereof of claim 9, wherein the IgG or IgA isotype is selected from IgG1, IgG2, IgG3, and IgG4; and IgA1 and IgA2.

11. The antibody subsequence of claim 1, wherein the subsequence is selected from Fab, Fab', F(ab')2, Fd, single-chain Fvs (scFv), and disulfide-linked Fvs (sdFv).

12. The antibody or subsequence thereof of claim 1, wherein the antibody or subsequence inhibits vaccinia virus infection of a cell, vaccinia virus proliferation or vaccinia virus replication in vitro or in vivo.

13. The antibody or subsequence thereof of claim 1, wherein the antibody or subsequence neutralizes IMV, CEV or EEV virus, as determined by a virus neutralization assay; a complement-dependent virus neutralization assay, or a comet-tail inhibition assay.

14. The antibody or subsequence thereof of claim 1, wherein the antibody or subsequence binds to a vaccinia virus infected cell.

15. The antibody or subsequence thereof of claim 1, wherein the antibody or subsequence comprises a multimer.

16. The antibody or subsequence thereof of claim 1, further comprising one or more heterologous domains.

17. A pharmaceutical composition, comprising the antibody or subsequence thereof of claim 1, and a pharmaceutically acceptable excipient or carrier.

18. A composition, comprising at least two antibodies or subsequences thereof of claim 1.

19. A composition, comprising the antibody of claim 1 and an additional antibody that binds to a poxvirus protein.

* * * * *